(12) United States Patent
Boukharov et al.

(10) Patent No.: US 8,067,671 B2
(45) Date of Patent: Nov. 29, 2011

(54) METHODS FOR GENETIC CONTROL OF PLANT PEST INFESTATION AND COMPOSITIONS THEREOF

(75) Inventors: Andrey A. Boukharov, Wildwood, MO (US); Zijin Du, Chesterfield, MO (US); Liang Guo, St. Louis, MO (US); David K. Kovalic, Clayton, MO (US); Maolong Lu, St. Louis, MO (US); James P. McCarter, St. Louis, MO (US); Nancy M. Miller, Fenton, MO (US); Mark Vaudin, Cambridgeshire (GB); Deryck Jeremy Williams, University City, MO (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 610 days.

(21) Appl. No.: 12/101,830

(22) Filed: Apr. 11, 2008

(65) Prior Publication Data

US 2009/0188005 A1 Jul. 23, 2009

Related U.S. Application Data

(62) Division of application No. 11/360,355, filed on Feb. 23, 2006.

(60) Provisional application No. 60/655,875, filed on Feb. 24, 2005.

(51) Int. Cl.
*C12N 15/82* (2006.01)
*C12N 15/87* (2006.01)
*A01H 1/00* (2006.01)

(52) U.S. Cl. .................. 800/285; 800/279; 800/288
(58) Field of Classification Search .................. None
See application file for complete search history.

(56) References Cited

U.S. PATENT DOCUMENTS

| | | | |
|---|---|---|---|
| 6,506,559 B1 | 1/2003 | Fire et al. | 435/6 |
| 7,622,301 B2 | 11/2009 | Ren et al. | 800/286 |
| 7,659,444 B2 | 2/2010 | Ren et al. | 800/279 |
| 7,803,984 B2 | 9/2010 | Trick et al. | 800/279 |
| 2003/0061626 A1 | 3/2003 | Plaetinck et al. | 514/44 |
| 2003/0150017 A1 | 8/2003 | Mesa et al. | 800/279 |
| 2004/0098761 A1 | 5/2004 | Trick et al. | 800/279 |
| 2004/0133943 A1 | 7/2004 | Plaetinck et al. | 435/6 |
| 2005/0188438 A1 | 8/2005 | Ren et al. | 800/286 |
| 2006/0037101 A1 | 2/2006 | Ren et al. | 800/279 |
| 2007/0250947 A1 | 10/2007 | Boukharov et al. | 800/285 |
| 2007/0271630 A1 | 11/2007 | Boukharov et al. | 800/285 |
| 2009/0093620 A1 | 4/2009 | Kovalic | 536/23.1 |

FOREIGN PATENT DOCUMENTS

| | | |
|---|---|---|
| WO | WO 01/37654 | 5/2001 |
| WO | WO 03/052110 | 6/2003 |
| WO | WO 2004/098282 | 11/2004 |
| WO | WO 2005/019408 | 3/2005 |
| WO | WO 2007/095469 | 8/2007 |

OTHER PUBLICATIONS

Office Action regarding U.S. Appl. No. 11/360,355, dated Jul. 21, 2010.
Smith et al., "Total silencing by intron-spliced hairpin RNAs," *Nature*, 407:319-320, 2000.
Thomas et al., "Size constraints for targeting post-transcriptional gene silencing and for RNA-directed methylation in *Nicotiana benthamiana* using a potato virus X vector," *The Plant J.*, 25(4):417-425, 2001.
Office Action regarding U.S. Appl. No. 11/360,355, dated Jul. 22, 2008.
Declaration of Dr. Greg J. Bunkers Under 37 C.F.R. § 1.132 regarding U.S. Appl. No. 11/360,355, dated Jan. 20, 2009.
Amendment and Response to Office Action regarding U.S. Appl. No. 11/360,355, dated Jan. 21, 2009.
Final Office Action regarding U.S. Appl. No. 11/360,355, dated May 20, 2009.
Request for Continued Examination; Amendment; Telephonic Interview Summary; and Response to Final Office Action regarding U.S. Appl. No. 11/360,355, dated Sep. 18, 2009.
Office Action regarding U.S. Appl. No. 11/360,355, dated Dec. 18, 2009.
Amendment; Telephonic Interview Summary; and Response to Office Action regarding U.S. Appl. No. 11/360,355, dated May 4, 2010.
U.S. Appl. No. 60/395,153, filed Jul. 10, 2002, Trick et al.
Aboobaker et al., "Medical significance of *Caenorhabditis elegans*," *Annals of Medicine*, 32:23-30, 2000.
Aboobaker et al., "Use of RNA interference to investigate gene function in the human filarial nematode parasite *Brugio malayi*," *Mol. Biochem. Parasitol.*, 129:41-51, 2003.
Altschul et al., "Basic local alignment search tool," *J. Mol. Biol.*, 215:403-410, 1990.
Ashrafi et al., "Genome-wide RNAi analysis of *Caenorhabditis elegans* fat regulatory genes," *Nature*, 421:268-272, 2003.
Bargmann, "Neurobiology of the *Caenorhabditis elegans* genome," *Science*, 282:2028-2033, 1998.

(Continued)

*Primary Examiner* — Li Zheng
(74) *Attorney, Agent, or Firm* — SNR Denton US LLP; Erin C. Robert, Esq.

(57) ABSTRACT

The present invention is directed to controlling plant pest infestation, and particularly plant nematode infestation, by inhibiting one or more biological functions in the plant pest. The invention discloses methods and compositions for use in controlling plant pest infestation by providing one or more different recombinant double stranded RNA molecules in the diet of the pest in order to achieve a reduction in pest infestation through suppression of pest gene expression. The invention is also directed to methods for making transgenic plants that express the double stranded RNA molecules, to methods for detecting cells comprising the disclosed sequences, and to methods for detecting the disclosed sequences in biological samples.

9 Claims, No Drawings

OTHER PUBLICATIONS

Barker et al., "Plant and soil nematodes: societal impact and focus for the future," The Committee on National Needs and Priorities in Nematology, Cooperative State Research Service, U.S. Department of Agriculture and Society of Nematologists, 1994.
Burglin et al., "*Caenorhabditis elegans* as a model for parasitic nematodes," *Intl. J. for Parasitology*, 28:395-411, 1998.
Davis et al., "Nematode parasitism genes," *Annu. Rev. Phytopathol.*, 38:365-396, 2000.
Dong et al., "Genetic analysis of parasitism in the soybean cyst nematode heterodera glycines," *Genetics*, 146:1311-1318, 1997.
Elbashir et al., "RNA interference is mediated by 21- and 22-nucleotide RNAs," *Genes Dev.*, 5(2):188-200, 2001.
EST Accession No. CB278684, dated Feb. 26, 2003.
EST Accession No. CB281513, dated Feb. 27, 2003.
EST Accession No. CB374668, dated Mar. 18, 2003.
EST Accession No. CB375671, dated Mar. 18, 2003.
Fairbairn et al., "Plant delivered RNAi (PD-RNAi): a novel strategy to control plant parasitic nematodes by inactivating nematode genes in planta," (Annual Meeting Abstract #372), American Society for Plant Biology, 2005.
Fire et al. "Potent and specific genetic interference by double-strnaded RNA in *Caenorhabditis elegans*," *Nature*, 391:806-811, 1998.
Foster et al., "Wolbachia genome of *Brugia malayi*: endosymbiont evolution within a human pathogenic nematode," *PLOIS Biol.*, 3(4):599-614, 2005.
Fraser et al., "Functional genomic analysis of *C. elegans* chromosome I by systematic RNA interference," *Nature*, 408:325-330, 2000.
Geary et al., "*Caenorhabditis elegans*: how good a model for veterinary parasites," *Veterinary Parasitology*, 101:371-386, 2001.
Gonczy et al., "Functional genomic analysis of cell division in *C. elegans* using RNAi of genes on chromosome III," *Nature*, 408(16):331-336, 2000.
Hamilton et al., "A species of small antisense RNA in post-transcriptional gene silencing in plants," *Science*, 286:950-952, 1999.
Harris et al., "Wormbase: a multi-species resource for nematode biology and genomics," *Nucleic Acids Research*, 32:D411-D417, 2004.
Hussein et al., "Suppression of secreted acetylcholinesterase expression in *Nippostrongylus brasiliensis* by RNA interference," *Mol. Biochem. Parasitol.*, 122:91-94, 2002.
Imhof et al., "Fitness effects of advantageous mutations in evolving *Escherichia coli* populations," *Proc. Natl Acad. Sci. USA*, 98:1113-1117, 2001.
Kamath et al., "Effectiveness of specific RNA-mediated interference through ingested double-stranded RNA in *Caenorhabditis elegans*," *Genome Biol.* 2(1):Research 0002.1-0002-10, 2001.
Kamath et al., "Systematic functional analysis of the *Caenorhabditis elegans* genome using RNAi," *Nature*, 421:231-237, 2003.
Kwa et al., "Beta-tubulin genes from the parasitic nematode *Haemonchus contortus* modulate drug resistance in *Caenorhabditis elegans*," *J. Mol. Biol.*, 246:500-510, 1995.
Lustigman et al., "RNA interference targeting cathepsin L and Z-like cysteine proteases of *Onchocerca volvulus* confirming their essential function during L3 molting," *Mol. Biochem. Parasitol.*, 138:165-170, 2004.
Maeda et al., "Large-scale analysis of gene function in *Caenorhabditis elegans* by high-throughput RNAi," *Curr. Biol.*, 11(3):171-176, 2001.
Martin, "Modes of action of anthelmintic drugs," *Vet J.*, 154:11-34, 1997.
Martinez et al., "Single-stranded antisense siRNAs guide target RNA cleavage in RNAi," *Cell*, 110:563-574, 2002.
McCarter et al., "Analysis and functional classification of transcripts from the nematode *Meloidogyne incognita*," *Genome Biology*, 4:R26.1-R26.19, 2003.
McCarter et al., Nematode gene sequences: update for Dec. 2003, *J. of Nematology*, 35(4):465-469, 2003.
McCarter, "Genomic filtering: an approach to discovering novel antiparasitics," *Trends in Parasitology*, 20(10):462-468, 2004.
McManus et al., "Gene silencing in mammals by small interfering RNAs," *Nature Reviews*, 3:737-747, 2002.
Mitreva et al., "A survey of SL1-spliced transcripts from the root-lesion nematode *Pratylenchus penetrans*," *Mol. Gen. Genomics*, 272:138-148, 2004.
Mitreva et al., "Comparative genomics of gene expression in the parasitic and free-living nematodes *Strongyloides stercoralis* and *Caenorhabditis elegans*," *Genome Research*, 14:209-220, 2004.
Montgomery et al., "RNA as a target of double-stranded RNA-mediated genetic interference in *Caenorhabditis elegans*," *Proc. Natl. Acad. Sci. USA*, 95:15502-15507, 1998.
Omura et al., "An anthelmintic compound, nafuredin, shows selective inhibition of complex I in *Helminth mitochondria*," *Proc. Natl. Acad. Sci. USA*, 98:60-62, 2001.
Papp et al., "Dosage sensitivity and the evolution of gene families in yeast," *Nature*, 424:194-197, 2003.
Papp et al., "Metabolic network analysis of the causes and evolution of enzyme dispensability in yeast," *Nature*, 429:661-664, 2004.
Parkinson et al., "A transcriptomic analysis of the *Phylum nematoda*," *Nature Genetics*, 36:1259-1267, 2004.
Piano et al., "Gene clustering based on RNAi phenotypes of ovary-enriched genes in *C. elegans*," *Curr. Biol.*, 12:1959-1964, 2002.
Piano et al., "RNAi analysis of genes expressed in the ovary of *Caenorhabditis elegans*," *Curr. Biol.*, 10:1619-1622, 2000.
Redmond et al., "Expression of *Haemonchus contortus* pepsinogen in *Caenorhabditis elegans*," *Mol. Biochem. Parasitol.*, 112:125-131, 2001.
Ruvkun, "The taxonomy of developmental control in *Caenorhabditis elegans*," *Science*, 282:2033-2041, 1998.
Scholl et al., "Horizontally transferred genes in plant parasitic nematodes: a high-throughput genomic approach," *Genome Biology*, 4:R39.1-R39.12, 2003.
Simmer et al., "Genome-wide RNAi of *C. elegans* using the hypersensitive rrf-3 strain reveals novel gene functions," *PLOS Biol.*, 1(1):77-84, 2003.
Sonnichsen et al., "Full-genome RNAi profiling of early embryogenesis in *Caenorhabditis elegans*," *Nature*, 434:462-469, 2005.
Urwin et al., "Ingestion of double-stranded RNA by preparasitic juvenile cyst nematodes leads to RNA interference," *Mol. Plant Microbe Interact.*, 15:747-752, 2002.
Winston et al., "Systemic RNAi in *C. elegans* requires the putative transmembrane protein SID-1," *Science*, 295:2456-2459, 2002.
Winzeler et al., "Functional characterization of the *S. cerevisiae* genome by gene deletion and parallel analysis," *Science*, 285:901-906, 1999.
Zheng et al., "Conservation and diversification of Wnt signaling function during the evolution of nematode vulva development," *Natl. Genet.*, 37:300-304, 2005.
Davy et al., "A protein-protein interaction map of the *Caenoryhabditis elegans* 26S proteasome," *EMBO Reports*, 21(9):821-828, 2001.
Eisen, "Phylogenomics: improving functional predictions for uncharacterized genes by evolutionary analysis," *Genome Research*, 8:163-167, 1998.
Response to Official Action regarding U.S. Appl. No. 11/360,355, dated Dec. 20, 2010.
Official Action regarding U.S. Appl. No. 11/360,355, dated Mar. 17, 2011.
Hamilton et al., "Two classes of short interfering RNA in RNA silencing," *The EMBO J.*, 21(17):4671-4679, 2002.
Schwarz et al., "Asymmetry in the assembly of the RNAi enzyme complex," *Cell*, 115:199-208, 2003.
Silhavy et al., "A viral protein suppresses RNA silencing and binds silencing-generated, 21- to 25-nucleotide double-stranded," *The EMBO J.*, 21(12):3070-3080, 2002.
Qiu et al., "A computational study of off-target effects of RNA interference," *Nucleic Acids Res.*, 33(6):1834-1847, 2005.
Response to Office Action regarding U.S. Appl. No. 11/360,355, dated Jun. 15, 2011.
Notice of Allowance regarding U.S. Appl. No. 11/360,355, dated Aug. 30, 2011.

METHODS FOR GENETIC CONTROL OF PLANT PEST INFESTATION AND COMPOSITIONS THEREOF

CROSS REFERENCE TO RELATED APPLICATIONS

This application is a division of U.S. application Ser. No. 11/360,355, filed Feb. 23, 2006, which claims the benefit of priority to U.S. Provisional Patent Application Ser. No. 60/655,875 filed Feb. 24, 2005, and the sequence listing filed along with that application, which is incorporated herein by reference in its entirety, each of the disclosures of which are hereby incorporated by reference in their entirety.

FIELD OF THE INVENTION

The present invention relates generally to the field of molecular biology and more specifically to the genetic control of plant pests, and even more particularly to the genetic control of *Heterodera* nematode infestations in plants. More specifically, the present invention relates to methods for modifying expression of one or more polynucleotide and/or protein molecules in one or more cells or tissues of a pest species. The present invention discloses substantially the entire genome sequence of the plant nematode pest, *Heterodera glycines*, and describes the use of these sequences to modify the expression of one or more target polynucleotide or protein molecules in at least the cells of a *Heterodera* species by providing in its diet a dsRNA that comprises a part of, or all, or substantially all of one or more polynucleotide molecules of the present invention.

BACKGROUND OF THE INVENTION

Plants and animals are targets of many different pests, including but not limited to nematode and insect pest species. Crops are often the targets of nematode infestations. Chemical nematicides are not effective in eradicating the nematode infestations. Chemical pesticidal agents are not selective and exert their effects on non-target fauna as well, often effectively sterilizing for a period of time a field over which the chemical nematicidal agents have been applied. Some chemical pesticidal agents have been shown to accumulate in food, and to exhibit adverse effects on workers that manufacture and apply such chemical agents. Thus there has been a long felt need for methods for controlling or eradicating nematode pest infestation on or in plants, i.e., methods which are selective, environmentally inert, non-persistent, biodegradable, and that fit well into pest resistance management schemes. Plant biotechnology provides a means to control pest infestations by providing plants that express one or more pest control agents. Recombinant pest control agents have generally been reported to be proteins selectively toxic to a target pest that are expressed by the cells of a recombinant plant. Recently, small RNA molecules provided in the diet of the pest species *Meloidogyne incognita* have been shown to exhibit effects on the viability of the pest by affecting gene expression in the pest cells (Tobias et al. WO 01/37654 A2). Recombinant approaches to plant pest control can be selective, and are environmentally inert and non-persistent because they are fully biodegradable.

The phenomenon of dsRNA mediated gene silencing has been demonstrated in a number of plant and animal systems (Fire et al. 1998 Nature 391:806-811; Waterhouse et al. 1998 PNAS USA 95:13959-13964; Tabara et al. 1998 Science 282:430-431; Fire et al. WO 99/32619 A1; Trick et al. WO 2004/005485 A2). Methods for delivering dsRNA into the animal systems involved generating transgenic insects that express double stranded RNA molecules or injecting dsRNA solutions into the body of the animal or within the egg sac prior to or during embryonic development. Double stranded RNA mediated gene suppression has been demonstrated in plant parasitic nematodes either by providing dsRNA or miRNA's in the nematodes' diet or by soaking the nematodes in solutions containing such RNA molecules (Atkinson et al., (The University of Leeds) WO 03/052110 A2; Trick et al., (Kansas State University Research Foundation) US 2004-009876A1). Cyst nematodes (*Heterodera* and *Globodera* species) are particularly damaging pests of crop plants. Cyst nematodes include but are not limited to *Heterodera avenae, H. cruciferae, H. glycines, H. hordecalis, H. latipons, H. oryzae, H. oryzicola, H. rostochinesis, H. zeae, H. schachtii, G. achilleae, G. artemisiae, G. mexicana, G. millefolii, G. pallida, G. rostochiensis, G. tabacum, G. tabacum solanacearum, G. tabacum tabacum, G. tabacum virginiae, Globodera* sp. Bouro, *Globodera* sp. Canha, *Globodera* sp. Ladeiro, *Globodera* sp. New Zealand-EK-2004, and *Globodera* sp. Peru-EK-2004. These species are known to parasitize a wide variety of crops including, but not limited to barley, corn, oats, rice, rye, wheat, cabbage, cauliflower, soybean, sugar beet, spinach, mustards, and potato. Cyst nematodes are particularly problematic. Eggs persist and remain viable in the soil for many years. Genetic resistance by conventional crop breeding has limited success in identifying resistance genes effective against the wide variety of races and biotypes of the cyst nematodes. Of particular concern is the soybean cyst nematode, *Heterodera glycines*, herein referred to as SCN.

Therefore, there exists a need for improved methods and compositions useful to modulate gene expression by repressing, delaying or otherwise reducing gene expression within a particular plant nematode pest for the purpose of controlling the nematode infestation or to introduce novel agronomically valuable phenotypic traits.

SUMMARY OF THE INVENTION

The present invention comprises methods and compositions for inhibiting expression of one or more target genes and proteins at least in cyst nematodes such as members of the *Heterodera* and *Globodera* species. More specifically, the present invention comprises a method of modulating or inhibiting expression of one or more target genes in *Heterodera glycines* and *Heterodera schactii*, to cause cessation of feeding, growth, development, reproduction and infectivity and eventually result in the death of the nematode pest. The method comprises introduction of partial or fully, stabilized double-stranded RNA (dsRNA) or its modified forms, such as small interfering RNA (siRNA) or micro RNA (miRNA) sequences, into the cells of the nematode wherein expression of at least one or more target genes is inhibited in the target nematode pest, wherein inhibition of the one or more target genes exerts a deleterious effect upon the nematode pest, wherein the dsRNA, siRNA, or miRNA are derived from the target gene sequences, specifically inhibit such target genes in the target pest, and so are specific to nematode pests such as those of the *Heterodera* species. It is specifically contemplated that the methods and compositions of the present invention will be useful in limiting or eliminating *Heterodera* infestation in or on any cyst nematode host by providing one or more compositions comprising dsRNA molecules in the diet of the nematode, wherein the diet is all or part of a plant cell.

In another aspect of the present invention, DNA molecules of the present invention comprise molecules that function as promoter sequences, polypeptide coding sequences, non-coding regulatory sequences, or polyadenylation sequences isolated from the genome of the soybean cyst nematode, the polynucleotide sequence of which is at least from about 75, 76, 77, 78, 79, 80, 81, 82, 83, 84, 85, 86, 87, 88, 89, 90, 91, 92, 93, 94, 95, 96, 97, 98, 99, or about 100% identical to sequences selected from the group consisting of SEQ ID NO: 1 through SEQ ID NO:45568, the complement thereof, or a portion thereof. A DNA molecule selected from the group consisting of SEQ ID NO:97730 through SEQ ID NO:119145 exhibits promoter activity, and a DNA molecule selected from the group consisting of SEQ ID NO:45569 through SEQ ID NO:47643 comprises at least one protein coding sequence, whether or not a complete open reading frame is exhibited.

Accordingly, in another aspect of the present invention, a set of isolated and purified polynucleotide sequences as set forth in SEQ ID NO:45569 through SEQ ID NO:47643 are provided as target sequences for the design of DNA constructs that express a stabilized dsRNA, siRNA, or miRNA molecule for inhibition of expression of a target gene in a nematode pest. A stabilized dsRNA, siRNA, or miRNA molecule can comprise two or more polynucleotide molecules that are arranged in a sense and an antisense orientation relative to at least one promoter, wherein the polynucleotide molecule that comprises a sense strand and an antisense strand are linked or connected by a spacer sequence of at least from about five to about one thousand nucleotides, wherein the sense strand and the antisense strand are at least about the same length, and wherein each of the two polynucleotide sequences shares at least about 80% sequence identity, at least about 90%, at least about 95%, at least about 98%, or even about 100% sequence identity, to a polynucleotide sequence as set forth in one of SEQ ID NO:45569 through SEQ ID NO:47643.

The present invention provides a method for identifying a DNA molecule for use as a DNA construct expressing a dsRNA-mediated gene silencing sequence in a plant cell, comprising selecting a target polynucleotide molecule of a *Heterodera glycines* polynucleotide sequence comprising 21 or more contiguous nucleotides wherein said polynucleotide sequence is selected from the group consisting of SEQ ID NO:45569-50775, SEQ ID NO:45569-47643, and SEQ ID NO:47644-50775.

The present invention also provides a recombinant DNA molecule for use in plant transformation, constructed to contain at least one polynucleotide molecule transcribed as a single stranded RNA molecule. The single stranded RNA molecule is capable of forming in vivo a double stranded RNA molecule through intermolecular hybridization that, when provided in the diet of a nematode pest, inhibits the expression of at least one target gene in one or more cells of the target organism. The polynucleotide molecule is operably linked to at least one promoter sequence that functions in a transgenic plant cell to transcribe the polynucleotide molecule into one or more ribonucleic acid molecules. The RNA molecule(s) self assemble into double stranded RNA molecules and are provided in the diet of a target pest that feeds upon the transgenic plant. The provision of the dsRNA molecule in the diet of the pest achieves the desired inhibition of expression of one or more target genes within the pest organism, resulting in fecundicity, morbidity, and/or mortality of the target pest.

The present invention also provides a recombinant plant cell having in its genome at least one recombinant DNA sequence that is transcribed to produce at least one dsRNA molecule that functions when the cell and/or its contents are ingested by a target nematode or pest to inhibit the expression of at least one target gene in the target nematode or pest. The dsRNA molecule is transcribed from all or a portion of a polynucleotide molecule that at least in part exhibits from about 75 to about 100% identity to a target nematode specific polynucleotide sequence as set forth in SEQ ID NO:45569 through SEQ ID NO:50775.

The present invention also provides a recombinant DNA construct for expression of a dsRNA-mediated gene silencing sequence in a plant cell, which comprises at least two different target sequences that, when expressed in vivo as RNA sequences and provided in the diet of a target nematode pest, inhibit the expression of at least two different target genes in one or more cells or tissues of the target nematode pest. A first target sequence exhibits at least from about 75 to about 100 percent identity to a first specific polynucleotide sequence region as set forth in SEQ ID NO:45569-SEQ ID NO:50775, and a second target sequence that is different from the first target sequence exhibits at least about 75 to about 100 percent identity to a second specific polynucleotide sequence region as set forth in SEQ ID NO:45569 through SEQ ID NO:50775, wherein the two or more target sequences are assembled in a DNA construct and expressed together as a single RNA transcript, and are constructed to form one or more dsRNA's useful in suppression of the one or more target genes. The DNA construct is transformed into a soybean cell, and the cell is regenerated into a recombinant plant. The dsRNA molecules are thus provided in the diet of the target nematode pest in a target nematode pest inhibitory concentration. Ingestion by the target nematode pest of recombinant plant cells or tissues expressing the recombinant dsRNA achieves the desired inhibition of expression of one or more target genes in the nematode, resulting in the fecundicity, morbidity, and/or mortality of the target nematode pest.

Another aspect of the present invention is the use of the nucleotide sequences disclosed herein to identify target sequences that occur in the transcript RNA of other plant pests, in particular insect pests, fungal pests, and nematode pests, that could be targeted simultaneously and/or contemporaneously with a single expression construct designed to suppress related genes in multiple plant pests by identifying sequences of sufficient length and identity in two or more different plant pests, and ensuring that the DNA construct used to produce a recombinant plant expresses one or more dsRNA molecules that function to effectively suppress one or more related genes in the two or more different plant pests. In particular, some contiguous nucleotide sequences equal to or greater than about 21-24 nucleotides in length are identified herein to be present within the genome of the soybean cyst nematode (SCN) *Heterodera glycines* and have been identified to be present as well in *Heterodera schactii*, and to some extent, other pest species as well, such as in several other nematode pest species as well as in other plant pest species such as specific insect nucleotide sequences, and in animal pest species such as insect pest species. Such sequences may be useful for effectively suppressing a target sequence in these plant pests, particularly when expressed as a dsRNA molecule in a recombinant plant cell that is provided in the diet of the pest, and can provide resistance to the plant from pest infestation from all or substantially all pests in which such sequences appear, in particular if the sequences in common are within genes shown to be essential for survival, reproduction, mobility, and/or development and differentiation.

The target sequences disclosed in the present invention can be used to identify related target sequences that occur in the transcript RNA of other pest species, particularly nematode species including but not limited to pests such as *Heterodera* species such as *H. avenae, H. ciceri, H. crucifera, H. cyperi, H. fici, H. goettingiana, H. hordecalis, H. humuli, H. latipons, H. litoralis, H. medicaginis, H. mediterranea, H. oryzae, H. oryzicola, H. riparia, H. rostochinesis, H. salixophila, H. schachtii, H. sorghi, H. trifolii, H. turcomanica*, and *H. zeae*, *Meloidogyne* species such as *M. arenaria, M. chitwoodi, M. artiellia, M. fallax, M. hapla, M. javanica, M. incognita, M. microtyla, M. partityla, M. panyuensis*, and *M. paranaensis*, *Globodera* species such as *G. pallida, G. rostochiensis*, and *G. tabacum, Pratylenchus* species such as *P. brachyurus, P. crenatus, P. coffeae, P. magnica, P. neglectu, P. penetrans, P. scribneri, P. thornei*, and *P. vulnus*. Other plant pest nematode species that are within the scope of the present invention include but are not limited to *Xiphinema* species, *Nacobbus* species, *Hoplolaimus* species, *Paratylenchus* species, *Rotylenchulus* species, *Criconemella* species, *Hemicycliophora* species, *Helicotylenchus* species, *Rotylenchus* species, *Belonolaimus* species, *Trichodorus* species, *Tylenchorhynchus* species, *Radopholus* species, *Longidorus* species, *Dolichodorus* species, *Aphenlenchoides* species, *Ditylenchus* species, *Anguina* species, and *Tylenchulus* species. A DNA construct that expresses a dsRNA molecule in a plant cell that has a target sequence common to multiple plant pests provides plant resistance to pest infestation from each pest containing such target sequences. A particular target sequence can be amplified within a single dsRNA transcript, and can contain only a single contiguous sequence of at least from about 17 to about 21 to about 50 nucleotides in common between any combination of pests, or can be comprised of a chimera consisting of various contiguous sequences of at least from about 17 to about 21 to about 50 or more nucleotides, each such contiguous sequence either being in common between two or more pests, or unique to only a single pest, such that the chimera, when present as a dsRNA sequence and provided in the diet of any one or more of the targeted pests, results in the effective control such one or more pests.

The present invention also provides a method for producing a transgenic plant by introducing into the genome of the plants' cells a polynucleotide sequence consisting of all or a portion of at least one of the aforementioned SCN specific recombinant DNA sequences, linked to linked substantially the complement of that sequence. Transgenic plants are generated from the transformed plant cell, and progeny plants, seeds, and plant products, each comprising the polynucleotide sequence, are produced from the transgenic plants.

The methods and compositions of the present invention may be applied to any monocot and dicot plant, depending on the pest species to be controlled and the host range of the nematode pest. Specifically, the plants are intended to comprise without limitation alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugar beet, sugarcane, sunflower, sweet potato, sweetgum, tangerine, tea, tobacco, tomato, turf, a vine, watermelon, wheat, yams, and zucchini plants. Preferably, the present invention is related to a transgenic soybean plant that contains in its genome a DNA construct that expresses a dsRNA molecule from any sequence of the present invention.

The invention also provides a computer readable medium having recorded thereon one or more of the sequences as set forth in SEQ ID NO:1 through SEQ ID NO:171306 and, with reference to nucleotide sequences, the complements thereof, for use in a number of computer based applications, including but not limited to DNA identity and similarity searching, protein identity and similarity searching, transcription profiling characterizations, comparisons between genomes, and artificial hybridization analyses.

BRIEF DESCRIPTION OF THE SEQUENCES

SEQ ID NO:1-SEQ ID NO:45568 correspond to individual sequences (singletons) and assembled singletons forming contiguous overlapping sequences (contigs) derived from DNA sequence analysis of one or more libraries produced from the genome of the soybean cyst nematode strain OP25.

SEQ ID NO:45569-SEQ ID NO:97729 correspond to sequences predicted to encode various proteins, tRNA's, rRNA's and the like, which were identified using the bioinformatics described herein as applied to SEQ ID NO:1-SEQ ID NO:45568, and are further defined in blocks of sequences corresponding to coding sequences characterized as (a) essential to SCN survival (SEQ ID NO:45569-SEQ ID NO:50775) and (b) other coding sequences and elements (SEQ ID NO:50776-SEQ ID NO:97729); and where the essential sequences are further defined in blocks of sequences corresponding to unigenes, EST's, or cDNA's which were (c) linked through bioinformatics analyses described herein to counterpart sequences entirely or partially known in the art (SEQ ID NO:47644-SEQ ID NO:50775) and (d) unique sequences exhibiting no known relationship to sequences known in the art (SEQ ID NO:45569-47643).

SEQ ID NO:97730-SEQ ID NO:119145 correspond to sequences predicted to comprise all or substantially all of one or more SCN promoter sequences.

SEQ ID NO:119146-SEQ ID NO:124352 correspond to amino acid sequences predicted to be encoded from the (a) essential and (b) other coding sequences set forth in SEQ ID NO:45569-SEQ ID NO:97729, and are further defined in blocks of sequences corresponding to (c) peptides essential to SCN survival, as set forth in SEQ ID NO:121221-SEQ ID NO:124352, each based on one or more BLASTP relationship to one or more proteins known to be essential to survival of *C. elegans* or other organisms (translated from SEQ ID NO:47644-SEQ ID NO:50775), and (d) other peptides lacking any BLASTP relationship to proteins known in the art, as set forth in SEQ ID NO:119146-SEQ ID NO:121220 (translated from SEQ ID NO:45569-SEQ ID NO:47643).

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The inventors have discovered all or substantially all of the polynucleotide sequences that comprise the genomic DNA obtained from the soybean cyst nematode *Heterodera glycines*, aligned the sequences to derived large blocks of sequence corresponding to genomic contigs set forth herein, analyzed these contigs to identify and characterize untranslated regulatory sequences, for example, promoters, introns, transcriptional initiation sequences, and polyadenylation signals. Genomic polynucleic acid sequences encoding all or part of one or more proteins and characterized as being essential for survival, such as amino acid sequences involved in various metabolic or catabolic biochemical pathways, cell division, reproduction, energy metabolism, digestion, neurological function and the like, are identified in the genomic DNA sequences disclosed in the present invention, and regions of such sequences are demonstrated herein as being useful for selection for use in preparing DNA constructs for use in transforming cells, and that also express double stranded RNA molecules from such constructs in the transformed cells, and when provided in the diet of a target pest, whether artificial diet or a natural diet, especially a plant cell, plant tissues or other plant parts, such as leaves, roots, stems, flowers, fruits or seeds, results in the fecundicity, morbidity, and/or mortality of the pest.

As described herein, ingestion by a target nematode pest of compositions containing one or more dsRNA molecules, wherein at least one segment of the dsRNA molecule corresponds to a substantially identical segment of RNA produced in the cells of the nematode, will result in death, growth inhibition, stunting, inhibition of maturation or fecundity of the nematode. These results indicate that a polynucleotide molecule, either DNA or RNA, derived from SCN can be used to design a DNA construct according to the methods of the present invention to express a recombinant gene product in a transgenic host cell. The host cell can be transformed to contain one or more of the polynucleotide molecules derived from sequences disclosed herein. The DNA construct transformed into the host cell transcribes one or more RNA sequences that form into a dsRNA molecule in the cell or biological fluids within the transformed host, thus making the dsRNA available for ingestion by nematode when it feeds upon the transgenic host. Therefore, the transformed host cell now contains within its genome the genetic potential to defend the host cell and its parents, siblings and children from attack by the nematode.

The present invention relates to genetic control of nematode infestations in host organisms. More particularly, the present invention includes the DNA constructs, selection of target polynucleotides and methods for delivery of nematode control agents to a nematode. The present invention provides methods for employing stabilized dsRNA molecules in the diet of the nematode as a means for suppression of targeted genes in the nematode, thus achieving desired control of nematode infestations in, or about the host or symbiont targeted by the nematode. The preferred host is a plant wherein the plant is transformed with a recombinant DNA construct that expresses recombinant stabilized dsRNA, siRNA, and/or miRNA molecules. The recombinant DNA construct comprises a nucleotide sequence that is transcribed into RNA by the host cell. The term "recombinant DNA" or "recombinant nucleotide sequence" refers to DNA that contains a genetically engineered modification through manipulation as a result of methods for mutagenesis, use of restriction enzymes, and thermal amplification methods, and the like.

The dsRNA molecules, siRNA molecules, and/or miRNA molecules of the present invention are homologous or complementary to at least about a contiguous 17-21 nucleotide sequence selected from the group consisting of SEQ ID NO:45569 through SEQ ID NO:97729. Isolated and purified nucleotide sequences from a SCN are provided from a genomic library constructed from polynucleotide sequences of the pest. The ingestion of such nucleotide sequences results in the reduction or elimination of an essential gene product necessary for the nematode's growth and development or other biological function.

The present invention also contemplates a transformed plant cell and transformed plants and their progeny. The transformed plant cells and transformed plants express one or more of the dsRNA, siRNA, or miRNA sequences of the present invention from one or more of the DNA sequences as set forth in SEQ ID NO:1-SEQ ID NO:45568 and SEQ ID NO:45569 through SEQ ID NO:97729, or the complement thereof.

As used herein the words "gene suppression", when taken together, are intended to refer to any method for reducing the levels of a gene product as a result of gene transcription to mRNA. Gene suppression is also intended to mean the reduction of protein expression from a gene or a coding sequence including posttranscriptional gene suppression and transcriptional suppression. Posttranscriptional gene suppression is intended to refer to that suppression mediated by the homology between all or a part of an RNA transcript transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is referred to as co-suppression, in the anti-sense orientation to effect what is referred to as anti-sense suppression, or in both orientations producing a dsRNA to effect what is referred to as RNA interference (RNAi). Transcriptional suppression is intended to refer to that suppression mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant nematodes that may ingest or contact plant material containing gene suppression agents, specifically designed to inhibit or suppress the expression of one or more homologous or complementary sequences in the cells of a nematode or other pest.

Post-transcriptional gene suppression by anti-sense or sense oriented RNA to regulate gene expression in plant cells is disclosed in U.S. Pat. Nos. 5,107,065, 5,759,829, 5,283,184, and 5,231,020. The use of dsRNA to suppress genes in plants is disclosed in WO 99/53050, WO 99/49029, U.S. Patent Application Publication 2003/0175965 A1, and 2003/0061626 A1, U.S. patent application Ser. No. 10/465,800, and U.S. Pat. Nos. 6,506,559, and 6,326,193.

A preferred method of post transcriptional gene suppression in plants employs both sense-oriented and anti-sense-oriented, transcribed RNA, which is stabilized, e.g., as a hairpin and stem and loop structure. A preferred DNA construct for effecting post-transcriptional gene suppression is one in which a first segment transcribes an RNA molecule in an anti-sense orientation relative to the mRNA of the gene transcript targeted for suppression, the first segment further linked to a second segment spacer region that is not homologous or complementary to the first segment, and linked to a third segment that transcribes an RNA, wherein a portion is substantially complementarity to the first segment. Such a construct would be expected to form a stem and loop structure by hybridization of the first segment with the third segment and a loop structure forms comprising the second segment (WO94/01550, WO98/05770, US 2002/0048814A1, and US 2003/0018993A1).

As used herein, the term "nucleic acid", "polynucleic acid", or "polynucleotide" refers to a single or double-stranded polymer of deoxyribonucleotide or ribonucleotide bases (also referred to as nucleotides) read from the 5' to the 3' end. The polynucleic acid may optionally contain non-naturally occurring or altered nucleotide bases that permit correct read through by a polymerase. The term "nucleotide sequence" or "polynucleic acid sequence" may refer to both the sense and antisense strands of a polynucleic acid molecule as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes genomic sequences, ribosomal RNA sequences, transfer RNA sequences, messenger RNA sequences, operon sequences and smaller engineered nucleotide sequences or portions thereof that control or affect the expression of a gene product or that may be adapted to express proteins, polypeptides or peptides. A polynucleic acid may optionally contain naturally occurring or altered nucleotide bases that prevent polymerization by a first polymerase copying the strand that contains such base(s), i.e., one or more bases that cannot be templated by the first polymerase while polymerizing the nascent or growing strand, so that any nucleotide sequence extending beyond the non-templated base(s) results in a cohesive end that can be used to link the polynucleic acid to one or more other nucleic acid sequences linked to the complement of the cohesive end, resulting in a chimeric nucleotide sequence. The naturally occurring or altered nucleotide base(s) can then be templated to link the fragments comprising the chimeric nucleotide sequence by exposing the chimera to a second polymerase that recognizes the naturally occurring or altered nucleotide base(s) and copies that/those base(s) with fidelity (Jarrell et al. U.S. Pat. No. 6,358,712; Newton et al. 1993 21:1155-1162). This method may be particularly useful when assembling multi-component sequences for expression of an RNA sequence that folds into a dsRNA sequence and functions to suppress one or more genes in one or more target organisms.

As used herein, the term "nematode" refers to plant parasitic nematodes, in particular to members of the Tylenchoidea superfamily, and more specifically to the Heteroderidae family of nematodes that include the cyst nematodes (including at least Heterodera and Globodera species) and the rootknot nematodes (Meloidogyne species). More specifically to Heterodera species and even more specifically to Heterodera glycines, the soybean cyst nematode. Nematode species that were shown to have homologous target sequences with H. glycines polynucleotides of the present invention were: rootknot nematode species—Meloidogyne species such as M. arenaria, M. chitwoodi, M. artiellia, M. fallax, M. hapla, M. javanica, M. incognita, M. microtyla, M. partityla, M. panyuensis, and M. paranaensis; cyst nematode species—Heterodera species such as H. schachtii, Globodera species such as G. rostochiensis, G. pallida, and G. tabacum, Heterodera species such as H. trifolii, H. medicaginis, H. ciceri, H. mediterranea, H. cyperi, H. salixophila, H. zeae, H. goettingiana, H. riparia, H. humuli, H. latipons, H. sorghi, H. fici, H. litoralis, and H. turcomanica; lesion nematode species—Pratylenchus species such as P. scribneri, P. magnica, P. thornei, P. crenatus, P. brachyrus, P. vulnus, P. penetrans, P. coffeae, and P. neglectus; other plant parasitic nematode species include: Hirschmanniella species, Radopholus species such as R. similis, and Pratylenchoid magnicauda. Animal intestinal parasitic nematode species for which polynucleotides have been identified as a result of comparisons to the sequence data disclosed herein include Ascaris lumbricoides, and Ascaris suum.

As used herein, a "pest resistance" trait is a characteristic of a transgenic plant, transgenic animal, transgenic host or transgenic symbiont that causes the plant, animal, host, or symbiont to be resistant to attack from a pest that typically is capable of inflicting damage or loss to the plant, animal, host or symbiont. Such pest resistance can arise from a natural genetic variation or more typically from incorporation of recombinant DNA that confers pest resistance. Fire et al. (U.S. Pat. No. 6,506,599) generically described inhibition of pest infestation, and demonstrated gene suppression in the non-pest nematode species Caenorhabditis elegans. Similarly, Plaetinck et al. (US 2003/0061626A1) suggests using dsRNA to inhibit gene function in a variety of nematode pests. Mesa et al. (US 2003/0150017A1) describe using DNA sequences to transform host cells to express dsRNA sequences that are substantially identical to target sequences in specific pathogens, and particularly describe constructing recombinant plants expressing such dsRNA sequences for ingestion by various plant pests, facilitating down-regulation of a gene in the genome of the pest, and improving the resistance of the plant to the pest infestation. As used herein, the term "expression" refers to the transcription and stable accumulation of a nucleotide sequence comprising both sense and antisense RNA derived from the nucleic acid sequences disclosed in the present invention, whether or not the RNA sequence is capped, spliced, and polyadenylated and trafficked into the cytoplasm of the cell. Expression may also refer to translation of mRNA into a polypeptide or protein. As used herein, the term "sense" RNA refers to an RNA transcript corresponding to a sequence or segment that, when produced by the target nematode, is in the form of a mRNA that is capable of being translated into polypeptide by the target nematode cell. As used herein, the term "antisense RNA" refers to an RNA transcript that is complementary to all or a part of a mRNA that is normally produced in a cell of a nematode. The complementarity of an antisense RNA may be with any part of the specific gene transcript, i.e., at the 5' non-coding sequence, 3' non-translated sequence, introns, or the coding sequence. As used herein, the term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

Exposure of a plant cyst forming nematode to the dsRNA, siRNA, or miRNA sequences of the present invention may occur during the nematodes' juvenile J2, J3, J4, adult female or adult male developmental stages. Exposure may occur as the J2 or male nematode is migrating through the plant vasculature, for example the cortical cells, or during or after establishment of a feeding site within syncytial cells. Exposure may occur by the production of the dsRNA in neighboring transfer-like cells with movement into the feeding site. dsRNA, siRNA, or miRNA may enter the nematode through a variety of means including, for example, through the stylet and pharnyx, the anus, the extratory duct, or amphidial and phasmid channels. dsRNA produced in the tissues of the feeding site may enter the nematode by transport through the feeding tube (Hussey, R S and Grundler et. al., 1998, Nematode parasitism of plants, Ch. 9, *The Physiology and Biochemistry of Free-living and Plant-parasitic Nematodes*, eds R N Perry and D J Wright), directly from the cytoplasm, from extracellular regions, or from other plant compartments. Movement of dsRNA, siRNA, or miRNA into the nematode may require that the RNA exhibit a molecular weight of less than or substantially less than 25 Kda (feeding tube size threshold). Creating an siRNA or miRNA in the plant that is bioavailable to the nematode may require preventing the siRNA from entering or remaining within the plant RISC complex, a protein complex well in excess of 25 KD. For example, this may be accomplished through a number of means such as (1) by co-expressing a small RNA-binding protein that exhibits a greater affinity for the plant RISC complex compared to the nematode specific siRNA, (2) by producing in the transgenic cell a nematode specific siRNA that is incompatible with the plant RISC complex yet functional in the nematode RISC complex, or (3) by down-regulating RISC complex expression in the feeding site established by the nematode. Small RNA-binding proteins may be optimized for binding to a specific siRNA or miRNA by modifying amino acid residues by phage display or other peptide selection methods.

As used herein, the phrase "inhibition of gene expression" or "inhibiting expression of a target gene in the cell of a nematode" may refer to the absence (or observable decrease) in the level of protein and/or mRNA product from the target gene. In the event that a particular transcript or translation product is not detectable, whether or not the lack of detection is a result of the expression of a dsRNA specifically designed to suppress the levels of such transcript or translation product, the phrase "inhibition of gene expression" or "inhibiting expression of a target gene in the cell of a nematode" may refer to the observation of a phenotypic effect or the lack thereof within the plant or within or about the target pest that feeds upon the transgenic plant. Specificity refers to the ability to inhibit the target gene without manifest effects on other genes of the cell and without any effects on any gene within the cell that is producing the dsRNA molecule. The inhibition of gene expression of one or more target genes in the nematode may result in novel phenotypic traits in the nematode.

Without limiting the scope of the present invention, there is provided, in one aspect, a method for controlling plant infestation by a nematode or other plant pest using stabilized dsRNA strategies. The method involves generating stabilized dsRNA molecules as one type of nematode control agents, that when provided in the diet of the nematode, induce gene silencing. As used herein, the phrase "generating a stabilized dsRNA molecule" refers to the methods of employing recombinant DNA technologies to construct a DNA nucleotide sequence that transcribes a stabilized dsRNA. As used herein, the term "silencing" refers the effective "down-regulation" of expression of one or more targeted nucleotide sequences within one or more cells of a nematode or other plant pest and, hence, the elimination of the ability of the targeted nucleotide sequence(s) to cause its normal effect within the cell.

The present invention also provides in part a delivery system for providing a nematode control agent to a nematode through exposure of the nematode to a host, such as a plant containing the one or more control agents of the present invention by ingestion of the plants' cells or the contents of those cells. One embodiment of the present invention provides for generating a transgenic plant cell or a plant that contains a recombinant DNA construct transcribing the stabilized dsRNA molecules of the present invention. As used herein, the phrase "generating a transgenic plant cell or a plant" refers to the methods of employing recombinant DNA technologies to construct a plant transformation vector transcribing the stabilized dsRNA molecules of the present invention, to transform a plant cell or a plant with such vector, and to generate the transformed plant cell or transgenic plant containing a part of the vector that transcribes the stabilized dsRNA molecules. In particular, the method of the present invention may comprise a recombinant DNA construct in a cell of a plant that results in dsRNA transcripts that are substantially homologous to an RNA sequence expressed by a nucleotide sequence contained within the genome of a nematode. Where the nucleotide sequence within the genome of a nematode comprises a gene essential to the viability and infectivity of the nematode, its down-regulation results in a reduced capability of the nematode to survive and/or infect and/or cause damage to host cells. Hence, such down-regulation results in a "deleterious effect" on the maintenance, viability, and infectivity of the nematode, in that it prevents or reduces the nematode's ability to feed off of and survive on nutrients derived from the host cells. By virtue of this reduction in the nematode's viability and infectivity, resistance and/or enhanced tolerance to infection by a nematode or other plant pest is facilitated in the cells of a plant.

It is envisioned that the compositions of the present invention can be incorporated within the seeds of a plant species either as a product of expression from a recombinant gene incorporated into the genome of the plant cells, or incorporated into a coating or seed treatment that is applied to the seed before planting. A plant derived from a single plant cell transformed to contain a recombinant or heterologous gene is considered herein to be a transgenic event.

The present invention also includes seeds and plants having more that one agronomically important trait. Such combinations are referred to as "stacked" traits. These stacked traits can include a combination of traits that are directed at the same target nematode pest, or they can be directed at different target nematode pests, or to one or more insect pests, or can provide herbicide tolerance to the plant, for example tolerance to glyphosate herbicide. The stacked traits can be achieved by breeding to plants that have the trait or by building a chimeric DNA construct that contains multiple plant expression cassettes and transforming the expression cassettes into the genome of the plant.

Cells of a plant seed of the present invention may express one or more dsRNA's, the sequence of any one of which is derived from a target sequence, i.e., a nematode specific sequence disclosed herein in SEQ ID NO:1-SEQ ID NO:45569, and also may express a nucleotide sequence that provides herbicide tolerance, for example, resistance to glyphosate, N-(phosphonomethyl) glycine, including the isopropylamine salt form of such herbicide. Herbicides for which transgenic plant tolerance has been demonstrated include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase, bromoxynil nitrilase, phytoene desaturase, norflurazon, acetohydroxyacid synthase and the bar gene for tolerance to glufosinate and bialaphos (U.S. Pat. Nos. 5,627,061, 5,633,435, 6,040,497, 5,094,945, and 4,810,648).

As used herein, the term "pest control agent", or "gene suppression agent" refers to one or more particular RNA molecules consisting of a first RNA segment and a second RNA segment that are complimentary to each other and are linked by a third RNA segment. The complementarity between the first and the second RNA segments results in the ability of the two segments to hybridize in vivo and in vitro to form a double stranded molecule, i.e., a stem comprising the first and the second segments linked together by the third segment which forms a loop between the first and second segments, so that the entire structure forms into a stem and loop structure. Structures consisting of a first and a second segment that hybridize more tightly to each other may form into a stem-loop knotted structure. The first and the second segments, when hybridized together, correspond invariably, and not respectively, to a sense and an antisense sequence with respect to the target RNA transcribed from the target gene in the target nematode that is suppressed by the ingestion of the dsRNA molecule, or ingestion of an siRNA molecule derived from the dsRNA molecule. The pest control agent can also be a substantially purified (or isolated) nucleic acid molecule and more specifically nucleic acid molecules or nucleic acid fragment molecules thereof from a genomic DNA (gDNA) or cDNA library. Such substantially purified molecules can be applied to a seed, whether a seed from a transgenic plant or otherwise, in the form of a seed treatment, together with a pharmaceutically acceptable carrier for stabilizing the dsRNA molecules, resulting in the dsRNA being bioavailable within a plant grown from the seed, or bioavailability within the rhizosphere of the root system of the plant grown from the seed. A seed may be treated with one or more agents, each exhibiting different activities designed to provide the seed, the germinating seedling, and the growing plant or root with one or more advantages in comparison to other plants, such as pest resistance, including bacterial, fungal, and nematode resistance, fertilizers, growth stimulants, gene stimulants or suppressors, herbicide functions to which the seed, germ, and or roots and seedling are resistant, and the like. Alternatively, the fragments may comprise smaller dsRNA oligonucleotides comprising from about 15 to about 750 or more consecutive nucleotides selected from the group consisting of SEQ ID NO:1-SEQ ID NO:45569 and the complements thereof, or from about 15 to about 30 nucleotides, or from about 21 to about 24 consecutive nucleotides. The pest control agent may also refer to a DNA construct that comprises the polynucleic acid molecules or nucleic acid fragment molecules of the present invention and the DNA construct is a transgene incorporated into the genome of a host cell. The pest control agent may further refer to a plant comprising such a DNA construct in its genome or in the genome of a subcellular organelle that comprises the polynucleic acid molecules or nucleic acid fragment molecules described in the present invention. The method of the present invention provides for the production of a dsRNA transcript, the nucleotide sequence of which is substantially homologous to a targeted RNA sequence encoded by a target nucleotide sequence within the genome of a target pest.

As used herein, the term "genome" as it applies to cells of a nematode, a plant pest, or a host encompasses not only chromosomal DNA found within the nucleus, but organelle DNA found within subcellular components of the cell. The sequences of the present invention, when introduced into plant cells, can therefore be either chromosomally integrated or organelle-localized. The term "genome" as it applies to bacteria encompasses both the chromosome and plasmids within a bacterial host cell. The DNA's of the present invention introduced into bacterial host cells can therefore be either chromosomally integrated, localized to a plasmid, or to a viral vector capable of replication in the bacterial host.

In certain preferred embodiments expression of the gene targeted for suppression in the plant pest is inhibited by at least about 10%, at least about 33%, at least about 50%, at least about 80%, at least about 90%, at least about 95%, or by at least about 99% or more within cells of the nematode so a significant inhibition takes place. Significant inhibition is intended to refer to inhibition sufficient to result in a detectable phenotype (e.g., cessation of growth, paralysis, sterility, behavioral effects, second generation effects, effects observed on nematodes ingesting dsRNA or on their progeny, morbidity, or mortality, etc.) or a detectable decrease in RNA and/or protein corresponding to the target gene being inhibited. Although in certain embodiments of the invention inhibition occurs in substantially all cells of the nematode, in other preferred embodiments inhibition occurs in only a subset of cells that are contacted with the dsRNA, or that are expressing the target gene transcript.

The advantages of the present invention may include, but are not limited to the ease of introducing dsRNA into the nematode or other pest cells, the low concentration of dsRNA, siRNA, or miRNA which can be used, the stability of dsRNA, siRNA, or miRNA and the effectiveness of the inhibition. The present invention provides a method for selecting polynucleotide sequences of a target gene sequence and is not limited to in vitro use of specific sequence compositions identified by the method or to the set of exemplary target genes of the present invention. Segments of the nucleotide sequences of the present invention may be selected for their level of gene inhibition/suppression by scanning segments of the *H. glycines* sequences to identify segments that exhibit preferred levels of gene suppression or pest inhibition when provided as a dsRNA molecule in the diet of one or more target pests such as *H. glycines*.

As used herein, the term "sequence identity", "sequence similarity" or "homology" is used to describe sequence relationships between two or more nucleotide or amino acid sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage identity of a reference sequence to another is calculated by determining the number of positions at which the reference sequence (whether nucleic acid or amino acid sequence) is identical to another sequence to yield the number of matched positions, dividing the number of matched positions by the total number of positions in the window of comparison, and multiplying the result by 100 to yield the percentage of sequence identity. A sequence that is identical at every position in comparison to a reference sequence is said to be, with respect to a nucleotide sequence or amino acid sequence, identical to the reference sequence and vice-versa. A first nucleotide sequence when observed in the 5' to 3' direction is said to be the "complement" of, or complementary to, a second or reference nucleotide sequence observed in the 3' to 5' direction if the reverse complement of the first nucleotide sequence is identical at every nucleotide position with the second or reference sequence. As used herein, two nucleic acid sequence molecules are said to exhibit "complete complementarity" when every nucleotide of one of the sequences, when read 5' to 3', is complementary to every nucleotide of the other sequence when read 3' to 5'. A nucleotide sequence that is complementary to a reference nucleotide sequence will exhibit a sequence identical to the reverse complement sequence of the reference nucleotide sequence.

In practicing the present invention, a target gene may be derived from a nematode or other pest species that causes damage to one or more different crop plants and/or yield losses to such plants. Several criteria may be employed in the selection of target genes. The gene may be one whose protein product has a rapid turnover rate, so that dsRNA inhibition will result in a rapid decrease in protein levels. In certain embodiments it is advantageous to select a gene for which a small decrease in expression level results in deleterious effects for the pest. It may be desirable to target a broad range of nematode species and so a nucleotide sequence is selected that is highly conserved across the targeted range of species. Conversely, for the purpose of conferring specificity, in certain embodiments a nucleotide sequence is selected that contains regions that are poorly conserved between individual targeted pest species, or between the targeted pest and other organisms. In certain embodiments it may be desirable to select a nucleotide sequence that exhibits no known homology to sequences in other organisms. As used herein, the term "derived from" refers to a specified nucleotide sequence that may be obtained from a particular source or species.

Target genes for use in the present invention may include, for example, those that play important roles in the viability, growth, development, reproduction and infectivity of a particular pest. These target genes may be one or more of any house keeping gene, transcription factor and pest specific gene that provides an observable phenotype, in particular a phenotype that results in the suppression of feeding on or the inability to utilize a transgenic soybean plant expressing a SCN derived dsRNA as a nutrient source. For example, target genes that are anticipated herein to be effective in producing such phenotypes are similar to those that have been shown to affect the viability, growth, development, mobility, neurological stimulation, muscular function, and reproduction in *C. elegans*, including but not limited to the following phenotypes: (Adl) adult lethal, (Age), (Bli) blistered, (Bmd) body morphology defect, (Ced) Cell death abnormality, (Clr) clear, (Daf) DAuer Formation, (Dpy) dumpy, (Egl) egg laying defect, (Emb) embryonic lethal, (Evl) everted vulva, (Fem) feminization of XX and XO animals, (Fgc) Fewer Germ Cells, (Fog) feminization of germline, (Gon) GONad development abnormal, (Gro) slow growth, (Him) high incidence of male progeny, (Hya) HYperActive, (Let) larval lethal, (Lin) lineage abnormal, (Lon) long body, (Lpd), (Lva) larval arrest, (Lvl) larval lethal, (Mab) Male ABnormal, (Mei) Defective meiosis, (Mig) MIGration of cells abnormal, (Mlt) molt defect, (Morphology), (Mut) Mutator, (Muv) MUlti-Vulva, (Oma) Oocyte MAturation defective, (Pat) Paralyzed, Arrested elongation at Two-fold, (Pch) PatCHy coloration, (Pnm) Pronuclear migration alteration in early embryo, (Prl) paralyzed, (Prz) PaRaLyzed, (Pvl) protruding vulva, (Pvu) protruding vulva, (Rde), (Reproductive), (Rol) roller, (Rot) centrosome pair and associated pronuclear rotation abnormal, (Rup) exploded, (Sck) sick, (Sle) Slow embryonic development, (Slu) SLUggish, (Sma) small, (Spd) SpinDle, abnormal embryonic, (Spo) Abnormal embryonic spindle position and orientation, (Ste) sterile, (Stp) sterile progeny, (Unc) uncoordinated, (Unclassified), (Vul) vulvaless, (WT), (defect) morphological or behavioral defects. SCN genome sequences predicted to encode various gene products set forth herein annotated to the *C. elegans* specific genes previously shown to exert a negative effect or observable phenotype in *Drosophila* or in *C. elegans* are anticipated to be effective targets for achieving a similar phenotype when expressed in planta as a dsRNA for the purpose of suppressing a gene in SCN specifically targeted by the dsRNA. Gene sequences unique to SCN and not annotated to sequences or gene products from other organisms are also anticipated to be effective for achieving control of SCN when such sequences are provided in the diet of the SCN as a dsRNA because the target genes are unique to SCN pest metabolism, physiology, and pathogenicity.

DNA segments of the present invention are desired for use in constructing dsRNA expression sequences, particularly if the DNA segments exhibit at least from about 70% identity, or at least from about 75% identity, or at least from about 80% identity, or at least from about 90% identity, or at least from about 95% identity, or at least from about 98% identity, or at least about 100% identity to contiguous 17-24 nucleotide sequences found within the nematode genome or other pest sequences targeted for suppression. Sequences less than about 80% identical to a target gene are anticipated to be less effective and so less desirable. Inhibition is specific to the nematodes' gene or gene families, the sequence of which corresponds substantially to the dsRNA. Expression of unrelated genes is not affected. This specificity allows the selective targeting of a nematode or other pest species, resulting in the absence of an effect on non-target organisms exposed to the compositions of the present invention.

The regions predicted to be more effective at dsRNA-mediated gene silencing include regions that exhibit higher siRNA efficiency. Higher siRNA efficiency may be achieved by any technique, including, but not limited to, computational methods such as algorithms designed to predict siRNA efficiency based on thermodynamic characteristics of a given dsRNA (or DNA) sequence, generally considering sequences of from about 17, to about 18, to about 19, to about 20, to about 21, to about 22, to about 23, or even to about 24 contiguous nucleotides corresponding to a sequence that is being targeted for suppression (Schwarz et al., 200, Cell 115:199-208; Chalk et al. 2004, Biochem. Biophys. Res. Comm. 319:264-274; Ui-Tei et al., NAR 2004, 32:936-948; Reynolds et al., 2004, Nature Biotechnology 22:326-330).

Inhibition of a target gene using the stabilized dsRNA technology of the present invention is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence are also effective for gene specific inhibition. In performance of the present invention, it is preferred that the inhibitory dsRNA and the portion of the target gene share at least from about 75% sequence identity, or from about 80% sequence identity, or from about 90% sequence identity, or from about 95% sequence identity, or from about 99% sequence identity, or even about 100% sequence identity. Alternatively, the duplex region of the RNA may be defined functionally as a nucleotide sequence that hybridizes with a portion of the target gene transcript. A greater sequence homology across a target gene sequence that is less than full-length in comparison to the target gene compensates for a less homologous sequence that more closely approximates the full length of the target gene. The length of a nucleotide sequence that is identical to a portion of the target gene sequence can be from about 21, to about 25, to about 50, to about 100, to about 200, to about 300, or more contiguous bases. Normally, a sequence of greater than 20-100 nucleotides is preferable, although a sequence of greater than about 200-300 nucleotides may be preferred, depending on the length of the target gene. The invention has the advantage of being able to tolerate sequence variations due to genetic mutation, strain polymorphism, or evolutionary divergence. Therefore the nucleic acid molecule introduced into a plant for expression as a pest specific dsRNA gene suppression construct may not need to exhibit absolute homology, and may not need to represent the full length of the sequence targeted for suppression.

The dsRNA molecules may be synthesized either in vivo or in vitro. The dsRNA may be formed by a single self-complementary RNA strand or two complementary RNA strands expressed from separate expression constructs. Endogenous RNA polymerase of the cell may mediate transcription in vivo, or cloned RNA polymerase can be used for transcription in vivo or in vitro. Inhibition may be achieved by specific transcription in an organ, tissue, or cell type; stimulation of an environmental condition (e.g., infection, stress, temperature, chemical inducers); and/or engineering transcription at a developmental stage or age of the transgenic plant expressing the dsRNA construct. The RNA sequences expressed from the recombinant construct may or may not be polyadenylated. The RNA sequences expressed from the recombinant construct may or may not be capable of being translated into a polypeptide by a cell's translational apparatus.

The RNA, dsRNA, siRNA, or miRNA of the present invention intended for use in controlling plant pest infestation may be produced chemically or enzymatically through manual or automated reactions or in vivo in an organism other than the plant for which pest control is intended. RNA may also be produced by partial or total organic synthesis. Any modified ribonucleotide can be introduced by in vitro enzymatic or organic synthesis. The RNA may be synthesized by a cellular RNA polymerase or a bacteriophage RNA polymerase (e.g., T3, T7, SP6). If synthesized chemically or by in vitro enzymatic synthesis, the RNA may be purified prior to introduction into the cell or formulated in an agronomically acceptable carrier and applied to the soil, to the roots, or to the seed prior to planting. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

For transcription from a transgene in vivo or from an expression cassette, a regulatory region (e.g., promoter, enhancer, silencer, leader, intron and polyadenylation) may be used to modulate the transcription of the RNA strand (or strands). Therefore, in one embodiment, the polynucleotide sequences constructed to facilitate transcription of the RNA molecules of the present invention are operably linked to one or more promoter sequences functional in a plant host. The polynucleotide sequences may be placed under the control of an endogenous promoter normally present in the host genome. The polynucleotide sequences of the present invention, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct. The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

In another embodiment, the nucleotide sequence of the present invention comprises an inverted repeat sequence separated by a spacer sequence. The spacer sequence may be a region comprising any sequence of nucleotides that facilitates secondary structure formation between the inverted repeat sequences. In one embodiment, the spacer sequence is part of the sense or antisense polynucleotide sequence for mRNA. The spacer sequence may alternatively comprise any combination of nucleotides or homologues thereof that are capable of being linked covalently to a nucleic acid molecule. The spacer sequence may comprise a contiguous sequence of nucleotides of from about 8-100 nucleotides in length, or alternatively from about 100-200 nucleotides in length, or from about 200-400 nucleotides in length, or from about 400-500 nucleotides in length, or from about 500 to about 1500 nucleotides in length.

The gene or genes targeted for suppression may be amplified using any thermal amplification means and the precise nucleotide sequence determined. One skilled in the art is able to modify the thermal amplification conditions in order to ensure optimal amplicon product formation, and the amplicon may be used as a template for in vitro transcription to generate sense and antisense RNA with the included minimal promoters.

As used herein, the phrase "a substantially purified nucleic acid", "an artificial sequence", "an isolated and substantially purified nucleic acid", or "an isolated and substantially purified nucleotide sequence", with respect to a naturally occurring nucleotide sequence, refers to a nucleic acid molecule that is substantially removed from the composition with which it is associated in its natural state. Examples of a substantially purified nucleic acid molecule include: (1) a DNA sequence comprising the contiguous sequence at least about 17, or about 18, or about 19 or more nucleotides in length consisting of a portion of a naturally occurring DNA molecule, but which is not flanked by polynucleotide sequences occur naturally on either end of the contiguous sequence; (2) a nucleic acid molecule comprising a naturally occurring contiguous nucleotide sequence isolated from its naturally occurring state and incorporated into a DNA construct; (3) a cDNA, a genomic DNA fragment isolated and purified substantially from all other genomic DNA to which it was originally naturally associated, an amplicon fragment produced using thermal amplification procedures, or a restriction fragment; (4) recombinant DNA; and (5) synthetic DNA. A substantially purified nucleic acid may also be comprised of one or more segments of any of the sequences referred to hereinabove.

Nucleic acid molecules, fragments thereof, and complements thereof selected from the group consisting of SEQ ID NO:1-45568 may be employed as probes or primers to identify related nucleic acid molecules from other species for use in the present invention to produce desired dsRNA, siRNA, and miRNA molecules. Such related nucleic acid molecules include the nucleic acid molecules that encode the complete amino acid sequence of a protein, and the promoters and flanking sequences of such molecules. In addition, such related nucleic acid molecules include nucleic acid molecules that encode gene family members. Such molecules can be readily obtained by using the above-described nucleic acid molecules or fragments thereof to screen complementary DNA or genomic DNA libraries obtained from a nematode or other plant pest species. The screen can be any physical means such as northern, southern, or any immunologically based screening method that detects either the specific sequence of a nucleotide molecule, or the transcribed and/or translated product of such nucleotide molecule, or any mathematical algorithm that is used for comparing nucleotide sequences in silico.

Nucleic acid molecules, fragments thereof, and complements thereof selected from the group consisting of SEQ ID NO:45569-SEQ ID NO:97729 may also be used in a similar fashion to screen other genomes, libraries, and organisms for related sequences. Such related sequences are expected to include but not be limited to homologues that include nucleic acid molecules that encode, in whole or in part, protein homologues of other pest species, plants or other organisms. Such molecules can be readily obtained by using the above-described nucleic acid molecules or fragments thereof to screen EST, cDNA or gDNA libraries. Such homologous molecules may differ in their nucleotide sequences from those found in one or more of SEQ ID NO:1-SEQ ID NO:45568 and SEQ ID NO:45569 through SEQ ID NO:97729 or complements thereof, because perfect complementarity is not required for such related sequences to hybridize to each other. In a particular embodiment, methods for 3' or 5' RACE may be used to obtain such sequences (Frohman, M. A. et al., *Proc. Natl. Acad. Sci.* (*U.S.A.*) 85:8998-9002, 1988; Ohara, O. et al., *Proc. Natl. Acad. Sci.* (*U.S.A.*) 86:5673-5677, 1989). In general, any of the above described nucleic acid molecules or fragments may be used to generate dsRNA's, siRNA's, and/or siRNA's that are suitable for use in a diet, in a spray-on mix, or in a recombinant DNA construct of the present invention.

As used herein, the phrase "coding sequence", "structural nucleotide sequence" or "structural nucleic acid molecule" refers to a polynucleotide molecule that is translated into a polypeptide when placed under the control of appropriate regulatory sequences. The structural nucleotide sequence, coding sequence, or structural nucleic acid molecule can be referred to using other terms in the art, but is intended to include DNA as well as RNA molecules. A coding sequence can include, but is not limited to, genomic DNA sequences or portions thereof identified to encode or to be capable of encoding a polypeptide, a cDNA produced as a result of reverse transcription of mRNA that has been purified substantially because if its ability to hybridize to a polyT sequence, expressed sequence tagged (EST) sequences, and recombinant nucleotide sequences produced specifically for expression of a protein sequence.

Two molecules are said to be "minimally complementary" if they can hybridize to one another with sufficient stability to permit them to remain annealed to one another under at least conventional "low-stringency" conditions. Similarly, the molecules are said to be complementary if they can hybridize to one another with sufficient stability to permit them to remain annealed to one another under conventional "high-stringency" conditions. Conventional stringency conditions are described by Sambrook, et al., (1985). Appropriate stringency conditions which promotes hybridization of two different nucleic acid sequences are, for example, incubation of the two sequences together in 6.0× sodium chloride/sodium citrate (SSC) at about 45° C. where one of the two different sequences is tethered in some fashion to a solid support and the untethered sequence is linked to a reporter molecule such as a ligand that can be detected using an immunological means, a fluorophores, a radioisotope, or an enzyme. The hybridization of the two sequences under the above conditions can be followed by a wash in 2.0×SSC at 50° C. to remove any excess reagents or unbound or unhybridized probe or untethered molecules (*Current Protocols in Molecular Biology*, John Wiley & Sons, N.Y. (1989), 6.3.1-6.3.6). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature (about 22° C.) to high stringency conditions (about 65° C.). Temperature and salt may be varied together or independent of each other.

A nucleic acid for use in the present invention may specifically hybridize to one or more of nucleic acid molecules from nematodes or complements thereof under moderately stringent conditions, for example at about 2.0×SSC and about 65° C. A nucleic acid for use in the present invention will include those nucleic acid molecules that specifically hybridize to one or more of the nucleic acid molecules disclosed therein as set forth in SEQ ID NO:1 through SEQ ID NO:47643 or complements thereof under high stringency conditions. Preferably, a nucleic acid for use in the present invention will exhibit at least from about 70%, at least from about 80%, at least from about 90%, at least from about 95%, at least from about 98% or even about 100% sequence identity with one or more nucleic acid molecules as set forth in SEQ ID NO:45569 through SEQ ID NO:47643.

Nucleic acids of the present invention may be entirely synthetically constructed or assembled piecemeal from naturally occurring or combinations of naturally occurring and synthetic components. All or any portion of the nucleic acids of the present invention may be synthesized without reference to codon usage calculated for any particular plant species, however when a particular sequence is intended to be effective in suppression of one or more genes in one or more pest species, it is preferable that the sequence be selected such that the sequence in any gene or species targeted for suppression be entirely or substantially entirely identical or entirely or substantially entirely complementary to the suppressor sequence.

The present invention also relates to recombinant DNA constructs for expression in a microorganism. Heterologous nucleic acids from which an RNA of interest is transcribed can be introduced into a microbial host cell, such as a bacterial cell or a fungal cell, in order to produce quantities of double stranded RNA for use in suppression of one or more genes in one or more plant pests.

The present invention also contemplates transformation of a polynucleotide sequence of the present invention into a plant to achieve nematode or other plant pest inhibitory levels of expression of one or more dsRNA molecules. A plant transformation vector comprises one or more nucleotide sequences that is/are capable of being transcribed as an RNA molecule and that is/are substantially homologous and/or complementary to one or more nucleotide sequences encoded by the genome of the nematode, or other plant pest, such that upon uptake of the RNA molecule, results in a down-regulation of expression of at least one of the respective nucleotide sequences of the nematode or other plant pest. In one embodiment the plant transformation vector is an isolated and purified DNA molecule comprising a promoter operatively linked to a contiguous nucleotide sequence comprising one or more polynucleotide molecules of the present invention selected from the group consisting of SEQ ID NO:45569 through SEQ ID NO:50775. The polynucleotide molecule includes a segment comprising all or part of a RNA molecule complementary to a targeted RNA within a nematode or pest cell, and may also contain a functional intron sequence positioned either upstream of or within the transcribed RNA sequence, and may also contain a five prime (5') untranslated leader sequence (i.e., a UTR or 5'-UTR) positioned between the promoter and the point of transcription initiation.

A plant transformation vector may contain sequences for suppression of more than one gene, thus allowing production of more than one dsRNA for inhibiting expression of two or more genes. One skilled in the art will readily appreciate that segments of DNA whose sequence corresponds to that present in different genes can be combined into a single composite DNA segment for expression in a transgenic plant to achieve suppression of one or more nematode or pest genes, one or more plant genes, or a combination thereof. Alternatively, a plasmid of the present invention already containing at least one DNA segment can be modified by the sequential insertion of additional DNA segments between an enhancer and/or promoter and the terminator sequences. A nematode or other plant pest control agent of the present invention may be designed for the inhibition of multiple genes, and the genes to be inhibited can be obtained from the same nematode or other plant pest species in order to enhance the effectiveness of the pest control agent, or from different races/variants of the same pest species, or from different pest species or other organisms. In certain embodiments, the genes derived from different nematodes or other plant pests provide for a broadening of the range of nematodes and other plant pests against which the pest control agent is effective. When multiple genes in one pest are targeted for suppression, a polycistronic DNA element can be fabricated (Fillatti, US Patent Application Publication No. US 2004-0029283 A1).

A promoter that drives expression of a polynucleotide sequence in a particular species of plant is selected for use in expression constructs in which a nucleotide sequence of the present invention is to be used to transform a plant. Promoters that function in different plant species are known in the art. Promoters useful for expression of polypeptides in plants are those that are inducible, viral, synthetic, or constitutive as described in Odell et al. (1985 Nature 313:810-812), and/or promoters that are temporally regulated, spatially regulated, and spatio-temporally regulated. For the purpose of the present invention, e.g., for optimum control of species that feed on roots, it is preferable to achieve the highest levels of expression of these genes within the roots of plants. A number of promoters exhibiting root-enhanced levels of expression of operably linked sequences have been identified. (Lu et al., 2000 J. Plant Phys., 156(2):277-283; U.S. Pat. Nos. 5,837, 848 and 6,489,542). Expression of the constructs of the present invention may preferably be from polymerase III promoters as an alternative to conventional polymerase II promoters, and also may be linked to inducible promoters, or heterologous promoters that require heterologous accessory proteins, such as for example, phage T7 promoters and the like. Promoters that are induced as a result of the establishment by a cyst nematode of a feeding site (feeding site specific promoters), and promoters up-regulated by nematode invasion are specifically contemplated for use in the present invention (Gheysen et al., 2002, Ann. Rev. Phytopathol. 40:191-219).

A recombinant DNA vector or construct of the present invention will typically comprise a marker that confers a selectable phenotype on transformed plant cells, and may also be used to select for plants or plant cells that contain the exogenous nucleic acids of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., 1985 Mol. Gen. Genet. 199:183-188) which codes for kanamycin resistance and can be selected for using kanamycin, G418, etc.; a bar gene which codes for bialaphos resistance; a mutant EPSP synthase gene (Hinchee et al., 1988 Bio/Technology 6:915-922) which encodes glyphosate resistance; a nitrilase gene which confers resistance to bromoxynil (Stalker et al., 1988 J. Biol. Chem. 263:6310-6314); a mutant acetolactate synthase gene (ALS) which confers imidazolinone or sulphonylurea resistance (European Patent Application 154,204); an AMPA-acetyltransferase gene for resistance to phosphonates (U.S. Pat. No. 6,448,476), a methotrexate resistant DHFR gene (Thillet et al., 1988 J. Biol. Chem. 263:12500-12508), and compositions for chloroplast or plastid transformation selection (U.S. Pat. Nos. 5,693,507, 5,451,513, and WO 95/24492).

A recombinant vector or construct of the present invention may also include a screenable marker for monitoring expression. Exemplary screenable markers include a β-glucuronidase or uidA gene (GUS) which encodes an enzyme for which various chromogenic substrates are known (Jefferson, Plant Mol. Biol, Rep. 5.387-405, 1987; Jefferson et al., EMBO J. 6:3901-3907, 1987); an R-locus gene, which encodes a product that regulates the production of anthocyanin pigments (red color) in plant tissues (Dellaporta et al., Stadler Symposium 11:263-282, 1988); a β-lactamase gene (Sutcliffe et al., Proc. Natl. Acad. Sci. (U.S.A.) 75:3737-3741, 1978), a gene which encodes an enzyme for which various chromogenic substrates are known (e.g., PADAC, a chromogenic cephalosporin); a luciferase gene (Ow et al., Science 234:856-859, 1986) a xy/E gene (Zukowsky et al., Proc. Natl. Acad. Sci. (U.S.A.) 80:1101-1105, 1983) which encodes a catechol dioxygenase that can convert chromogenic catechols; an α-amylase gene (Ikatu et al., Bio/Technol. 8:241-242, 1990); a tyrosinase gene (Katz et al., J. Gen. Microbiol. 129:2703-2714, 1983) which encodes an enzyme capable of oxidizing tyrosine to DOPA and dopaquinone which in turn condenses to melanin; an α-galactosidase, which catalyzes a chromogenic α-galactose substrate; and a β-galactosidase which catalyzes the conversion of a chromogenic β-galactoside substrate.

In general a functional recombinant DNA is introduced at a non-specific location in a plant genome. In special cases it may be useful to insert a recombinant DNA construct by site-specific integration. Several site-specific recombination systems exist which are known to function implants include cre-lox as disclosed in U.S. Pat. No. 4,959,317 and FLP-FRT as disclosed in U.S. Pat. No. 5,527,695.

Preferred plant transformation vectors include those derived from a Ti plasmid of *Agrobacterium tumefaciens* (e.g. U.S. Pat. Nos. 4,536,475, 4,693,977, 4,886,937, 5,501,967 and European Patent Application No. 0122791). *Agrobacterium rhizogenes* plasmids (or "Ri") are also useful. Other preferred plant transformation vectors include those disclosed, e.g., by Herrera-Estrella (1983 Nature 303:209-213), Bevan (1983 Nature 304:184-187), Klee (1985 Bio/Technol. 3:637-642) and Eur. Pat Appl. No. EP0 120 516.

Methods and compositions for transforming plants by introducing a recombinant DNA construct into a plant genome includes any of a number of methods known in the art. One method for constructing transformed plants is microprojectile bombardment as illustrated in U.S. Pat. No. 5,015, 580 (soy), U.S. Pat. No. 5,550,318 (corn), U.S. Pat. No. 5,538,880 (corn), U.S. Pat. No. 6,153,812 (wheat), U.S. Pat. No. 6,160,208 (corn), U.S. Pat. No. 6,288,312 (rice) and U.S.

Pat. No. 6,399,861 (corn). Another method for constructing transformed plants is *Agrobacterium*-mediated transformation in cotton (U.S. Pat. No. 5,159,135), corn (U.S. Pat. No. 5,591,616), and soy (U.S. Pat. Nos. 5,824,877 & 6,384,301).

The term "transgenic plant cell" or "transgenic plant" refers to a plant cell or a plant that contains an exogenous or heterologous polynucleotide sequence. A transgenic plant also comprises progeny (seeds, and plants and seeds produced from such seeds, etc.) of any generation of such a transgenic plant or a seed of any generation of all such transgenic plants wherein said progeny or seed comprises the exogenous or heterologous polynucleotide sequence. The heterologous or polynucleotide sequence is a DNA molecule that is transcribed into the RNA, sRNA, dsRNA, siRNA, or miRNA or fragment thereof of the present invention.

A transgenic plant formed using *Agrobacterium* mediated transformation methods contains at least a single recombinant DNA sequence inserted into the plant chromosome and is referred to as a transgenic event. Such transgenic plants are referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. F1 seed can be tested using a SNP or related thermal amplification assay that allows distinction between heterozygotes and homozygotes (i.e., a zygosity assay).

Transgenic plants can also be prepared by crossing a first plant having a recombinant DNA construct with a second plant lacking the construct. For example, a recombinant DNA designed for targeting the suppression of a target gene can be introduced into a first plant line to produce a transgenic plant which can be crossed with a second plant line to introgress the recombinant gene suppression DNA into the second plant line. The second plant line may already contain or be later transformed or bred with another transgenic line to contain one or more transgenes that are different from the gene suppression construct being introgressed from the first plant line.

Without intending to be limited to any single embodiment, the nucleotide sequences of the present invention exhibit a wide variety of usefulness. For example, the sequences can be used to synthesize dsRNA molecules either in in vivo or in vitro systems selected for their ability to cause gene suppression and therefore pest inhibition and such moleculed can be expressed in a transgenic plant, applied to the rhizosphere or biosphere of a plant, or applied in a seed coating or treatment for causing gene suppression in a pest. The sequences can be used in kits incorporating methods for detecting DNA, RNA, or siRNA's in a seed, plant, tissue, biological sample, meal, oil, flour, food product, commodity product, and the like. The sequences can be used for detecting the presence of a homologous sequence in a biological sample. The sequences can be used to construct a dsRNA for suppression of a target gene and can be linked to an RNA segment that binds specifically to one or more receptor molecules, bringing the dsRNA segment into close proximity to a membrane surface, and increasing its likelihood of being taken up by a cell which contains a gene that is targeted for suppression by the dsRNA.

In one embodiment, a nucleotide sequence of the present invention can be recorded on one or more computer readable media. As used herein, "computer readable media" refers to any tangible medium of expression that can be read and accessed directly by a computer. Such media include, but are not limited to: magnetic storage media, such as floppy discs, hard discs, and magnetic tape. Optical storage media include physical storage devices such as compact diskettes. Electrical storage media include random access and read only memory devices (RAM and ROM). A skilled artisan can readily appreciate that any of the presently known computer readable mediums can be used to create a manufacture comprising a computer readable medium having recorded thereon one or more sequences of the present invention. These devices can be accessed with a computer and used to perform a search and comparison of any other sequence of like composition (i.e., nucleotide sequences compared to nucleotide sequences, amino acid sequences compared to amino acid sequences, etc) to determine whether and to what extent a similarity or identity is present between the sequences being compared.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available for creating a computer readable medium having recorded thereon one or more sequences of the present invention. The choice of the data storage structure will generally be based on the means chosen to access the stored information. In addition, a variety of data processor programs and formats can be used to store the sequence information of the present invention on computer readable medium. The sequence information can be represented in a word processing text file, formatted in commercially available software such as Word-Perfect, Microsoft Word, or shareware such as Linux, or represented in the form of an ASCII text file, stored in a database application, such as DB2, Sybase, Oracle, or the like. The skilled artisan can readily adapt any number of data processor structuring formats (e.g. text file or database) in order to obtain computer readable medium having recorded thereon the nucleotide sequence information of the present invention.

Computer software is publicly available which allows a skilled artisan to access sequence information provided in a computer readable medium. Software which implements the BLAST (Altschul et al., *J. Mol. Biol.* 215: 403-410, 1990) and BLAZE (Brutlag, et al., *Comp. Chem.* 17: 203-207, 1993) search algorithms on a Sybase system can be used to identify open reading frames (ORFs) within sequences such as the EST's that are provided herein and that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

EXAMPLES

Example 1

This Example illustrates the construction and DNA sequence analysis of SCN genome libraries.

SCN genomic DNA libraries (LIB5513, LIB 5514, LIB5519, and LIB5520) were constructed from SCN strain OP25 genomic DNA (Dong et al., 1997, Genetics 146:1311-1318). The libraries were generated by ligating size-selected physically sheared DNA into the high copy number plasmid pUC18 and the resulting ligation mixture was transformed into *E. coli* by electroporation. 10 micrograms of SCN genomic DNA were resuspended into 30 microliters TE buffer. The DNA was sheared by sonication. The sonicated DNA was 5' end-repaired using T4 DNA polymerase (New England BioLabs) and 10 mM dNTP's in a total reaction volume of 35 microliters and equilibrated to 1× ligation buffer (New England BioLabs). 3' overhangs were repaired by treatment with T4 polynucleotide kinase. The mixture was incubated at 15° C. for 20 minutes, and transferred to 65° C. for 15 minutes to inactivate the kinase and polymerase, and incubated at room temperature for an additional 10 minutes. The repaired DNA was size fractionated by electrophoresis in a 0.7% agarose gel adjacent to a 1 Kb molecular weight marker at 80 volts for two hours in TBE buffer. The 2-4 KB and 4-8 KB DNA fragments were excised from the agarose gel and transferred into microcentrifuge tubes. The size-selected DNA fragments were isolated from the agarose gel and a second round of size selection was performed to eliminate small DNA fragments co-migrating with the selected range in first gel fractionation. Approximately 100 nanograms of the size-selected repaired DNA was inserted by ligation into a pUC18-HincII digested vector (molar ratio of 5 to 1). The ligated DNA was transformed into *E. coli* DH10B cells by electroporation and planted to LB plates containing 100 micrograms per milliliter ampicillin and incubated for 18-24 hours at 37 C. Several colonies that arose after incubation were randomly selected. The colonies were tested to determine the average DNA insert size and the average number of colonies in the library that appeared to contain no inserted recombinant DNA. Four libraries were constructed. The average insert size in library LIB5513 was 2-4 KB, in library LIB5514 was 4-8 KB, in library LIB5519 was 2-4 KB, and in library LIB5520 was 4-8 KB. Samples of each library were collected and combined together and deposited with the American Type Culture Collection (ATCC) at Rockville Md., USA on Feb. 15, 2005. The combined library was submitted to ATCC, designated as LIB5513_14_19_20, and the ATCC has assigned the patent deposit number PTA-6583 to the deposited material.

The cells of the libraries were then plated on large bioassay plates containing Luria Broth (Difco) supplemented with 100 microgram/milliliter carbenicillin (ICN Biomedical), 64 microgram/milliliter IPTG (Shelton Scientific) and 80 microgram/milliliter X-Gal (Shelton Scientific). Individual blue transformants were then picked into 1.2 ml Terrific Broth (Difco) supplemented with 125 μg/ml Ampicillin (Calbiochem) in 96 deep-well boxes by Genetix Q-bot. The boxes were incubated for 21 hours at 37° C., each well archived to individual wells in 384-well glycerol plates, and then pelleted and stored at −20 C.

Alkaline lysis DNA extraction was performed on samples of pelleted clones using a QUIAGEN bead based platform on an automated robotic preparation system. Eluted DNA was stored for sequencing at 4° C. in a 96-well COSTAR plate. Two microliters of the DNA solution was then transferred into a 384 well microtiter plate (AXYGEN) using a Hamilton MPH96 Pipetting Robot. The pipetted DNA was then denatured for 5 minutes at 95° C., and two microliters of Big Dye Reaction Mix (Big Dye Terminators v3.0, 3.2 pmol sequencing primer, 1×TNK, and 0.5M $MgCl_2$) was then added to the denatured DNA using a Hamilton MPH96 Pipetting Robot. Each clone was sequenced using M13 forward and reverse primers in a PCR sequencing reaction using the conditions as follows: 95° C. for 5 seconds, 45° C. for 5 seconds, 60° C. for 2 minutes 30 seconds for a total of 25 cycles. The sequencing reactions were ethanol precipitated and re-suspended in water and loaded onto an ABI 3730xl Sequencing Analyzer (APPLIED BIOSYSTEMS) to generate sequence trace data for each sample. Approximately 400,000 sequencing reads were generated from the four *Heterodera glycines* genome libraries.

Example 2

This Example illustrates the analysis, characterization, and assembly of the sequences obtained from DNA sequence analysis of the SCN genome libraries.

The sequence trace data was converted to sequence and quality files and standard quality control procedures were applied through the use of the block 0/1 pipelines. Quality control procedures included sequence quality trimming, sequence identity, cloning sequence removal, and contamination identification and removal. The results of the general sequencing pre-processing steps were stored in the sequence database SeqDB. Data passing quality controls were retrieved for inclusion in the assembly step. The dataset to be assembled consisted of 338,266 sequence reads that passed the block 0/1 process, represented by an initial output of 404,372 sequencing reads that were submitted to the block 0/1 process. A file of clone pair constraints was produced on the basis of known clone naming conventions and library construction details (insert size range). The clone pair constraint file consisted of 159,389 pairwise entries. Fasta, quality, and constraint files were used as input to the PCAP program (Version Date: Sep. 3, 2004, Huang, X., Wang, J., Aluru, S., Yang, S.-P. and Hillier, L. (2003): PCAP: A Whole-Genome Assembly Program. Genome Research, 13: 2164-2170), and the sequences were assembled. 45,568 output genomic contig sequences were produced whose sum length represented about 80.8 Million bases. These contig sequences are represented by the sequences as set forth in SEQ ID NO:1-SEQ ID NO:45568 and were subsequently used as input sequences to define generic regions of the SCN genome sequence corresponding to predicted coding sequences (referred to herein as vcDNA's or virtual complementary DNA's) and predicted promoter and intronic sequences.

SCN expressed sequences were collected from public sources and used to compare the genomic sequences identified herein as well as to identify unique sequences not present in any known public database set. Public sequences were collected into a file which contained non-identical contigs from (1) the Genome Sequencing Center at Washington University in St. Louis, Mo., USA (Nemagene clusters; McCarter et al., 2003, J. Nematology 35:465-469), (2) Parkinson contigs (Nembase clusters; Parkinson et al., 2004, Nature Genetics 36:1259-1267), (3) EST's in GenBank not contained in contigs (singletons), and (4) nucleotide sequences representing non-EST DNA sequences in GenBank (e.g., mRNAs). These sequences were compiled into and referred to herein as an essential gene sequence list corresponding to sequences as set forth herein at SEQ ID NO:47644-SEQ ID NO:50775.

Gene finding results were consolidated in a relational database in such a way that each predicted gene is represented by a set of coordinates that define the position of all segments of the gene on the genomic DNA contig (gDNA). The genes are described herein, and in particular in the Feature Fields of the Sequence Listing with reference to the nucleotide positions of each vcDNA giving rise to an amino acid sequence and in the amino acid sequence SEQ ID NO's as nucleotide sequences corresponding to portions of vcDNA's encoding the amino acid sequence. Sequences between the indicated protein coding portions correspond to predicted intronic sequences. Other sequence segments that are represented at least in the genomic sequences set forth in SEQ ID NO:1-SEQ ID NO:45568 include but are not limited to peptide-encoding segments such as initial exon, internal exon, terminal exon, or single exon and the like, and non-coding segments including promoter regions, transcription initiation sequences, transcription termination sequences, and polyadenylation signal sequences, and the like. Often the same position within a gDNA contig is predicted to contain a gene by more than one gene finding program. Thus, in order to prepare a library of genes where each position (locus) of the genome is represented by a single gene, several different gene prediction methods were applied and the results were consolidated according to the following algorithm.

1. For each gDNA contig, all clusters of overlapping genes were defined. Each cluster was assumed to correspond to a single gene. The cluster was defined as a set of sequences located on the same DNA strand and either predicted to overlap based on nucleotide sequence identity along the lengths of the sequences or predicted to be located closer than 50 nucleotides from each other. Only peptide-encoding segments were considered when defining a cluster. The start and end positions of the cluster define the maximal dimension of the gene.

2. For each cluster the preferred gene was selected, which represents this locus in the library. The selection algorithm is described as follows:

(a) All genes in a cluster were ranked by the gene-prediction method that produced them. The ranking by the different methods was intended to describe assumed accuracy of the method in predicting genes. The ranking was ordered arbitrarily using FgeneSH, Genemark.hmm and AAT/NAP data results. The AAT/GAP results were not ranked at all, but were used only if there were no other prediction for the locus, i.e. cluster contained only gene(s) predicted by AAT/GAP.

(b) The highest ranking gene was selected unless there were several equally ranked genes (i.e. predicted by the same method) or the cluster coverage by this gene was below 60%. The cluster coverage was computed as the ratio of the gene length to the length of the cluster (maximal dimension of the gene).

(c) For equally ranked genes, the gene with highest cluster coverage was selected.

(d) If the cluster coverage for the best-ranking gene was below 60%, the lower ranking genes were considered (in the ranking order) and the first one providing a gain in cluster coverage of at least 10% was selected.

(e) If a cluster contained only AAT/GAP-predicted genes—the one with the best cluster coverage was selected.

(f) For all other clusters, additional filtering was completed—only sequences that exhibited a translation product of at least 16 amino acids in length were selected.

(g) If a cluster contained only Genemark.hmm-predicted genes—no gene was selected and the locus was assumed not to contain any gene.

The method described above resulted in a list of "preferred" genes. The actual DNA sequence for each of these genes was prepared by extracting a subsequence (region of a sequence) of a gDNA contig which corresponded to the coordinates of the gene. The sequences prepared contained all predicted exons and introns of the gene. In the case of AAT/GAP and FgeneSH genes they also may contain regions between transcription and translation initiation sequences, and between translation termination and polyadenylation sequences.

The three gene-predicting programs—FgeneSH, Genemark.hmm and AAT/NAP—in addition to predicting positions of genes, also predict sequences of the translation product, if any. Thus, the "preferred" genes and their translated peptide sequences were simultaneously predicted by these methods. Virtual cDNA sequences (vcDNA) were prepared from genes derived only from AAT/GAP prediction results by extracting regions of genomic DNA (gDNA) corresponding to the predicted exons and splicing them together. These virtual cDNA sequences were translated using a translator tool. The feature fields of indicated peptide SEQ ID NO's identify genomic contig sequence positions (for example, Contig_ID=SeqID_XXX) for the coding sequence contained therein. Additional information provided in the feature fields includes the identity of SCN-specific sequences, the nucleotide positions of these sequences in the vcDNA sequence, homology to existing sequences in publicly available databases, a numerical evaluation of the extent of the homology, and the predicted function if any associated with the peptide.

The vcDNA sequences were used to identify sequences corresponding to SCN specific promoter sequences using the following procedure:

1. For each gene predicted by either of the FgeneSH, Genemark.hmm or AAT/NAP prediction algorithms, the position of the first peptide-encoding segment was used as the reference point for sequence extraction. The sequence of the gDNA contig which starts 1000 nucleotides upstream and ends 2 nucleotides downstream of the reference point was extracted.

2. The resulting sequence of the upstream region was shorter if the gene was located closer than 1000 nucleotides to the end of the genomic contig. If there was another gene located upstream and predicted by one of these methods—FgeneSH, Genemark.hmm or AAT/NAP, the upstream region was shortened (truncated) so that it did not overlap with the closest peptide-encoding segment of that gene. If the resulting sequence was shorter than 50 nucleotides, it was not included as a promoter sequence in the library of promoter sequences.

3. If the resulting sequence did not end with the translation initiation codon ATG, i.e., the predicted gene was not N-terminal complete—then the sequence was not included as a promoter sequence in the library of promoter sequences.

4. Sequences located upstream of AAT/GAP-predicted genes were not included in the library of promoter sequences since this program did not predict a translation initiation position and in certain situations placed the predicted gene on the wrong strand of a gDNA contig.

Example 3

This Example illustrates the annotation of predicted SCN genes.

Two methodologies were used to provide annotations of the predicted *Heterodera glycines* (SCN) peptides, including Gene ontology (GO) and SmartBlast. Both GO and SmartBlast procedures were developed through homology-based sequence searches. In GO procedures, the peptide sequences from SCN peptides were used to BLAST against a protein sequence database, for example, the non-redundant protein (nr-aa) database maintained by the National Center for Biotechnology Information as part of GenBank. The highly conserved homologues of nr-aa from a variety of species were further selected with a minimal E value of 1E-08. The selected SCN homologues were subjected to the sequence match with a protein sequence database (GO proteins from GO Ontology consortium). Finally, three categories according to the GO Ontology consortium (molecular function; biological process; and cellular component) were used to annotate the SCN sequences. In SmartBlast procedures, the peptide sequences from SCN peptides were also used to blast against the non-redundant protein as described above. The homologues were also selected with a minimal E value of 1E-08. Those homologues were subjected to filtering using some non-meaningful words, such as "putative". The best meaningful homologues were used for SCN sequence annotation. The conditions used to provide the homolog annotation and the best hit with respect to any predicted SCN gene product were referred to in one or more of the feature fields for each of the SCN protein sequences selected from the group consisting of SEQ ID NO:119146-SEQ ID NO:121220, and were further identified as to molecular function, enzyme activity, cellular component and biological process. Genes characterized as encoding proteins that may be essential for survival based on the proteins' relationship at least to one or more *C. elegans* homologs and the phenotype of the knockout of the *C. elegans* homolog were further identified in one or more of the feature fields of each of the peptide sequences. The phenotype observed, abbreviations for each, and the standard nomenclature assigned for each with reference to that same phenotype and nomenclature in *C. elegans* was identified previously hereinabove.

Example 4

This Example illustrates a method for screening the SCN genome sequences, the predicted vcDNA sequences, and the predicted amino acid sequence encoded therefrom, against other sequences and selecting sequences unique to SCN.

The sequences disclosed herein can be used in a method to provide a DNA construct for expression of a dsRNA that is effective for silencing of a gene in a soybean cyst nematode or other plant pest by expressing such DNA construct in the cells of a transgenic plant and providing the plant in the diet of the nematode or pest. DNA sequences can be selected from the sequences of the present invention that are useful in achieving dsRNA-mediated gene silencing by selecting from a target gene a DNA sequence consisting of at least from about 17 to about 21 or more contiguous nucleotides. Effective short interfering RNA's (siRNAs) for gene repression are normally from about 21 to about 23-nt long double-stranded RNA duplexes. These siRNA's are known to incorporate into the RNA-inducing silencing complex (RISC). Once unwound, the single-stranded antisense strand guides RISC to the target mRNA, and induces the cleavage of the target messages, resulting in translational inhibition (Dykxhoorn, et al. Molecular Cell Biology, 4:457-467, 2003). Plant siRNA sequences have been characterized generally as contiguous nucleotide sequences of from about 24 nucleotides in length (Tang, 2003, Genes & Development 17:49-63). It is preferred that interfering RNA molecules are selected from the sequences as set forth in SEQ ID NO:1-SEQ ID NO:97729 to limit the un-intended "off-target" effect of gene repression by limiting the potential base-pairing with unintended targets of the host or other non-target organisms.

Example 5

This example illustrates the identification of SCN genes that can be targeted for suppression using the nucleotide sequences of the present invention.

A comparison of the SCN genes was made to the genes identified in *C. elegans* for which knockouts have been previously identified to result in an observable phenotype. RNAi phenotypes include maternal sterile, embryonic lethal and a variety of postembryonic phenotypes. The relationship between *C. elegans* knockout phenotypes and their protein sequences were obtained. These protein sequences were then compared to the protein sequences translated from the SCN genomic sequences of the present invention.

A BLAST searchable "All Protein Database" was constructed, which was composed of genome-wise SCN peptides and *C. elegans* proteins. A reciprocal blast procedure was used to identify the possible orthologues of *C. elegans* for each SCN peptide.

The All Protein Database was queried using protein sequences of the SCN peptides using the "blastp" algorithm with an E-value cutoff of 1e-8. Up to 1000 hits were retained for each SCN peptide used in the query, and separated by organism names, either *C. elegans* or SCN. For *C. elegans*, a list was retained for the hits with SCN sequences exhibiting a more significant E-value than the best hit of the organism. The list contains likely duplicated SCN genes, and was referred to as a Core List. Another list was retained for all the hits from each organism, sorted by the E-value, and was referred to as a Hit List. The hit was identified as an orthologue of the query sequence if it was within the Core List.

Knockout phenotypes of SCN were inferred according to the degree of evolutionary relationship determined to exist between SCN and *C. elegans* proteins with reference to the knockout phenotypes of *C. elegans* genes, referred to herein above. For example, *C. elegans* C37H5.8 corresponds to a HSP-6 protein, and a knockout of this gene has been associated with the observed phenotypes of embryonic lethality and larval arrest. Orthologue identification from the above query indicated that an SCN amino acid sequence corresponding to SEQ ID NO:119310 is an orthologue of C37H5.8. Therefore, it is believed that because of the relationship of the SCN sequence corresponding to SEQ ID NO:119310 to the *C. elegans* orthologue C37H5.8, suppression of the SCN gene corresponding to SCN vcDNA sequence as set forth at SEQ ID NO:45733 encoding the C37H5.8 orthologue at SEQ ID NO:119310 would be expected to result in an observable phenotype corresponding to embryonic lethal and/or larva arrest in SCN. SCN genes have been categorized based on their relationship to identifiable orthologues with genes or sequences in other organisms and some are further identified as essential genes. Such information has been provided for each amino acid sequence predicted from the vcDNA sequences and is listed in the feature fields for each sequence in the sequence listing. The feature field in the sequence listing has been used to identify important features of the DNA molecules of the present invention. A DNA construct that contains target sequences from multiple SCN essential genes can be constructed to express a chimeric dsRNA molecule that affects more than one SCN gene. This aspect of the present invention reduces the possibility of selecting for a population of SCN that is unaffected by the dsRNA molecule.

SCN genes were grouped into Pfam protein families. Pfam is a comprehensive database of protein domain families, based on multiple alignments of protein domains or conserved protein regions (*Nucleic Acids Research* 2004 32:D138-D141; *Proteins* 28:405-420, 1997.). Peptide sequences of a subset of SCN genes have been matched to Pfam entries with HMMPFAM program, with an expectation value cutoff of 0.1 (Biological sequence analysis: probabilistic models of proteins and nucleic acids, Cambridge University Press, 1998.) The subset included 5207 SCN protein sequences that were analyzed by this method, and 3397 of the 5207 protein sequences were grouped into 909 families, as set forth in Table 1.

In order to target a protein gene family for suppression with a single dsRNA molecule, it may be necessary to identify conserved DNA sequence regions among protein gene family members. After the amino acid sequence translations from the virtual cDNA sequences were grouped into protein families, the conserved sequence regions were identified through multiple sequence alignment of the DNA sequences of the family members. For example, using the program CLSUTALW (ref. *Nucleic Acids Res.* 22:4673-4680), member sequences of a Pfam group can be aligned. One example is illustrated by an alignment of SEQ ID NO's representative of the nucleotide sequences encoding the protein family members in the MRP_L47 family, a mitochondrial ribosomal protein family, corresponding to SEQ ID NO:49132 (HG02471), SEQ ID NO:50709 (HGC08009), and SEQ ID NO:46538 (HG2_27019.C1.o1.np). An alignment of these three sequences allows the identification of conserved contiguous residues present in each of the three sequences. The conserved segments consisting of at least 21 contiguous nucleotides are representative of the preferred polynucleotide regions for expression in a double stranded RNA sequence for use in targeting the suppression of each member of the entire gene family. The comparison of protein sequences of family members identified and grouped in Table 1 enables the identification of related polynucleotide regions common among the family members by locating the corresponding cDNA and genomic contig sequences identified in the feature field of the Sequence Listing. Using this method of comparison, the protein sequences of family members identified in Table 1 and in SEQ ID NO:119146-SEQ ID NO:124352 allows the skilled artisan to identify the related polynucleotide regions that are common among the family members by locating the corresponding virtual cDNA (vcDNA) and genomic contiguous sequences as set forth in SEQ ID NO:1-SEQ ID NO:119145. These sequences can then be used in a DNA construct to express a dsRNA molecule in plant cells that is directed to the suppression of one or more genes in any of one or more plant pests. These polynucleotides can then be used in a DNA construct to express a homologous dsRNA molecule in plant cells.

TABLE 1

SCN GENE FAMILIES and ANNOTATIONS
SCN gene families

| Gene name | SCN gene family members | Protein annotation |
|---|---|---|
| bZIP_1 | SeqID_122625 SeqID_119811 SeqID_124042 SeqID_124331 SeqID_121799 | bZIP transcription factor |
| Mito_carr | SeqID_121264 SeqID_122047 SeqID_122051 SeqID_122111 SeqID_122259 SeqID_122457 SeqID_122504 SeqID_122594 SeqID_121347 SeqID_121360 SeqID_121361 SeqID_122965 SeqID_122993 SeqID_123057 SeqID_123135 SeqID_123186 SeqID_123212 SeqID_123240 SeqID_123284 SeqID_123348 SeqID_123379 SeqID_123391 SeqID_123930 SeqID_119420 SeqID_119539 SeqID_120127 SeqID_120194 SeqID_120280 SeqID_121563 SeqID_121585 SeqID_120988 SeqID_121115 SeqID_123589 SeqID_123608 SeqID_123626 SeqID_123732 SeqID_123814 SeqID_123863 SeqID_121678 SeqID_124088 SeqID_124151 SeqID_124350 SeqID_121751 SeqID_121752 SeqID_121870 | Mitochondrial carrier protein |
| bZIP_2 | SeqID_121260 SeqID_122546 SeqID_122625 SeqID_119811 SeqID_124042 SeqID_121799 | Basic region leucine zipper |
| Sec7 | SeqID_120412 | Sec7 domain |
| MutS_IV | SeqID_119581 | MutS family domain IV |
| CtaG_Cox11 | SeqID_119768 | Cytochrome c oxidase assembly protein Cta |
| Synaptobrevin | SeqID_122614 SeqID_122853 SeqID_123133 SeqID_123159 SeqID_123266 SeqID_120966 SeqID_121065 SeqID_123723 | Synaptobrevin |
| Fer2 | SeqID_122093 SeqID_122357 SeqID_119370 SeqID_124223 SeqID_124309 | 2Fe—2S iron-sulfur cluster binding domain |
| WD40 | SeqID_121225 SeqID_121265 SeqID_122030 SeqID_122050 SeqID_122140 SeqID_122192 SeqID_122212 SeqID_122243 SeqID_122288 SeqID_122350 SeqID_122349 SeqID_122434 SeqID_122449 SeqID_122509 SeqID_122514 SeqID_122539 SeqID_122547 SeqID_121310 SeqID_121337 SeqID_121375 SeqID_122883 SeqID_122959 SeqID_122996 SeqID_123045 | WD domain, G-beta repeat |

TABLE 1-continued

SCN GENE FAMILIES and ANNOTATIONS
SCN gene families

| Gene name | SCN gene family members | Protein annotation |
|---|---|---|
| | SeqID_123090 SeqID_123107 | |
| | SeqID_123122 SeqID_123198 | |
| | SeqID_123318 SeqID_123329 | |
| | SeqID_121391 SeqID_119248 | |
| | SeqID_119272 SeqID_119279 | |
| | SeqID_119343 SeqID_119431 | |
| | SeqID_119538 SeqID_119627 | |
| | SeqID_119670 SeqID_119769 | |
| | SeqID_119826 SeqID_119840 | |
| | SeqID_119913 SeqID_119990 | |
| | SeqID_121523 SeqID_120032 | |
| | SeqID_120112 SeqID_120134 | |
| | SeqID_120235 SeqID_120302 | |
| | SeqID_120344 SeqID_120362 | |
| | SeqID_120457 SeqID_120458 | |
| | SeqID_120507 SeqID_120508 | |
| | SeqID_120576 SeqID_120747 | |
| | SeqID_120826 SeqID_120866 | |
| | SeqID_120885 SeqID_120945 | |
| | SeqID_120994 SeqID_120997 | |
| | SeqID_121007 SeqID_121094 | |
| | SeqID_121096 SeqID_121116 | |
| | SeqID_121184 SeqID_121199 | |
| | SeqID_123563 SeqID_123612 | |
| | SeqID_123643 SeqID_123841 | |
| | SeqID_123880 SeqID_121640 | |
| | SeqID_123965 SeqID_124104 | |
| | SeqID_124118 SeqID_124150 | |
| | SeqID_124186 SeqID_124334 | |
| | SeqID_121790 SeqID_121804 | |
| | SeqID_121816 SeqID_121840 | |
| | SeqID_121844 | |
| Skp1 | SeqID_121262 SeqID_122339 SeqID_121318 SeqID_119848 | Skp1 family, dimerisation domain |
| Fer4 | SeqID_122076 SeqID_122198 SeqID_120449 SeqID_120455 SeqID_124131 | 4Fe—4S binding domain |
| Enolase_C | SeqID_122156 SeqID_123621 | Enolase, C-terminal TIM barrel domain |
| Mucin | SeqID_120313 | Mucin-like glycoprotein |
| NHL | SeqID_121326 | NHL repeat |
| FAT | SeqID_122973 SeqID_120212 | FAT domain |
| Iso_dh | SeqID_122456 SeqID_120630 SeqID_123561 | Isocitrate/isopropylmalate dehydrogenase |
| APH | SeqID_122384 SeqID_122682 SeqID_121416 SeqID_119410 SeqID_119453 SeqID_119764 SeqID_121622 SeqID_120808 SeqID_124140 SeqID_121803 | Phosphotransferase enzyme family |
| Suf | SeqID_122937 | Suppressor of forked protein (Suf) |
| Enolase_N | SeqID_122156 SeqID_123621 | Enolase, N-terminal domain |
| Ldh_1_C | SeqID_122492 SeqID_120389 SeqID_123782 | lactate/malate dehydrogenase, alpha/beta C-t |
| HMG_CoA_synt | SeqID_122417 SeqID_120809 SeqID_121837 | Hydroxymethylglutaryl-coenzyme A synthas |
| PLDc | SeqID_119325 SeqID_120704 | Phospholipase D Active site motif |
| Glycos_transf_1 | SeqID_121164 | Glycosyl transferases group 1 |
| Dala_Dala_lig_C | SeqID_119260 | D-ala D-ala ligase C-terminus |
| Kunitz_BPTI | SeqID_122170 SeqID_119622 SeqID_119623 | Kunitz/Bovine pancreatic trypsin inhibito |
| Nuc_sug_transp | SeqID_119240 | Nucleotide-sugar transporter |
| cobW | SeqID_122575 | CobW/HypB/UreG, nucleotide-binding domain |
| L15 | SeqID_121270 SeqID_122374 SeqID_123713 | Ribosomal protein L15 |
| Ldh_1_N | SeqID_122492 SeqID_121371 SeqID_122868 SeqID_120389 SeqID_123782 | lactate/malate dehydrogenase, NAD binding do |
| CLP_protease | SeqID_122193 SeqID_122948 SeqID_124275 SeqID_120143 SeqID_123619 SeqID_121952 | Clp protease |
| HEAT_PBS | SeqID_122486 SeqID_120345 SeqID_123693 | PBS lyase HEAT-like repeat |
| NIC | SeqID_121904 | Nucleoporin interacting component |
| SecY | SeqID_122609 SeqID_123948 | eubacterial secY protein |

TABLE 1-continued

SCN GENE FAMILIES and ANNOTATIONS
SCN gene families

| Gene name | SCN gene family members | Protein annotation |
| --- | --- | --- |
| PCI | SeqID_122070 SeqID_122383 SeqID_119309 SeqID_119633 SeqID_120088 SeqID_120892 SeqID_123711 SeqID_123975 SeqID_121783 | PCI domain |
| Abhydro_lipase | SeqID_119405 | ab-hydrolase associated lipase region |
| Mra1 | SeqID_123459 | Suppressor Mra1 |
| tRNA-synt_1b | SeqID_123017 SeqID_120260 SeqID_121648 | tRNA synthetases class I (W and Y) |
| NIF | SeqID_121832 | NLI interacting factor-like phosphatase |
| Laminin_G_1 | SeqID_120488 | Laminin G domain |
| tRNA-synt_1c | SeqID_122217 SeqID_122354 SeqID_123425 SeqID_119559 SeqID_120889 SeqID_123797 | tRNA synthetases class I (E and Q), cata |
| Laminin_G_2 | SeqID_120488 | Laminin G domain |
| tRNA-synt_1e | SeqID_119570 SeqID_119679 | tRNA synthetases class I (C) catalytic d |
| Acyl-CoA_dh_M | SeqID_123412 SeqID_119407 SeqID_119554 | Acyl-CoA dehydrogenase, middle domain |
| Mak16 | SeqID_123061 SeqID_120231 SeqID_120297 | Mak16 protein |
| Clp1 | SeqID_120900 | Pre-mRNA cleavage complex II protein Clp1 |
| Guanylate_cyc | SeqID_119460 | Adenylate and Guanylate cyclase catalyst |
| Acyl-CoA_dh_N | SeqID_122997 SeqID_123412 SeqID_119407 SeqID_119740 SeqID_124296 | Acyl-CoA dehydrogenase, N-terminal doma |
| RNase_PH_C | SeqID_122716 SeqID_120146 | 3' exoribonuclease family, domain 2 |
| MoeZ_MoeB | SeqID_120491 | MoeZ/MoeB domain |
| Chitin_synth_2 | SeqID_120016 | Chitin synthase |
| PAP_central | SeqID_122343 SeqID_119183 SeqID_120181 SeqID_120989 SeqID_121025 SeqID_123810 | Poly(A) polymerase central domain |
| rve | SeqID_119251 SeqID_119810 | Integrase core domain |
| RED_N | SeqID_120411 | RED-like protein N-terminal region |
| Ank | SeqID_123070 SeqID_119179 SeqID_119568 SeqID_119583 SeqID_119584 SeqID_119680 SeqID_119792 SeqID_119874 SeqID_120226 SeqID_121617 | Ankyrin repeat |
| CKS | SeqID_122543 SeqID_121066 | Cyclin-dependent kinase regulatory subunit |
| Band_7 | SeqID_122693 SeqID_119534 SeqID_123829 | SPFH domain/Band 7 family |
| PAF-AH_p_II | SeqID_120737 SeqID_121196 | Platelet-activating factor acetylhydrolas |
| SF-assemblin | SeqID_120078 | SF-assemblin/beta giardin |
| Ribosomal_S24e | SeqID_122807 SeqID_120291 SeqID_124204 SeqID_124210 SeqID_121954 | Ribosomal protein S24e |
| Ribosomal_S17e | SeqID_122394 SeqID_119329 SeqID_123964 | Ribosomal S17 |
| Sof1 | SeqID_122192 SeqID_120865 SeqID_120866 SeqID_124334 | Sof1-like domain |
| LrgB | SeqID_120612 | LrgB-like family |
| DUF1650 | SeqID_122945 SeqID_123077 SeqID_120203 | Protein of unknown function (DUF1650) |
| Laminin_EGF | SeqID_121392 SeqID_119297 SeqID_119335 SeqID_119714 SeqID_119816 SeqID_120849 SeqID_120911 | Laminin EGF-like (Domains III and V) |
| TruB_N | SeqID_119847 | TruB family pseudouridylate synthase (N term |
| tRNA-synt_2b | SeqID_122133 SeqID_122759 SeqID_119832 SeqID_120346 SeqID_120388 SeqID_120642 SeqID_121608 SeqID_121085 SeqID_121645 SeqID_124158 SeqID_124247 | tRNA synthetase class II core domain (G, |
| tRNA-synt_2c | SeqID_120391 | tRNA synthetases class II (A) |
| Innexin | SeqID_123073 SeqID_123480 SeqID_120601 | Innexin |

TABLE 1-continued

SCN GENE FAMILIES and ANNOTATIONS
SCN gene families

| Gene name | SCN gene family members | Protein annotation |
|---|---|---|
| tRNA-synt_2d | SeqID_122320 SeqID_119409 SeqID_121659 SeqID_124019 | tRNA synthetases class II core domain (F |
| MFS_1 | SeqID_119430 SeqID_119607 SeqID_120612 | Major Facilitator Superfamily |
| Cyt-b5 | SeqID_122136 SeqID_122505 SeqID_119879 SeqID_123602 | Cytochrome b5-like Heme/Steroid bindin |
| MAM33 | SeqID_122105 SeqID_123650 | Mitochondrial glycoprotein |
| ZZ | SeqID_120217 | Zinc finger, ZZ type |
| Dpy-30 | SeqID_122847 SeqID_121204 | Dpy-30 motif |
| K_tetra | SeqID_122369 SeqID_119930 SeqID_120530 | K+ channel tetramerisation domain |
| Tim44 | SeqID_123264 SeqID_119402 | Tim44-like domain |
| Mtap_PNP | SeqID_121534 SeqID_121548 SeqID_121569 | Phosphorylase family 2 |
| PDZ | SeqID_119401 SeqID_120527 | PDZ domain (Also known as DHR or GLGF) |
| CHCH | SeqID_123527 | CHCH domain |
| Ribonuc_red_sm | SeqID_122881 SeqID_120548 SeqID_121571 SeqID_121595 | Ribonucleotide reductase, small chain |
| Pro_isomerase | SeqID_122368 SeqID_122436 SeqID_122839 SeqID_123273 SeqID_121384 SeqID_119354 SeqID_120150 SeqID_123750 SeqID_123891 SeqID_121707 SeqID_124224 | Cyclophilin type peptidyl-prolyl cis-tr |
| DIX | SeqID_123325 | DIX domain |
| Hydrolase | SeqID_119435 | haloacid dehalogenase-like hydrolase |
| Peptidase_C1 | SeqID_121248 SeqID_121247 SeqID_121267 SeqID_122029 SeqID_122165 SeqID_122555 SeqID_122593 SeqID_123403 SeqID_123446 SeqID_121447 SeqID_119313 SeqID_123567 SeqID_123581 SeqID_123578 SeqID_121782 SeqID_121853 SeqID_121879 | Papain family cysteine protease |
| Peptidase_C2 | SeqID_123259 SeqID_120192 SeqID_120374 | Calpain family cysteine protease |
| E1-E2_ATPase | SeqID_122184 SeqID_119574 SeqID_119844 SeqID_120162 | E1-E2 ATPase |
| Peptidase_M13 | SeqID_122218 | Peptidase family M13 |
| FLYWCH | SeqID_119876 SeqID_120405 | FLYWCH zinc finger domain |
| Peptidase_M14 | SeqID_122059 SeqID_122194 SeqID_119546 SeqID_123807 SeqID_124007 | Zinc carboxypeptidase |
| Sec62 | SeqID_121454 | Translocation protein Sec62 |
| Sec63 | SeqID_120914 | Sec63 domain |
| Peptidase_M16 | SeqID_123296 SeqID_119755 SeqID_124192 | Insulinase (Peptidase family M16) |
| EGF | SeqID_119714 SeqID_119985 SeqID_120013 SeqID_120488 SeqID_120732 SeqID_120849 | EGF-like domain |
| Ribonuc_red_lgC | SeqID_121385 | Ribonucleotide reductase, barrel doma |
| UPF0027 | SeqID_121387 | Uncharacterized protein family UPF0027 |
| APC10 | SeqID_122598 SeqID_119693 SeqID_123584 | Anaphase-promoting complex, subunit 10 (APC1 |
| Integrin_alpha | SeqID_119890 | Integrin alpha cytoplasmic region |
| Dynein_heavy | SeqID_120763 SeqID_120973 | Dynein heavy chain |
| Chromo | SeqID_119766 SeqID_120561 | 'chromo' (CHRromatin Organisation MOdifier) |
| Surp | SeqID_122195 SeqID_120133 SeqID_124100 SeqID_124099 | Surp module |
| Lipase_GDSL | SeqID_122975 SeqID_120739 | GDSL-like Lipase/Acylhydrolase |
| ASC | SeqID_119784 | Amiloride-sensitive sodium channel |
| F-actin_cap_A | SeqID_123125 SeqID_119252 | F-actin capping protein alpha subunit |
| Ribosomal_L2_C | SeqID_122387 SeqID_122576 SeqID_119709 SeqID_123662 SeqID_124015 SeqID_121759 SeqID_121891 | Ribosomal Proteins L2, C-terminal doma |

TABLE 1-continued

SCN GENE FAMILIES and ANNOTATIONS
SCN gene families

| Gene name | SCN gene family members | Protein annotation |
|---|---|---|
| TPR_1 | SeqID_122178 SeqID_122894 SeqID_123022 SeqID_119202 SeqID_119274 SeqID_119429 SeqID_119528 SeqID_119687 SeqID_120074 SeqID_120605 SeqID_121168 SeqID_121175 SeqID_123940 | Tetratricopeptide repeat |
| NTP_transf_2 | SeqID_122343 SeqID_123810 | Nucleotidyltransferase domain |
| TPR_2 | SeqID_122178 SeqID_122894 SeqID_123022 SeqID_119202 SeqID_119274 SeqID_119429 SeqID_119528 SeqID_119687 SeqID_120074 SeqID_120591 SeqID_120605 SeqID_120748 SeqID_120947 SeqID_121168 SeqID_121175 SeqID_123940 | Tetratricopeptide repeat |
| TPR_4 | SeqID_119202 | Tetratricopeptide repeat |
| COesterase | SeqID_122237 SeqID_119940 SeqID_120067 SeqID_120891 SeqID_124012 | Carboxylesterase |
| TLE_N | SeqID_123010 SeqID_119913 | Groucho/TLE N-terminal Q-rich domain |
| F-box | SeqID_122666 SeqID_124313 | F-box domain |
| MRP-L47 | SeqID_122709 SeqID_120115 SeqID_124286 | Mitochondrial 39-S ribosomal protein L47 (MR |
| Col_cuticle_N | SeqID_121964 SeqID_121988 SeqID_121996 SeqID_122013 SeqID_122019 SeqID_122027 SeqID_122291 SeqID_122304 SeqID_122313 SeqID_122472 SeqID_122536 SeqID_122871 SeqID_122911 SeqID_122927 SeqID_122954 SeqID_123029 SeqID_123087 SeqID_123176 SeqID_123223 SeqID_123423 SeqID_119404 SeqID_119564 SeqID_119730 SeqID_119798 SeqID_120106 SeqID_120175 SeqID_120474 SeqID_120705 SeqID_120750 SeqID_123663 SeqID_121026 SeqID_121073 SeqID_123664 SeqID_123677 SeqID_123676 SeqID_123769 SeqID_123783 SeqID_123827 SeqID_121953 SeqID_121957 | Nematode cuticle collagen N-terminal do |
| Na_H_Exchanger | SeqID_120225 SeqID_120403 | Sodium/hydrogen exchanger family |
| ATP-synt_ab | SeqID_122131 SeqID_122660 SeqID_122734 SeqID_122935 SeqID_119160 SeqID_123656 SeqID_123806 SeqID_123805 SeqID_124022 | ATP synthase alpha/beta family, nucleot |
| zf-B_box | SeqID_120931 | B-box zinc finger |
| FMO-like | SeqID_122732 SeqID_120410 SeqID_124057 | Flavin-binding monooxygenase-like |
| Ribosomal_S26e | SeqID_122109 SeqID_120185 SeqID_123649 | Ribosomal protein S26e |
| Ribosomal_S19e | SeqID_122794 SeqID_123065 SeqID_123504 SeqID_124003 SeqID_124229 SeqID_121859 | Ribosomal protein S19e |
| Peptidase_C12 | SeqID_122328 SeqID_120007 SeqID_121135 SeqID_124005 | Ubiquitin carboxyl-terminal hydrolase, |
| Peptidase_C13 | SeqID_122230 SeqID_121453 SeqID_121467 SeqID_120219 SeqID_120537 SeqID_121597 SeqID_124041 SeqID_121721 SeqID_121872 SeqID_121883 | Peptidase C13 family |
| Peptidase_C14 | SeqID_123489 | Caspase domain |
| Peptidase_M24 | SeqID_122645 SeqID_124035 SeqID_124033 | metallopeptidase family M24 |
| Ribosomal_L6e_N | SeqID_122489 SeqID_123683 | Ribosomal protein L6, N-terminal doma |
| Paf1 | SeqID_119976 | Paf1 |
| DUF1671 | SeqID_123049 | Protein of unknown function (DUF1671) |

TABLE 1-continued

SCN GENE FAMILIES and ANNOTATIONS
SCN gene families

| Gene name | SCN gene family members | Protein annotation |
|---|---|---|
| Complex1_51K | SeqID_122912 SeqID_123104 SeqID_123995 | Respiratory-chain NADH dehydrogenase 51 |
| Peptidase_M28 | SeqID_122327 SeqID_122621 SeqID_119445 SeqID_123920 | Peptidase family M28 |
| PFK | SeqID_120213 | Phosphofructokinase |
| DAGAT | SeqID_123153 SeqID_120048 SeqID_121202 | Diacylglycerol acyltransferase |
| RNA_pol_Rpb7_N | SeqID_122067 SeqID_121484 SeqID_121111 SeqID_123690 | RNA polymerase Rpb7, N-terminal domain |
| DnaJ_C | SeqID_121279 SeqID_122722 SeqID_121405 SeqID_120879 SeqID_123882 | DnaJ C terminal region |
| zf-DNL | SeqID_122584 SeqID_124310 | DNL zinc finger |
| CNH | SeqID_123483 SeqID_120283 SeqID_121627 | CNH domain |
| DNA_ligase_A_M | SeqID_123044 SeqID_119293 | ATP dependent DNA ligase domain |
| DNA_ligase_A_N | SeqID_119293 | DNA ligase N terminus |
| LACT | SeqID_119637 | Lecithin:cholesterol acyltransferase |
| Ribosomal_L11_N | SeqID_122466 SeqID_122612 SeqID_122798 SeqID_120200 SeqID_120321 SeqID_121603 SeqID_123787 SeqID_124218 | Ribosomal protein L11, N-terminal dom |
| Sec8_exocyst | SeqID_123021 | Sec8 exocyst complex component specific |
| Coatomer_E | SeqID_122494 SeqID_120679 SeqID_123777 | Coatomer epsilon subunit |
| TT_ORF2 | SeqID_122828 SeqID_123933 | TT viral ORF2 |
| DNA_primase_S | SeqID_122299 SeqID_123968 | DNA primase small subunit |
| NACHT | SeqID_122493 SeqID_119176 | NACHT domain |
| Ribosomal_S27e | SeqID_122380 SeqID_122513 SeqID_119700 SeqID_120329 SeqID_123636 SeqID_123738 | Ribosomal protein S27 |
| Na_K-ATPase | SeqID_122309 SeqID_124043 | Sodium/potassium ATPase beta chain |
| TIP49 | SeqID_122138 SeqID_121376 SeqID_119157 SeqID_119793 SeqID_123801 | TIP49 C-terminus |
| GNT-I | SeqID_119837 | GNT-I family |
| Clathrin | SeqID_119727 | Region in Clathrin and VPS |
| MutS_V | SeqID_119581 SeqID_119594 SeqID_120288 SeqID_120369 | MutS domain V |
| Acyl_CoA_thio | SeqID_122480 SeqID_121327 SeqID_123795 SeqID_121650 SeqID_121919 | Acyl-CoA thioesterase |
| PTPA | SeqID_121340 SeqID_123363 SeqID_119880 | Phosphotyrosyl phosphate activator (PTPA) pr |
| UPF0113 | SeqID_122707 | Uncharacterised protein family (UPF0113) |
| dsrm | SeqID_119344 | Double-stranded RNA binding motif |
| Tom22 | SeqID_122077 SeqID_124129 | Mitochondrial import receptor subunit Tom22 |
| EGF_CA | SeqID_119714 SeqID_119985 SeqID_120013 SeqID_120732 | Calcium binding EGF domain |
| lsy1 | SeqID_122830 SeqID_120949 | lsy1-like splicing family |
| ELM2 | SeqID_120201 SeqID_120354 SeqID_121080 | ELM2 domain |
| HA2 | SeqID_122331 SeqID_119298 SeqID_120256 SeqID_120575 SeqID_123546 SeqID_124253 | Helicase associated domain (HA2) |
| RdRP | SeqID_119588 | RNA dependent RNA polymerase |
| 2-oxoacid_dh | SeqID_119602 SeqID_121525 SeqID_120978 | 2-oxoacid dehydrogenases acyltransferase |
| UDPGP | SeqID_123086 | UTP--glucose-1-phosphate uridylyltransferase |
| Arf | SeqID_121288 SeqID_122204 SeqID_122360 SeqID_122392 SeqID_122397 SeqID_122560 SeqID_122575 SeqID_122579 SeqID_122619 SeqID_122671 SeqID_123132 SeqID_123241 SeqID_123422 SeqID_119204 SeqID_119645 SeqID_119853 | ADP-ribosylation factor family |

TABLE 1-continued

SCN GENE FAMILIES and ANNOTATIONS
SCN gene families

| Gene name | SCN gene family members | Protein annotation |
|---|---|---|
| | SeqID_120523 SeqID_120531 | |
| | SeqID_121613 SeqID_123568 | |
| | SeqID_123726 SeqID_123740 | |
| | SeqID_123960 SeqID_123988 | |
| | SeqID_123991 | |
| UDPGT | SeqID_119517 | UDP-glucoronosyl and UDP-glucosyl transferas |
| Cystatin | SeqID_122804 SeqID_120505 SeqID_123974 | Cystatin domain |
| ATP-synt_F6 | SeqID_122448 SeqID_120742 SeqID_123680 | Mitochondrial ATP synthase coupling facto |
| Cyto_heme_lyase | SeqID_122106 SeqID_124078 | Cytochrome c/c1 heme lyase |
| DNA_pol_alpha_B | SeqID_120691 | DNA polymerase alpha subunit B |
| Arm | SeqID_122305 SeqID_122870 | Armadillo/beta-catenin-like repeat |
| | SeqID_121423 SeqID_119427 | |
| | SeqID_121148 SeqID_121201 | |
| | SeqID_124047 SeqID_121836 | |
| NTP_transferase | SeqID_122569 SeqID_122914 SeqID_120001 | Nucleotidyl transferase |
| LSM | SeqID_122052 SeqID_122121 | LSM domain |
| | SeqID_122135 SeqID_122405 | |
| | SeqID_122422 SeqID_122654 | |
| | SeqID_122720 SeqID_122860 | |
| | SeqID_123047 SeqID_119181 | |
| | SeqID_119424 SeqID_120049 | |
| | SeqID_120122 SeqID_121030 | |
| | SeqID_123658 SeqID_123725 | |
| | SeqID_123789 SeqID_123944 | |
| | SeqID_124195 | |
| NMT | SeqID_120382 | Myristoyl-CoA:protein N-myristoyltransferase |
| TRAP-delta | SeqID_122068 SeqID_120359 SeqID_123786 | Translocon-associated protein, delta subun |
| DDOST_48kD | SeqID_121541 SeqID_121553 | Dolichyl-diphosphooligosaccharide-protein |
| Ribosomal_S28e | SeqID_122545 SeqID_120643 SeqID_123620 | Ribosomal protein S28e |
| UPF0120 | SeqID_122142 SeqID_121137 | Uncharacterised protein family (UPF0120) |
| Ala_racemase_N | SeqID_121220 | Alanine racemase, N-terminal domain |
| MFAP1_C | SeqID_119946 | Micro-fibrillar-associated protein 1 C-termi |
| Aminotran_3 | SeqID_119827 | Aminotransferase class-III |
| ACBP | SeqID_121287 SeqID_119464 | Acyl CoA binding protein |
| PHD | SeqID_123154 SeqID_119379 | PHD-finger |
| | SeqID_119449 SeqID_119766 | |
| | SeqID_120788 | |
| Aminotran_4 | SeqID_122578 SeqID_119653 SeqID_119738 | Aminotransferase class IV |
| E3_binding | SeqID_121975 SeqID_120333 | e3 binding domain |
| Ribosomal_L37ae | SeqID_122763 SeqID_119302 | Ribosomal L37ae protein family |
| | SeqID_120838 SeqID_123781 | |
| | SeqID_124249 | |
| zf-CCCH | SeqID_121226 SeqID_122128 | Zinc finger C-x8-C-x5-C-x3-H type (and simil |
| | SeqID_122531 SeqID_122888 | |
| | SeqID_123330 SeqID_119331 | |
| | SeqID_119820 SeqID_120375 | |
| | SeqID_120658 SeqID_121599 | |
| | SeqID_121064 SeqID_123669 | |
| HMG-CoA_red | SeqID_120545 | Hydroxymethylglutaryl-coenzyme A reductas |
| CRAL_TRIO | SeqID_120518 | CRAL/TRIO domain |
| HAT | SeqID_120676 | HAT (Half-A-TPR) repeat |
| Asn_synthase | SeqID_120554 SeqID_120715 | Asparagine synthase |
| PDCD9 | SeqID_122558 SeqID_123575 | Mitochondrial 28S ribosomal protein S30 (PDC |
| zf-CSL | SeqID_122103 SeqID_120511 SeqID_123712 | CSL zinc finger |
| UBACT | SeqID_122346 SeqID_121362 | Repeat in ubiquitin-activating (UBA) protein |
| | SeqID_121432 SeqID_121452 | |
| | SeqID_119364 SeqID_124102 | |
| | SeqID_121935 | |
| Biotin_carb_C | SeqID_120976 | Biotin carboxylase C-terminal domain |

TABLE 1-continued

SCN GENE FAMILIES and ANNOTATIONS
SCN gene families

| Gene name | SCN gene family members | Protein annotation |
|---|---|---|
| Frizzled | SeqID_120827 | Frizzled/Smoothened family membrane region |
| FH2 | SeqID_120125 | Formin Homology 2 Domain |
| Coatomer_WDAD | SeqID_119681 SeqID_120257 | Coatomer WD associated region |
| zf-RanBP | SeqID_123008 SeqID_121015 | Zn-finger in Ran binding protein and oth |
| COQ7 | SeqID_122535 SeqID_119203 SeqID_123627 | Ubiquinone biosynthesis protein COQ7 |
| Ammonium_transp | SeqID_120017 | Ammonium Transporter Family |
| PTR2 | SeqID_119430 SeqID_120270 | POT family |
| MPPN | SeqID_119150 | MPPN (rrm-like) domain |
| Pyr_redox | SeqID_119535 SeqID_120156 | Pyridine nucleotide-disulphide oxidoreducta |
| Carn_acyltransf | SeqID_119995 | Choline/Carnitine o-acyltransferase |
| TUDOR | SeqID_121121 | Tudor domain |
| Krr1 | SeqID_120316 | Krr1 family |
| Asp | SeqID_122475 SeqID_123036 SeqID_123118 SeqID_123359 SeqID_121455 SeqID_120476 SeqID_120494 SeqID_123971 | Eukaryotic aspartyl protease |
| BACK | SeqID_120833 SeqID_121637 | BTB And C-terminal Kelch |
| Uso1_p115_head | SeqID_122989 | Uso1/p115 like vesicle tethering pro |
| ATP-synt_ab_C | SeqID_122371 SeqID_122660 SeqID_123656 SeqID_123806 SeqID_123805 | ATP synthase alpha/beta chain, C termin |
| Thiolase_C | SeqID_122429 SeqID_122772 SeqID_120310 SeqID_123864 | Thiolase, C-terminal domain |
| 5_nucleotid | SeqID_120648 | 5' nucleotidase family |
| FHA | SeqID_120176 SeqID_120836 | FHA domain |
| PID | SeqID_123247 | Phosphotyrosine interaction domain (PTB/PID) |
| Citrate_synt | SeqID_122637 SeqID_122705 SeqID_120172 SeqID_124243 | Citrate synthase |
| Helicase_C | SeqID_122054 SeqID_122318 SeqID_122331 SeqID_122336 SeqID_122624 SeqID_122677 SeqID_119233 SeqID_119298 SeqID_119324 SeqID_119620 SeqID_119843 SeqID_119917 SeqID_120153 SeqID_120168 SeqID_120256 SeqID_120323 SeqID_120342 SeqID_120575 SeqID_120689 SeqID_120814 SeqID_120914 SeqID_121032 SeqID_123546 SeqID_121674 SeqID_124119 SeqID_124137 SeqID_124148 SeqID_124325 | Helicase conserved C-terminal domain |
| Neur_chan_LBD | SeqID_121005 SeqID_121087 | Neurotransmitter-gated ion-channel lig |
| Ion_trans_2 | SeqID_121451 SeqID_119613 SeqID_119930 SeqID_119939 | Ion channel |
| Myosin_tail_1 | SeqID_123386 | Myosin tail |
| TMS_TDE | SeqID_122691 SeqID_119438 SeqID_124263 | TMS membrane protein/tumour differentially e |
| P16-Arc | SeqID_119921 | ARP2/3 complex 16 kDa subunit (p16-Arc) |
| ATP-synt_ab_N | SeqID_122110 SeqID_122131 SeqID_122660 SeqID_119160 SeqID_123806 SeqID_123811 SeqID_124022 | ATP synthase alpha/beta family, beta-ba |
| Endonuclease_NS | SeqID_123055 | DNA/RNA non-specific endonuclease |
| Thiolase_N | SeqID_122429 SeqID_122772 SeqID_121350 SeqID_122890 SeqID_122953 SeqID_123288 SeqID_123365 SeqID_121440 SeqID_121529 SeqID_120310 SeqID_123593 SeqID_123864 | Thiolase, N-terminal domain |
| Glycogen_syn | SeqID_121477 SeqID_120492 | Glycogen synthase |
| BTB | SeqID_119616 SeqID_120373 SeqID_121165 SeqID_121637 | BTB/POZ domain |
| DUF236 | SeqID_119224 SeqID_119247 SeqID_120712 SeqID_120713 | Protein of unknown function |

TABLE 1-continued

SCN GENE FAMILIES and ANNOTATIONS
SCN gene families

| Gene name | SCN gene family members | Protein annotation |
| --- | --- | --- |
| Ubiq_cyt_C_chap | SeqID_122228 SeqID_121449 SeqID_119888 SeqID_123755 | Ubiquinol-cytochrome C chaperone |
| Renin_r | SeqID_122129 SeqID_121442 SeqID_123862 | Renin receptor-like protein |
| Cwf_Cwc_15 | SeqID_122116 SeqID_120731 SeqID_121658 SeqID_124014 | Cwf15/Cwc15 cell cycle control protein |
| A_deaminase | SeqID_121003 | Adenosine/AMP deaminase |
| DUF164 | SeqID_121260 SeqID_123386 | Uncharacterized ACR, COG1579 |
| ATP-synt_C | SeqID_122557 SeqID_122592 SeqID_122805 SeqID_123522 SeqID_119902 SeqID_119958 SeqID_119959 SeqID_120137 SeqID_124207 SeqID_124336 | ATP synthase subunit C |
| ATP-synt_D | SeqID_122796 SeqID_123297 SeqID_123366 SeqID_123854 | ATP synthase subunit D |
| LAG1 | SeqID_121272 SeqID_122595 SeqID_121367 | Longevity-assurance protein (LAG1) |
| ATP-synt_E | SeqID_123534 | ATP synthase E chain |
| ATP-synt_F | SeqID_122088 SeqID_121348 SeqID_121745 SeqID_121827 SeqID_121881 | ATP synthase (F/14-kDa) subunit |
| Filamin | SeqID_120307 SeqID_120510 | Filamin/ABP280 repeat |
| MazG | SeqID_119952 | MazG nucleotide pyrophosphohydrolase domain |
| ATP-synt_G | SeqID_122669 SeqID_119783 SeqID_124110 | Mitochondrial ATP synthase g subunit |
| EF1_GNE | SeqID_121982 SeqID_122152 SeqID_122572 SeqID_119628 SeqID_119899 SeqID_123606 | EF-1 guanine nucleotide exchange domain |
| FAD_binding_1 | SeqID_122094 SeqID_122444 SeqID_123823 | FAD binding domain |
| FAD_binding_2 | SeqID_120807 | FAD binding domain |
| Dynein_light | SeqID_122635 SeqID_123252 SeqID_119812 SeqID_123564 | Dynein light chain type 1 |
| FAD_binding_3 | SeqID_122411 SeqID_123933 | FAD binding domain |
| Astacin | SeqID_122226 SeqID_122581 SeqID_123481 SeqID_119601 SeqID_120015 SeqID_120571 SeqID_120933 SeqID_121174 SeqID_121216 SeqID_124300 | Astacin (Peptidase family M12A) |
| Tfb4 | SeqID_122561 SeqID_123565 | Transcription factor Tfb4 |
| Adaptin_N | SeqID_120538 SeqID_120950 | Adaptin N terminal region |
| EFG_IV | SeqID_121397 SeqID_120540 | Elongation factor G, domain IV |
| S-AdoMet_synt_C | SeqID_123143 SeqID_119596 | S-adenosylmethionine synthetase, C-te |
| Ribosomal_S10 | SeqID_122673 SeqID_119858 SeqID_123703 SeqID_121948 | Ribosomal protein S10p/S20e |
| Ribosomal_S11 | SeqID_122146 SeqID_123024 SeqID_123430 SeqID_120073 SeqID_120744 SeqID_123697 SeqID_124177 | Ribosomal protein S11 |
| Ribosomal_S12 | SeqID_122060 SeqID_123235 SeqID_123361 SeqID_123428 SeqID_123434 SeqID_123629 SeqID_124279 | Ribosomal protein S12 |
| UCR_hinge | SeqID_122302 SeqID_123516 | Ubiquinol-cytochrome C reductase |
| SH3_1 | SeqID_123228 SeqID_119323 SeqID_120958 | SH3 domain |
| Ribosomal_S13 | SeqID_122782 SeqID_122809 SeqID_123978 SeqID_124200 | Ribosomal protein S13/S18 |
| SAP | SeqID_120587 | SAP domain |
| SH3_2 | SeqID_123228 SeqID_120958 | Variant SH3 domain |
| Ribosomal_S14 | SeqID_122064 SeqID_122107 SeqID_120012 SeqID_121048 SeqID_121107 SeqID_123630 SeqID_123890 | Ribosomal protein S14p/S29e |
| Brix | SeqID_121565 SeqID_123250 SeqID_119314 SeqID_120464 SeqID_120490 SeqID_121589 SeqID_121109 | Brix domain |
| Ribosomal_S15 | SeqID_122373 SeqID_123410 SeqID_123433 SeqID_121412 SeqID_123718 | Ribosomal protein S15 |

TABLE 1-continued

SCN GENE FAMILIES and ANNOTATIONS
SCN gene families

| Gene name | SCN gene family members | Protein annotation |
|---|---|---|
| Ras | SeqID_121288 SeqID_122204 SeqID_122360 SeqID_122392 SeqID_122397 SeqID_122560 SeqID_122575 SeqID_122579 SeqID_122619 SeqID_122671 SeqID_122838 SeqID_122872 SeqID_122903 SeqID_123052 SeqID_123189 SeqID_123241 SeqID_123414 SeqID_123422 SeqID_119204 SeqID_119290 SeqID_119645 SeqID_119708 SeqID_119885 SeqID_119891 SeqID_120379 SeqID_120664 SeqID_121613 SeqID_120982 SeqID_123605 SeqID_121093 SeqID_123568 SeqID_123726 SeqID_123740 SeqID_121691 SeqID_123960 SeqID_123988 SeqID_123991 SeqID_121918 | Ras family |
| zf-TAZ | SeqID_120357 | TAZ zinc finger |
| Ribosomal_S17 | SeqID_122602 SeqID_122629 SeqID_119883 SeqID_123918 SeqID_123925 | Ribosomal protein S17 |
| Ribosomal_S18 | SeqID_122652 | Ribosomal protein S18 |
| ELK | SeqID_120763 | ELK domain |
| Ribosomal_S19 | SeqID_122056 SeqID_123333 SeqID_123450 SeqID_123685 | Ribosomal protein S19 |
| C2 | SeqID_119599 SeqID_119684 SeqID_120248 | C2 domain |
| eIF-5_eIF-2B | SeqID_123321 SeqID_119265 SeqID_120603 SeqID_121769 | Domain found in IF2B/IF5 |
| VWD | SeqID_122463 SeqID_123112 SeqID_119726 SeqID_123592 | von Willebrand factor type D domain |
| GHMP_kinases | SeqID_123199 | GHMP kinases putative ATP- |
| PAP_RNA-bind | SeqID_120989 | Poly(A) polymerase predicted RNA binding |
| C4 | SeqID_119273 SeqID_119634 | C-terminal tandem repeated domain in t |
| P_proprotein | SeqID_121230 SeqID_122663 SeqID_123014 SeqID_123393 | Proprotein convertase P-domain |
| ELO | SeqID_122222 SeqID_122315 SeqID_119651 SeqID_121493 SeqID_120991 SeqID_124009 SeqID_124028 | GNS1/SUR4 family |
| p450 | SeqID_120075 SeqID_120579 | Cytochrome P450 |
| Complex1_30kDa | SeqID_121297 SeqID_119579 | Respiratory-chain NADH dehydrogenase, |
| wnt | SeqID_122540 | wnt family |
| OATP | SeqID_119717 | Organic Anion Transporter Polypeptide (OATP) |
| RIIa | SeqID_122847 SeqID_121204 | Regulatory subunit of type II PKA R-subunit |
| Pyrophosphatase | SeqID_122209 SeqID_123850 | Inorganic pyrophosphatase |
| A1_Propeptide | SeqID_122475 SeqID_123036 SeqID_123359 SeqID_121455 SeqID_120476 SeqID_120494 SeqID_123971 | A1 Propeptide |
| PRP1_N | SeqID_121212 | PRP1 splicing factor, N-terminal |
| RhoGAP | SeqID_120222 SeqID_120311 | RhoGAP domain |
| G-alpha | SeqID_120144 SeqID_120531 SeqID_120703 SeqID_121138 | G-protein alpha subunit |
| Guanylate_kin | SeqID_120766 | Guanylate kinase |
| HSF_DNA-bind | SeqID_123050 | HSF-type DNA-binding |
| DnaJ_CXXCXGXG | SeqID_121279 SeqID_122722 SeqID_121405 SeqID_121507 SeqID_120879 SeqID_121218 SeqID_123882 | DnaJ central domain (4 repeats) |
| Collagen | SeqID_121964 SeqID_121996 SeqID_122013 SeqID_122019 SeqID_122027 SeqID_122216 SeqID_122291 SeqID_122304 SeqID_122313 SeqID_122472 SeqID_122536 SeqID_122650 SeqID_121377 SeqID_122871 SeqID_122911 SeqID_122954 | Collagen triple helix repeat (20 copies) |

TABLE 1-continued

SCN GENE FAMILIES and ANNOTATIONS
SCN gene families

| Gene name | SCN gene family members | Protein annotation |
|---|---|---|
| | SeqID_123029 SeqID_123087 | |
| | SeqID_123176 SeqID_123223 | |
| | SeqID_123423 SeqID_119253 | |
| | SeqID_119404 SeqID_119418 | |
| | SeqID_119540 SeqID_119564 | |
| | SeqID_119634 SeqID_119798 | |
| | SeqID_119948 SeqID_119971 | |
| | SeqID_120106 SeqID_120175 | |
| | SeqID_120214 SeqID_120361 | |
| | SeqID_120474 SeqID_120626 | |
| | SeqID_120674 SeqID_120705 | |
| | SeqID_123663 SeqID_121026 | |
| | SeqID_121073 SeqID_121150 | |
| | SeqID_123664 SeqID_123677 | |
| | SeqID_123676 SeqID_123769 | |
| | SeqID_123783 SeqID_123827 | |
| | SeqID_121953 SeqID_121958 | |
| Tubulin_C | SeqID_122269 SeqID_122332 | Tubulin/FtsZ family, C-terminal domain |
| | SeqID_122440 SeqID_119159 | |
| | SeqID_119381 SeqID_119720 | |
| | SeqID_120775 SeqID_123545 | |
| | SeqID_123884 SeqID_123998 | |
| | SeqID_121849 SeqID_121940 | |
| JmjC | SeqID_122284 SeqID_120520 | jmjC domain |
| Zona_pellucida | SeqID_119201 SeqID_120047 | Zona pellucida-like domain |
| CH | SeqID_122025 SeqID_122264 | Calponin homology (CH) domain |
| | SeqID_122337 SeqID_122473 | |
| | SeqID_122788 SeqID_123499 | |
| | SeqID_119750 SeqID_120539 | |
| | SeqID_123855 SeqID_124085 | |
| | SeqID_124206 | |
| E-MAP-115 | SeqID_120063 | E-MAP-115 family |
| CPSase_L_D2 | SeqID_119260 SeqID_119619 | Carbamoyl-phosphate synthase L chain, A |
| | SeqID_120976 | |
| HMG_box | SeqID_122876 SeqID_122918 | HMG (high mobility group) box |
| | SeqID_121497 SeqID_120582 | |
| | SeqID_120832 SeqID_120943 | |
| Ribosomal_S25 | SeqID_122611 SeqID_122695 | S25 ribosomal protein |
| | SeqID_123417 SeqID_123597 | |
| | SeqID_124222 SeqID_124340 | |
| Ribosomal_S27 | SeqID_122053 SeqID_122726 | Ribosomal protein S27a |
| | SeqID_121490 SeqID_123637 | |
| | SeqID_123659 | |
| Galactosyl_T | SeqID_120408 | Galactosyltransferase |
| CS | SeqID_122778 SeqID_122828 | CS domain |
| | SeqID_123335 SeqID_121480 | |
| | SeqID_120610 | |
| Voltage_CLC | SeqID_120735 SeqID_121213 | Voltage gated chloride channel |
| Lactamase_B | SeqID_120930 | Metallo-beta-lactamase superfamily |
| eRF1_1 | SeqID_119244 | eRF1 domain 1 |
| eRF1_2 | SeqID_123076 SeqID_119244 | eRF1 domain 2 |
| Flavoprotein | SeqID_122326 SeqID_119773 | Flavoprotein |
| eRF1_3 | SeqID_123076 SeqID_119244 | eRF1 domain 3 |
| EMP24_GP25L | SeqID_122517 SeqID_119571 | emp24/gp25L/p24 family |
| | SeqID_123733 | |
| NOT2_3_5 | SeqID_122445 SeqID_121346 | NOT2/NOT3/NOT5 family |
| | SeqID_123876 | |
| Hydantoinase_A | SeqID_121246 SeqID_121266 | Hydantoinase/oxoprolinase |
| Plus-3 | SeqID_122270 | Plus-3 domain |
| IBB | SeqID_122870 SeqID_121423 | Importin beta binding domain |
| | SeqID_119952 SeqID_121148 | |
| Ald_Xan_dh_C2 | SeqID_120485 SeqID_121912 | Aldehyde oxidase and xanthine dehydroge |
| Complex1_49kDa | SeqID_120479 | Respiratory-chain NADH dehydrogenase, |
| SSrecog | SeqID_120076 | Structure-specific recognition protein |
| Aldo_ket_red | SeqID_123277 | Aldo/keto reductase family |
| TFIIS_C | SeqID_122597 SeqID_123714 | Transcription factor S-II (TFIIS) |
| Thioredoxin | SeqID_121221 SeqID_122115 | Thioredoxin |
| | SeqID_122712 SeqID_123314 | |
| | SeqID_120315 SeqID_120528 | |
| | SeqID_121134 SeqID_123686 | |
| | SeqID_123796 SeqID_121887 | |

TABLE 1-continued

SCN GENE FAMILIES and ANNOTATIONS
SCN gene families

| Gene name | SCN gene family members | Protein annotation |
|---|---|---|
| vATP-synt_E | SeqID_122754 SeqID_121463 SeqID_119218 SeqID_124020 SeqID_121724 | ATP synthase (E/31 kDa) subunit |
| Metallothio | SeqID_119714 | Metallothinein |
| Mo-co_dimer | SeqID_122426 SeqID_119301 SeqID_123908 | Mo-co oxidoreductase dimensation doma |
| ORC2 | SeqID_121926 | Origin recognition complex subunit 2 |
| Ribosomal_S30 | SeqID_122415 SeqID_123507 SeqID_120390 SeqID_123707 | Ribosomal protein S30 |
| SCP | SeqID_121229 SeqID_121227 SeqID_121228 SeqID_122770 SeqID_122767 SeqID_122864 SeqID_123501 SeqID_121425 SeqID_119399 SeqID_119556 SeqID_120347 SeqID_121641 | SCP-like extracellular protein |
| GPP34 | SeqID_120614 | Golgi phosphoprotein 3 (GPP34) |
| DM | SeqID_121139 | DM DNA binding domain |
| GTP_CDC | SeqID_119791 | Cell division protein |
| AhpC-TSA | SeqID_122512 SeqID_122760 SeqID_123258 SeqID_123300 SeqID_119348 SeqID_123739 SeqID_123758 | AhpC/TSA family |
| CAP_GLY | SeqID_123227 | CAP-Gly domain |
| XRCC1_N | SeqID_120679 | XRCC1 N terminal domain |
| DUF26 | SeqID_122879 | Domain of unknown function DUF26 |
| TRAP_beta | SeqID_122465 SeqID_119980 SeqID_123848 | Translocon-associated protein beta (TRAPB) |
| Cation_ATPase_N | SeqID_122184 SeqID_119574 SeqID_119844 SeqID_120162 SeqID_124141 SeqID_124234 | Cation transporter/ATPase, N-terminus |
| XPG_I | SeqID_120903 | XPG I-region |
| TFIID-31kDa | SeqID_122432 SeqID_123899 | Transcription initiation factor IID, 31 kD |
| ARPC4 | SeqID_123032 SeqID_121098 | ARP2/3 complex 20 kDa subunit (ARPC4) |
| Nop | SeqID_122208 SeqID_119511 SeqID_120274 SeqID_123696 | Putative snoRNA binding domain |
| DX | SeqID_119623 | DX module |
| Choline_kinase | SeqID_122682 SeqID_124140 SeqID_121776 | Choline/ethanolamine kinase |
| Seryl_tRNA_N | SeqID_122169 SeqID_124027 | Seryl-tRNA synthetase N-terminal domain |
| UFD1 | SeqID_122278 SeqID_122991 SeqID_120363 SeqID_123652 | Ubiquitin fusion degradation protein UFD1 |
| AICARFT_IMPCHas | SeqID_121071 | AICARFT/IMPCHase bienzyme |
| Adap_comp_sub | SeqID_122747 SeqID_119495 SeqID_120295 | Adaptor complexes medium subunit family |
| V_ATPase_I | SeqID_121161 | V-type ATPase 116 kDa subunit family |
| eIF-6 | SeqID_122640 SeqID_120843 SeqID_123945 | eIF-6 family |
| TAF | SeqID_121234 SeqID_122483 SeqID_122744 SeqID_122771 SeqID_119330 SeqID_121479 SeqID_121482 SeqID_124258 SeqID_124262 | TATA box binding protein associated fac |
| HSP70 | SeqID_121224 SeqID_121246 SeqID_121258 SeqID_121266 SeqID_122340 SeqID_122574 SeqID_121338 SeqID_123128 SeqID_123276 SeqID_121398 SeqID_121394 SeqID_121403 SeqID_121456 SeqID_119310 SeqID_119878 SeqID_121465 SeqID_121528 SeqID_120193 SeqID_120276 SeqID_120425 SeqID_120426 SeqID_120477 SeqID_120618 SeqID_120675 SeqID_123580 SeqID_121647 SeqID_123958 SeqID_121785 | Hsp70 protein |
| Rho_GDI | SeqID_123503 SeqID_119733 SeqID_121942 | RHO protein GDP dissociation inhibitor |
| E2F_TDP | SeqID_122353 SeqID_120460 SeqID_120823 SeqID_124183 | E2F/DP family winged-helix DNA-binding domai |

TABLE 1-continued

SCN GENE FAMILIES and ANNOTATIONS
SCN gene families

| Gene name | SCN gene family members | Protein annotation |
|---|---|---|
| VPS28 | SeqID_122699 SeqID_119677 SeqID_124233 | VPS28 protein |
| SNARE | SeqID_122431 SeqID_123902 | SNARE domain |
| CBM_14 | SeqID_120683 | Chitin binding Peritrophin-A domain |
| Fic | SeqID_119770 | Fic protein family |
| Peptidase_M16_C | SeqID_123083 SeqID_119755 | Peptidase M16 inactive domain |
| efhand | SeqID_122031 SeqID_122171 SeqID_122356 SeqID_122443 SeqID_122544 SeqID_122641 SeqID_122769 SeqID_122783 SeqID_122802 SeqID_122976 SeqID_123119 SeqID_119228 SeqID_119553 SeqID_119614 | EF hand |
| zf-CCHC | SeqID_122365 SeqID_122548 SeqID_123105 SeqID_121406 SeqID_121418 SeqID_119748 SeqID_119884 SeqID_119889 SeqID_121017 SeqID_121081 SeqID_121192 SeqID_123993 | Zinc knuckle |
| Rieske | SeqID_119282 | Rieske [2Fe—2S] domain |
| EF_TS | SeqID_122638 SeqID_121030 | Elongation factor TS |
| GTP_EFTU | SeqID_122392 SeqID_122600 SeqID_122657 SeqID_121329 SeqID_122792 SeqID_122872 SeqID_123241 SeqID_121430 SeqID_119311 SeqID_119332 SeqID_119352 SeqID_119600 SeqID_120413 SeqID_120540 SeqID_121558 SeqID_121576 SeqID_121613 SeqID_123754 SeqID_121709 SeqID_123950 SeqID_124180 SeqID_121717 SeqID_121740 SeqID_121805 SeqID_121824 | Elongation factor Tu GTP binding domain |
| TPD52 | SeqID_120171 | Tumour protein D52 family |
| UCR_TM | SeqID_119282 SeqID_121586 SeqID_121732 SeqID_121833 | Ubiquinol cytochrome reductase transmembrane |
| Coq4 | SeqID_120870 | Coenzyme Q (ubiquinone) biosynthesis protein |
| zf-HIT | SeqID_123532 | HIT zinc finger |
| CUB | SeqID_123097 SeqID_119304 | CUB domain |
| DUF32 | SeqID_119459 SeqID_119801 SeqID_121149 | Domain of unknown function DUF32 |
| adh_short | SeqID_121285 SeqID_122087 SeqID_122187 SeqID_122421 SeqID_122523 SeqID_122530 SeqID_122596 SeqID_121476 SeqID_120081 SeqID_120916 SeqID_123628 SeqID_123706 SeqID_123772 SeqID_123943 | short chain dehydrogenase |
| RGS | SeqID_121152 | Regulator of G protein signaling |
| PMM | SeqID_122570 SeqID_124322 | Eukaryotic phosphomannomutase |
| ER | SeqID_121000 | Enhancer of rudimentary |
| Patched | SeqID_120169 SeqID_120785 SeqID_120998 | Patched family |
| RRM_1 | SeqID_121236 SeqID_121239 SeqID_122099 SeqID_122100 SeqID_122122 SeqID_122126 SeqID_122158 SeqID_122202 SeqID_122250 SeqID_122361 SeqID_122469 SeqID_122526 SeqID_122528 SeqID_122549 SeqID_122676 SeqID_122700 SeqID_122831 SeqID_122888 SeqID_122938 SeqID_122962 SeqID_123004 SeqID_123008 SeqID_123071 SeqID_123101 SeqID_123331 SeqID_123370 SeqID_123384 SeqID_123396 SeqID_123424 SeqID_119150 SeqID_119180 SeqID_119191 SeqID_119215 SeqID_119241 SeqID_124159 SeqID_119361 SeqID_119362 SeqID_119398 | RNA recognition motif. (a.k.a. RRM, RBD, or |

TABLE 1-continued

SCN GENE FAMILIES and ANNOTATIONS
SCN gene families

| Gene name | SCN gene family members | Protein annotation |
|---|---|---|
| I-set | SeqID_119489 SeqID_119527 SeqID_119551 SeqID_124128 SeqID_119655 SeqID_119820 SeqID_119864 SeqID_119970 SeqID_121498 SeqID_121513 SeqID_120027 SeqID_123815 SeqID_120174 SeqID_120251 SeqID_120319 SeqID_120336 SeqID_120348 SeqID_120467 SeqID_120468 SeqID_120514 SeqID_120570 SeqID_120741 SeqID_120765 SeqID_123671 SeqID_121559 SeqID_121578 SeqID_121599 SeqID_121600 SeqID_121609 SeqID_120880 SeqID_120956 SeqID_121015 SeqID_121055 SeqID_121119 SeqID_121160 SeqID_123601 SeqID_123673 SeqID_123785 SeqID_123791 SeqID_123809 SeqID_123819 SeqID_123820 SeqID_123839 SeqID_121697 SeqID_124070 SeqID_124091 SeqID_124152 SeqID_124176 SeqID_124194 SeqID_124259 SeqID_121731 SeqID_121748 SeqID_121845 SeqID_121882 SeqID_121928 SeqID_121933 SeqID_123529 SeqID_119158 SeqID_119196 SeqID_119491 SeqID_119569 SeqID_119713 SeqID_119816 SeqID_120343 | Immunoglobulin I-set domain |
| TBC | SeqID_119295 SeqID_119731 SeqID_121193 | TBC domain |
| Calpain_III | SeqID_120374 | Calpain large subunit, domain III |
| CBFD_NFYB_HMF | SeqID_121234 SeqID_122039 SeqID_122046 SeqID_122119 SeqID_122455 SeqID_122483 SeqID_122582 SeqID_122688 SeqID_122744 SeqID_122766 SeqID_122771 SeqID_121314 SeqID_123003 SeqID_123317 SeqID_123463 SeqID_123473 SeqID_121448 SeqID_121446 SeqID_119330 SeqID_119493 SeqID_119512 SeqID_119521 SeqID_119609 SeqID_119776 SeqID_121479 SeqID_121482 SeqID_120790 SeqID_121601 SeqID_123744 SeqID_121643 SeqID_121663 SeqID_121675 SeqID_121684 SeqID_121688 SeqID_121706 SeqID_124105 SeqID_124164 SeqID_124258 SeqID_124262 SeqID_124276 SeqID_121771 SeqID_121809 SeqID_121823 SeqID_121905 | Histone-like transcription factor (CBF/ |
| UDPG_MGDP_dh_C | SeqID_123494 | UDP-glucose/GDP-mannose dehydrogenase |
| zf-UBP | SeqID_122511 SeqID_122662 SeqID_120244 | Zn-finger in ubiquitin-hydrolases and other |
| UPF0184 | SeqID_122379 SeqID_123860 | Uncharacterised protein family (UPF0184) |
| FF | SeqID_121478 SeqID_120846 SeqID_121180 | FF domain |
| Rhodanese | SeqID_123181 SeqID_123269 | Rhodanese-like domain |
| TBP | SeqID_120108 SeqID_121146 SeqID_121734 | Transcription factor TFIID (or TATA-binding |
| Cytochrom_C1 | SeqID_119212 | Cytochrome C1 family |
| PI-PLC-Y | SeqID_120248 | Phosphatidylinositol-specific phospholipase |

TABLE 1-continued

SCN GENE FAMILIES and ANNOTATIONS
SCN gene families

| Gene name | SCN gene family members | Protein annotation |
|---|---|---|
| Glycolytic | SeqID_121242 SeqID_121268 SeqID_122585 SeqID_121503 SeqID_120227 SeqID_120758 SeqID_123730 SeqID_124335 SeqID_121856 | Fructose-bisphosphate aldolase class-I |
| COX15-CtaA | SeqID_119736 | Cytochrome oxidase assembly |
| Actin | SeqID_121231 SeqID_121257 SeqID_122239 SeqID_122271 SeqID_122678 SeqID_122922 SeqID_122921 SeqID_122940 SeqID_122974 SeqID_122977 SeqID_122985 SeqID_123092 SeqID_123347 SeqID_123374 SeqID_123381 SeqID_123376 SeqID_123378 SeqID_123388 SeqID_123397 SeqID_123394 SeqID_123402 SeqID_119184 SeqID_121411 SeqID_119898 SeqID_121581 SeqID_121592 SeqID_123541 SeqID_123542 SeqID_123817 SeqID_123843 SeqID_121690 SeqID_124081 SeqID_124084 SeqID_124093 SeqID_124188 SeqID_124303 SeqID_121834 SeqID_121888 SeqID_121911 | Actin |
| ATP_synt_H | SeqID_122810 SeqID_120261 SeqID_124197 | ATP synthase subunit H |
| SET | SeqID_122866 SeqID_123437 SeqID_119452 SeqID_119703 SeqID_121141 | SET domain |
| Ribosomal_L5_C | SeqID_121970 SeqID_122399 SeqID_122665 SeqID_123116 SeqID_123183 SeqID_120376 SeqID_123547 SeqID_124178 | ribosomal L5P family C-terminus |
| ADK_lid | SeqID_121282 SeqID_122317 | Adenylate kinase, active site lid |
| GrpE | SeqID_122071 SeqID_123157 SeqID_123878 SeqID_121526 SeqID_120867 SeqID_123661 SeqID_121743 | GrpE |
| XRN_N | SeqID_122345 SeqID_121207 SeqID_124106 | XRN 5'-3' exonuclease N-terminus |
| Ribosomal_L1 | SeqID_122679 SeqID_122715 SeqID_124062 | Ribosomal protein L1p/L10e family |
| RhoGEF | SeqID_122254 SeqID_120745 | RhoGEF domain |
| Y_phosphatase | SeqID_123060 SeqID_119220 SeqID_119686 SeqID_119866 SeqID_119975 SeqID_120184 SeqID_120234 SeqID_120792 SeqID_121037 SeqID_121036 SeqID_121105 | Protein-tyrosine phosphatase |
| Ribosomal_L2 | SeqID_122387 SeqID_122576 SeqID_119709 SeqID_121219 SeqID_123662 SeqID_124015 SeqID_121891 | Ribosomal Proteins L2, RNA binding dom |
| 7tm_1 | SeqID_119786 | 7 transmembrane receptor (rhodopsin family) |
| Ribosomal_L3 | SeqID_122659 SeqID_122727 SeqID_123246 SeqID_121145 SeqID_123585 | Ribosomal protein L3 |
| Sdh_cyt | SeqID_122442 SeqID_123881 | Succinate dehydrogenase cytochrome b subunit |
| DNA_topoisoIV | SeqID_120500 | DNA gyrase/topoisomerase IV, subunit A |
| 7tm_2 | SeqID_120113 | 7 transmembrane receptor (Secretin family) |
| Ribosomal_L4 | SeqID_122113 SeqID_122385 SeqID_121324 SeqID_122845 SeqID_121127 SeqID_123536 SeqID_123727 | Ribosomal protein L4/L1 family |
| 7tm_3 | SeqID_120501 SeqID_120729 SeqID_120999 | 7 transmembrane receptor (metabotropic gluta |
| Ribosomal_L5 | SeqID_121970 SeqID_122399 SeqID_122665 SeqID_122908 SeqID_123116 SeqID_123183 | Ribosomal protein L5 |

TABLE 1-continued

SCN GENE FAMILIES and ANNOTATIONS
SCN gene families

| Gene name | SCN gene family members | Protein annotation |
|---|---|---|
| | SeqID_123517 SeqID_123547 SeqID_124178 | |
| PAPS_reduct | SeqID_120874 | Phosphoadenosine phosphosulfate reductase |
| Ribosomal_L6 | SeqID_122583 SeqID_123234 SeqID_121602 SeqID_120932 SeqID_123631 | Ribosomal protein L6 |
| ADAM_spacer1 | SeqID_119479 | ADAM-TS Spacer 1 |
| HSP90 | SeqID_121981 SeqID_122028 SeqID_122738 SeqID_121524 SeqID_120445 SeqID_120787 SeqID_121577 SeqID_123813 SeqID_121774 SeqID_121829 SeqID_121895 | HSP90 protein |
| Abhydrolase_1 | SeqID_119405 SeqID_121610 | alpha/beta hydrolase fold |
| Peptidase_M1 | SeqID_120743 SeqID_120851 | Peptidase family M1 |
| Herpes_LP | SeqID_120428 | Herpesvirus leader protein |
| Pescadillo_N | SeqID_122934 | Pescadillo N-terminus |
| Abhydrolase_3 | SeqID_119940 SeqID_120282 SeqID_120891 | alpha/beta hydrolase fold |
| CPSase_L_chain | SeqID_119260 SeqID_119619 | Carbamoyl-phosphate synthase L chain, |
| PMI_typeI | SeqID_122372 SeqID_123985 | Phosphomannose isomerase type I |
| Glyco_hydro_18 | SeqID_122290 SeqID_119433 SeqID_123731 SeqID_124053 | Glycosyl hydrolases family 18 |
| Profilin | SeqID_122484 SeqID_120556 SeqID_123780 SeqID_121762 SeqID_121862 | Profilin |
| RIO1 | SeqID_120808 | RIO1 family |
| TCTP | SeqID_122571 SeqID_123113 SeqID_121485 SeqID_120084 SeqID_120085 SeqID_123959 | Translationally controlled tumour protein |
| NTF2 | SeqID_122143 SeqID_123505 SeqID_123530 SeqID_119273 SeqID_120761 | Nuclear transport factor 2 (NTF2) domain |
| AP_endonuc_2 | SeqID_120685 | Xylose isomerase-like TIM barrel |
| GATase_2 | SeqID_122634 SeqID_119643 SeqID_123847 | Glutamine amidotransferases class-II |
| RRS1 | SeqID_122559 SeqID_122857 SeqID_123569 | Ribosome biogenesis regulatory protein (RRS1 |
| Gln-synt_C | SeqID_122482 SeqID_120289 | Glutamine synthetase, catalytic domain |
| Pribosyltran | SeqID_122656 SeqID_122880 SeqID_120272 SeqID_124138 | Phosphoribosyl transferase domain |
| DUF367 | SeqID_120808 | Domain of unknown function (DUF367) |
| PWP2 | SeqID_121293 | Periodic tryptophan protein 2 WD repeat asso |
| RNA_pol_Rpa2_4 | SeqID_119390 | RNA polymerase I, Rpa2 specific domain |
| HesB | SeqID_123420 | HesB-like domain |
| SPRY | SeqID_122960 SeqID_119817 | SPRY domain |
| COX4 | SeqID_122622 SeqID_122739 SeqID_121444 SeqID_121470 SeqID_120419 SeqID_121605 SeqID_123898 SeqID_121775 | Cytochrome c oxidase subunit IV |
| Gp-FAR-1 | SeqID_122790 SeqID_123533 SeqID_120157 SeqID_123934 SeqID_124215 | Nematode fatty acid retinoid binding protein |
| Gln-synt_N | SeqID_122482 SeqID_123792 | Glutamine synthetase, beta-Grasp domain |
| Transketolase_C | SeqID_119346 | Transketolase, C-terminal domain |
| Ctr | SeqID_119988 | Ctr copper transporter family |
| RCC1 | SeqID_122092 SeqID_120326 SeqID_123910 | Regulator of chromosome condensation (RCC1) |
| Pkinase_Tyr | SeqID_121233 SeqID_121271 SeqID_122086 SeqID_122117 SeqID_122221 SeqID_122233 SeqID_122285 SeqID_122384 SeqID_122470 SeqID_122618 SeqID_122687 SeqID_122758 SeqID_123026 SeqID_123421 SeqID_123491 SeqID_119148 SeqID_121409 SeqID_121416 SeqID_119206 SeqID_119219 | Protein tyrosine kinase |

TABLE 1-continued

SCN GENE FAMILIES and ANNOTATIONS
SCN gene families

| Gene name | SCN gene family members | Protein annotation |
|---|---|---|
| | SeqID_119238 SeqID_119245 | |
| | SeqID_119296 SeqID_119338 | |
| | SeqID_119410 SeqID_119412 | |
| | SeqID_119422 SeqID_119436 | |
| | SeqID_119453 SeqID_119472 | |
| | SeqID_119483 SeqID_119520 | |
| | SeqID_119525 SeqID_119541 | |
| | SeqID_119728 SeqID_119764 | |
| | SeqID_119789 SeqID_119828 | |
| | SeqID_120006 SeqID_120051 | |
| | SeqID_120126 SeqID_120166 | |
| | SeqID_120298 SeqID_120406 | |
| | SeqID_120418 SeqID_120428 | |
| | SeqID_120452 SeqID_120453 | |
| | SeqID_120550 SeqID_120636 | |
| | SeqID_120663 SeqID_120672 | |
| | SeqID_120772 SeqID_121622 | |
| | SeqID_120934 SeqID_120996 | |
| | SeqID_121189 SeqID_123672 | |
| | SeqID_123838 SeqID_123977 | |
| | SeqID_123989 SeqID_124109 | |
| | SeqID_124294 SeqID_121714 | |
| | SeqID_121742 SeqID_121803 | |
| | SeqID_121897 SeqID_121907 | |
| OSCP | SeqID_122390 SeqID_123173 | ATP synthase delta (OSCP) |
| | SeqID_123852 SeqID_121694 | subunit |
| Ham1p_like | SeqID_120320 | Ham1 family |
| Transketolase_N | SeqID_122651 SeqID_119261 | Transketolase, thiamine |
| | SeqID_123846 | diphosphate b |
| HD | SeqID_119514 SeqID_119787 | HD domain |
| MreB_Mbl | SeqID_121224 SeqID_121246 | MreB/Mbl protein |
| | SeqID_121258 SeqID_121266 | |
| | SeqID_122340 SeqID_119310 | |
| | SeqID_120675 SeqID_123580 | |
| Fzo_mitofusin | SeqID_119682 | fzo-like conserved region |
| GCFC | SeqID_120111 | GC-rich sequence DNA-binding factor-like pro |
| DER1 | SeqID_123172 SeqID_120680 | Der1-like family |
| Phosphorylase | SeqID_120862 | Carbohydrate phosphorylase |
| SH2 | SeqID_122470 SeqID_123228 | SH2 domain |
| | SeqID_119500 SeqID_120234 | |
| | SeqID_120452 SeqID_120453 | |
| | SeqID_120921 SeqID_120958 | |
| CXC | SeqID_121122 | Tesmin/TSO1-like CXC domain |
| Aldedh | SeqID_120628 | Aldehyde dehydrogenase family |
| CK_II_beta | SeqID_120267 | Casein kinase II regulatory subunit |
| ERM | SeqID_121435 SeqID_121811 | Ezrin/radixin/moesin family |
| 3HCDH_N | SeqID_122892 SeqID_119503 | 3-hydroxyacyl-CoA |
| | SeqID_120447 | dehydrogenase, NAD binding |
| Troponin | SeqID_121972 SeqID_122915 | Troponin |
| | SeqID_123477 SeqID_120512 | |
| | SeqID_123537 | |
| zf-U1 | SeqID_122257 SeqID_122817 | U1 zinc finger |
| | SeqID_119881 | |
| Dynamin_M | SeqID_121459 SeqID_121020 | Dynamin central region |
| LBP_BPI_CETP_C | SeqID_121024 | LBP/BPI/CETP family, C-terminal do |
| UBA | SeqID_122024 SeqID_122255 | UBA/TS-N domain |
| | SeqID_122435 SeqID_122689 | |
| | SeqID_120244 SeqID_123742 | |
| | SeqID_123895 SeqID_121722 | |
| | SeqID_121739 | |
| Dynamin_N | SeqID_122325 SeqID_119276 | Dynamin family |
| | SeqID_119682 SeqID_121020 | |
| | SeqID_123830 | |
| FG-GAP | SeqID_120791 | FG-GAP repeat |
| Supt5 | SeqID_119904 | Supt5 repeat |
| CHORD | SeqID_122778 SeqID_121480 | CHORD |
| | SeqID_120611 SeqID_124127 | |
| Ribosomal_S6e | SeqID_122091 SeqID_122108 | Ribosomal protein S6e |
| | SeqID_123156 SeqID_123278 | |
| | SeqID_123328 SeqID_123341 | |
| | SeqID_123427 SeqID_119761 | |
| | SeqID_123571 SeqID_124292 | |

TABLE 1-continued

SCN GENE FAMILIES and ANNOTATIONS
SCN gene families

| Gene name | SCN gene family members | Protein annotation |
|---|---|---|
| Gtr1_RagA | SeqID_123193 SeqID_121217 | Gtr1/RagA G protein conserved region |
| CAF1 | SeqID_122750 SeqID_123054 SeqID_123367 SeqID_124146 SeqID_121735 | CAF1 family ribonuclease |
| RNA_pol_Rpb6 | SeqID_122713 SeqID_120963 SeqID_124170 | RNA polymerase Rpb6 |
| Hist_deacetyl | SeqID_122658 SeqID_120496 SeqID_124304 | Histone deacetylase domain |
| RNA_pol_Rpb8 | SeqID_122008 SeqID_122789 SeqID_119393 SeqID_123747 | RNA polymerase Rpb8 |
| Ribosomal_L10e | SeqID_122247 SeqID_122929 SeqID_123115 SeqID_123302 SeqID_123354 SeqID_121429 SeqID_119804 SeqID_123702 SeqID_121800 SeqID_121851 | Ribosomal L10 |
| DUF1127 | SeqID_121449 | Domain of unknown function (DUF1127) |
| FARP | SeqID_121261 SeqID_122785 | FMRFamide related peptide family |
| ubiquitin | SeqID_121249 SeqID_121259 SeqID_121959 SeqID_121966 SeqID_121974 SeqID_121987 SeqID_122018 SeqID_122017 SeqID_122021 SeqID_122020 SeqID_122023 SeqID_122026 SeqID_122033 SeqID_122042 SeqID_122053 SeqID_122150 SeqID_122234 SeqID_122256 SeqID_122415 SeqID_122461 SeqID_122550 SeqID_122647 SeqID_122726 SeqID_122768 SeqID_121317 SeqID_121325 SeqID_122784 SeqID_122823 SeqID_123207 SeqID_123316 SeqID_123462 SeqID_123488 SeqID_123500 SeqID_119205 SeqID_121408 SeqID_121458 SeqID_119321 SeqID_119375 SeqID_119457 SeqID_119597 SeqID_119702 SeqID_119857 | Ubiquitin family |
| mRNA_cap_enzyme | SeqID_123044 SeqID_120040 | mRNA capping enzyme, catalytic domain |
| Ribosomal_60s | SeqID_122215 SeqID_122490 SeqID_123784 SeqID_124059 | 60s Acidic ribosomal protein |
| SHMT | SeqID_123444 | Serine hydroxymethyltransferase |
| TSP_1 | SeqID_121277 SeqID_119765 SeqID_121174 | Thrombospondin type 1 domain |
| Bin3 | SeqID_122035 SeqID_120646 SeqID_123803 | Bicoid-interacting protein 3 (Bin3) |
| APS_kinase | SeqID_119710 | Adenylylsulphate kinase |
| GSH_synthase | SeqID_122183 SeqID_119391 SeqID_120121 SeqID_120409 SeqID_120622 SeqID_120719 SeqID_120886 SeqID_120895 SeqID_121074 SeqID_123719 | Eukaryotic glutathione synthase |
| SFT2 | SeqID_123142 SeqID_121421 SeqID_120229 | SFT2-like protein |
| Homeobox | SeqID_119358 SeqID_119397 SeqID_119915 SeqID_120364 SeqID_120535 SeqID_121140 | Homeobox domain |
| Pox_A_type_inc | SeqID_121260 SeqID_122546 SeqID_123618 | Viral A-type inclusion protein repeat |
| iPGM_N | SeqID_122467 SeqID_123844 SeqID_120794 | BPG-independent PGAM N-terminus (iPGM_N) |
| RNA_pol_L | SeqID_122755 SeqID_120230 SeqID_123595 | RNA polymerase Rpb3/Rpb11 dimerisation doma |
| V-set | SeqID_123529 SeqID_119196 SeqID_119491 SeqID_119713 SeqID_119816 SeqID_120343 | Immunoglobulin V-set domain |
| CTP_synth_N | SeqID_122680 SeqID_120279 SeqID_120818 SeqID_123812 | CTP synthase N-terminus |
| AAA | SeqID_122138 SeqID_122219 SeqID_122276 SeqID_122358 SeqID_122493 SeqID_122675 SeqID_121315 SeqID_121378 | ATPase family associated with various cellul |

TABLE 1-continued

SCN GENE FAMILIES and ANNOTATIONS
SCN gene families

| Gene name | SCN gene family members | Protein annotation |
|---|---|---|
| | SeqID_123161 SeqID_119176 | |
| | SeqID_121460 SeqID_119267 | |
| | SeqID_119300 SeqID_119612 | |
| | SeqID_119652 SeqID_119734 | |
| | SeqID_119875 SeqID_120119 | |
| | SeqID_120736 SeqID_121618 | |
| | SeqID_120857 SeqID_120931 | |
| | SeqID_120938 SeqID_123801 | |
| | SeqID_123871 SeqID_124113 | |
| | SeqID_124117 SeqID_121875 | |
| | SeqID_121923 | |
| PP-binding | SeqID_123286 SeqID_123525 | Phosphopantetheine attachment site |
| | SeqID_120461 SeqID_124213 | |
| | SeqID_124214 | |
| CDC37 | SeqID_120246 | Cdc37 family |
| FtsJ | SeqID_120165 | FtsJ-like methyltransferase |
| Peroxin-13_N | SeqID_119323 | Peroxin 13, N-terminal |
| Ribosomal_S7e | SeqID_122524 SeqID_121334 | Ribosomal protein S7e |
| | SeqID_123124 SeqID_121922 | |
| Sugar_tr | SeqID_119607 SeqID_120612 | Sugar (and other) transporter |
| UCH | SeqID_122246 SeqID_122435 | Ubiquitin carboxyl-terminal hydrolase |
| | SeqID_122511 SeqID_121433 | |
| | SeqID_119366 SeqID_119785 | |
| | SeqID_119799 SeqID_120244 | |
| | SeqID_120577 SeqID_121090 | |
| | SeqID_123828 SeqID_123895 | |
| | SeqID_121784 | |
| HATPase_c | SeqID_121965 SeqID_121968 | Histidine kinase-, DNA gyrase B-, and HSP90 |
| | SeqID_121976 SeqID_122028 | |
| | SeqID_122252 SeqID_123282 | |
| | SeqID_124089 SeqID_120445 | |
| | SeqID_123704 | |
| Activin_recp | SeqID_123267 | Activin types I and II receptor domain |
| DUF602 | SeqID_119868 | Protein of unknown function, DUF602 |
| DUF1136 | SeqID_119196 | Repeat of unknown function (DUF1136) |
| TAFII28 | SeqID_123141 | hTAFII28-like protein conserved region |
| Pkinase | SeqID_121233 SeqID_121271 | Protein kinase domain |
| | SeqID_122086 SeqID_122117 | |
| | SeqID_122221 SeqID_122233 | |
| | SeqID_122285 SeqID_122384 | |
| | SeqID_122470 SeqID_122502 | |
| | SeqID_122618 SeqID_122687 | |
| | SeqID_122758 SeqID_122956 | |
| | SeqID_123026 SeqID_123491 | |
| | SeqID_119148 SeqID_121409 | |
| | SeqID_121416 SeqID_121441 | |
| | SeqID_119219 SeqID_119237 | |
| | SeqID_119238 SeqID_119245 | |
| | SeqID_119296 SeqID_119338 | |
| | SeqID_119365 SeqID_119410 | |
| | SeqID_119412 SeqID_119436 | |
| | SeqID_119453 SeqID_119472 | |
| | SeqID_119483 SeqID_119520 | |
| | SeqID_119525 SeqID_119576 | |
| | SeqID_119629 SeqID_119728 | |
| | SeqID_119764 SeqID_119789 | |
| | SeqID_119828 SeqID_119968 | |
| | SeqID_120006 SeqID_120126 | |
| | SeqID_120166 SeqID_120208 | |
| | SeqID_120298 SeqID_120406 | |
| | SeqID_120428 SeqID_120452 | |
| | SeqID_120453 SeqID_120550 | |
| | SeqID_120636 SeqID_120663 | |
| | SeqID_120672 SeqID_120701 | |
| | SeqID_120771 SeqID_120772 | |
| | SeqID_121561 SeqID_121583 | |
| | SeqID_121622 SeqID_120796 | |
| | SeqID_120934 SeqID_120996 | |
| | SeqID_121102 SeqID_121189 | |
| | SeqID_123672 SeqID_123947 | |
| | SeqID_123977 SeqID_123989 | |

TABLE 1-continued

SCN GENE FAMILIES and ANNOTATIONS
SCN gene families

| Gene name | SCN gene family members | Protein annotation |
|---|---|---|
| KH_1 | SeqID_124109 SeqID_124130 SeqID_124294 SeqID_121714 SeqID_121742 SeqID_121803 SeqID_121897 SeqID_121903 SeqID_121907 SeqID_121920 SeqID_122074 SeqID_122460 SeqID_121313 SeqID_123392 SeqID_123476 SeqID_119195 SeqID_120972 SeqID_124132 SeqID_121787 | KH domain |
| FA_hydroxylase | SeqID_122136 SeqID_123602 | Fatty acid hydroxylase |
| Clc-like | SeqID_122446 SeqID_120339 SeqID_120721 SeqID_123875 | Clc-like |
| KH_2 | SeqID_122074 SeqID_122370 SeqID_123179 SeqID_121535 SeqID_121549 SeqID_123699 SeqID_124132 SeqID_124172 SeqID_124328 SeqID_121787 | KH domain |
| Galactosyl_T_2 | SeqID_122573 SeqID_122681 SeqID_119322 SeqID_124349 | Galactosyltransferase |
| Piwi | SeqID_121243 SeqID_121305 SeqID_123411 SeqID_119347 SeqID_119676 SeqID_120129 SeqID_121773 SeqID_121792 | Piwi domain |
| RLI | SeqID_122076 SeqID_120449 SeqID_120808 SeqID_124131 | Possible metal-binding domain in RNase L inh |
| HORMA | SeqID_121286 SeqID_119567 SeqID_121728 | HORMA domain |
| RNA_pol_Rpb1_3 | SeqID_120039 SeqID_120437 SeqID_120506 | RNA polymerase Rpb1, domain 3 |
| Ldh_2 | SeqID_122223 SeqID_121410 SeqID_121556 SeqID_121574 SeqID_124002 | Malate/L-lactate dehydrogenase |
| Neuralized | SeqID_122352 SeqID_120365 SeqID_124000 SeqID_124184 | Neuralized |
| RNA_pol_Rpb1_4 | SeqID_120039 SeqID_120437 SeqID_120506 SeqID_120541 | RNA polymerase Rpb1, domain 4 |
| RNA_pol_Rpb1_5 | SeqID_120506 | RNA polymerase Rpb1, domain 5 |
| RNA_pol_Rpb1_6 | SeqID_120506 | RNA polymerase Rpb1, domain 6 |
| Clat_adaptor_s | SeqID_122102 SeqID_122224 SeqID_122801 SeqID_122988 SeqID_120385 SeqID_120859 SeqID_121131 SeqID_123790 SeqID_124166 | Clathrin adaptor complex small chain |
| IF4E | SeqID_122412 SeqID_120589 | Eukaryotic initiation factor 4E |
| Kinesin | SeqID_121296 SeqID_122362 SeqID_119669 SeqID_124181 | Kinesin motor domain |
| G10 | SeqID_122515 | G10 protein |
| Ground-like | SeqID_120751 | Ground-like domain |
| P34-Arc | SeqID_123215 SeqID_121855 | Arp2/3 complex, 34 kD subunit p34-Arc |
| Ribosomal_S8e | SeqID_122003 SeqID_122010 SeqID_122130 SeqID_122508 SeqID_121333 SeqID_123027 SeqID_121508 SeqID_121531 SeqID_121545 SeqID_123644 SeqID_121667 | Ribosomal protein S8e |
| Ribosomal_S3_C | SeqID_122370 SeqID_123179 SeqID_119376 SeqID_121535 SeqID_121126 SeqID_123699 | Ribosomal protein S3, C-terminal domai |
| ResIII | SeqID_122318 SeqID_119170 SeqID_121443 SeqID_119233 SeqID_119766 SeqID_120168 SeqID_123835 SeqID_124119 | Type III restriction enzyme, res subunit |
| TFIIE_beta | SeqID_121012 | TFIIE beta subunit core domain |
| AA_kinase | SeqID_122430 | Amino acid kinase family |
| Exo_endo_phos | SeqID_122447 SeqID_123874 | Endonuclease/Exonuclease/phosphatase fa |
| HLH | SeqID_122206 SeqID_119868 SeqID_120631 | Helix-loop-helix DNA-binding domain |

TABLE 1-continued

SCN GENE FAMILIES and ANNOTATIONS
SCN gene families

| Gene name | SCN gene family members | Protein annotation |
|---|---|---|
| Keratin_B2 | SeqID_120481 | Keratin, high sulfur B2 protein |
| TspO_MBR | SeqID_122231 SeqID_122587 SeqID_123338 SeqID_121431 SeqID_119499 SeqID_123778 SeqID_123779 SeqID_124344 SeqID_121908 | TspO/MBR family |
| C1-set | SeqID_119491 SeqID_120343 | Immunoglobulin C1-set domain |
| SCO1-SenC | SeqID_121873 | SCO1/SenC |
| T-box | SeqID_122717 SeqID_123320 | T-box |
| PSI | SeqID_119510 | Plexin repeat |
| AAA_2 | SeqID_122219 SeqID_122276 SeqID_121378 SeqID_119652 SeqID_119734 SeqID_121618 SeqID_120931 SeqID_123871 SeqID_124113 SeqID_121923 | ATPase family associated with various cellul |
| DUF477 | SeqID_122322 SeqID_124018 | Domain of unknown function (DUF477) |
| AAA_3 | SeqID_122493 SeqID_119176 SeqID_119742 SeqID_119875 SeqID_120649 SeqID_121618 | ATPase family associated with various cellul |
| ABC_membrane | SeqID_120493 | ABC transporter transmembrane region |
| fn3 | SeqID_119158 SeqID_119225 SeqID_119569 SeqID_120170 SeqID_120951 SeqID_121023 | Fibronectin type III domain |
| AAA_5 | SeqID_122219 SeqID_122493 SeqID_119176 SeqID_119875 SeqID_120649 SeqID_120763 SeqID_120931 SeqID_120936 SeqID_123871 | ATPase family associated with various cellul |
| Destabilase | SeqID_122806 SeqID_124205 | Destabilase |
| Glyco_transf_22 | SeqID_123460 SeqID_120564 | Alg9-like mannosyltransferase family |
| Not3 | SeqID_122203 SeqID_121162 | Not1 N-terminal domain, CCR4-Not complex com |
| CDC50 | SeqID_122266 SeqID_121335 SeqID_120160 SeqID_123808 | LEM3 (ligand-effect modulator 3) family/CD |
| Glyco_transf_25 | SeqID_121052 | Glycosyltransferase family 25 (LPS bi |
| PSS | SeqID_119991 | Phosphatidyl serine synthase |
| PRP38 | SeqID_123506 SeqID_121713 | PRP38 family |
| UCR_14kD | SeqID_122477 SeqID_121481 SeqID_121514 SeqID_123716 | Ubiquinol-cytochrome C reductase complex 14k |
| Biopterin_H | SeqID_122189 SeqID_122692 SeqID_122958 SeqID_120567 SeqID_123832 SeqID_124293 | Biopterin-dependent aromatic amino acid h |
| Cofilin_ADF | SeqID_122563 SeqID_122620 SeqID_121306 SeqID_121419 SeqID_119918 SeqID_124332 | Cofilin/tropomyosin-type actin-binding pr |
| MOZ_SAS | SeqID_123033 | MOZ/SAS family |
| SNase | SeqID_121415 SeqID_120155 | Staphylococcal nuclease homologue |
| Skp1_POZ | SeqID_121262 SeqID_122339 SeqID_122672 SeqID_121318 SeqID_119994 SeqID_123642 | Skp1 family, tetramerisation domain |
| Acyl_transf_3 | SeqID_119415 | Acyltransferase family |
| Ribosomal_L10 | SeqID_123472 SeqID_120199 SeqID_121812 | Ribosomal protein L10 |
| HMA | SeqID_122636 SeqID_123900 | Heavy-metal-associated domain |
| Ribosomal_S3Ae | SeqID_122253 SeqID_123202 SeqID_119906 SeqID_121492 SeqID_123962 | Ribosomal S3Ae family |
| Ribosomal_L11 | SeqID_122466 SeqID_122612 SeqID_122798 SeqID_120200 SeqID_121603 SeqID_120902 SeqID_123787 SeqID_121653 SeqID_124218 | Ribosomal protein L11, RNA binding do |
| eIF-1a | SeqID_122566 SeqID_123523 SeqID_119774 SeqID_124173 | Eukaryotic initiation factor 1A |
| Ribosomal_L13e | SeqID_121985 SeqID_121989 SeqID_122082 SeqID_119425 SeqID_123942 | Ribosomal protein L13e |
| Ribosomal_L12 | SeqID_122236 SeqID_121124 SeqID_123921 | Ribosomal protein L7/L12 C-terminal dom |

TABLE 1-continued

SCN GENE FAMILIES and ANNOTATIONS
SCN gene families

| Gene name | SCN gene family members | Protein annotation |
|---|---|---|
| S10_plectin | SeqID_122608 SeqID_119224 SeqID_123551 | Plectin/S10 domain |
| Ribosomal_L14 | SeqID_122293 SeqID_123957 | Ribosomal protein L14p/L23e |
| DUF625 | SeqID_120752 | Protein of unknown function (DUF625) |
| Sec23_trunk | SeqID_121381 SeqID_119647 | Sec23/Sec24 trunk domain |
| ig | SeqID_123529 SeqID_119196 SeqID_119491 SeqID_119569 SeqID_119713 SeqID_119816 SeqID_120343 | Immunoglobulin domain |
| Ribosomal_L16 | SeqID_122247 SeqID_122653 SeqID_123302 SeqID_124211 | Ribosomal protein L16 |
| Ion_trans | SeqID_119930 SeqID_120812 | Ion transport protein |
| NAF1 | SeqID_119903 | NAF1 domain |
| Aa_trans | SeqID_121971 SeqID_119531 | Transmembrane amino acid transporter protein |
| APG6 | SeqID_122694 SeqID_121500 | Autophagy protein Apg6 |
| SEC-C | SeqID_120562 | SEC-C motif |
| KE2 | SeqID_122599 SeqID_122773 SeqID_124174 SeqID_124230 SeqID_124235 | KE2 family protein |
| Lyase_1 | SeqID_120948 SeqID_121661 SeqID_121786 | Lyase |
| Ran_BP1 | SeqID_119729 SeqID_120815 | RanBP1 domain |
| PGM_PMM_IV | SeqID_119474 SeqID_120700 | Phosphoglucomutase/phosphomannomutase, C-t |
| BAH | SeqID_123089 | BAH domain |
| UQ_con | SeqID_121983 SeqID_122089 SeqID_122437 SeqID_122519 SeqID_122757 SeqID_123232 | Ubiquitin-conjugating enzyme |
| ENTH | SeqID_122942 SeqID_123389 | ENTH domain |
| DUF6 | SeqID_119240 | Integral membrane protein DUF6 |
| Ribosomal_L21e | SeqID_122144 SeqID_123108 SeqID_123268 SeqID_123293 SeqID_123298 SeqID_121434 SeqID_119745 SeqID_123751 SeqID_124341 SeqID_121876 | Ribosomal protein L21e |
| Cyclin_C | SeqID_120722 | Cyclin, C-terminal domain |
| ADK | SeqID_121282 SeqID_122317 SeqID_119710 | Adenylate kinase |
| MAS20 | SeqID_121991 SeqID_122410 SeqID_123936 | MAS20 protein import receptor |
| TIG | SeqID_122994 | IPT/TIG domain |
| DNA_pol_B | SeqID_120301 | DNA polymerase family B |
| Ribosomal_L22 | SeqID_121995 SeqID_122261 SeqID_122840 SeqID_123164 SeqID_123257 SeqID_121516 SeqID_120038 SeqID_123674 | Ribosomal protein L22p/L17e |
| Ribosomal_L14e | SeqID_122701 SeqID_123548 | Ribosomal protein L14 |
| Ribosomal_L23 | SeqID_122038 SeqID_123046 SeqID_119380 SeqID_119408 SeqID_123694 SeqID_124231 | Ribosomal protein L23 |
| SNF2_N | SeqID_119766 SeqID_120168 SeqID_120323 | SNF2 family N-terminal domain |
| Cgr1 | SeqID_122506 SeqID_123609 | Cgr1 family |
| Glutaredoxin | SeqID_123129 | Glutaredoxin |
| PUA | SeqID_122707 SeqID_119847 | PUA domain |
| tRNA_m1G_MT_9 | SeqID_122151 SeqID_123209 | tRNA m(1)G methyltransferase |
| RNA_pol_Rpb2_3 | SeqID_123375 SeqID_121089 | RNA polymerase Rpb2, domain 3 |
| Ribosomal_L29 | SeqID_122312 SeqID_122610 SeqID_123285 SeqID_119200 SeqID_123638 SeqID_123687 SeqID_121725 | Ribosomal L29 protein |
| RNA_pol_Rpb2_4 | SeqID_123375 SeqID_121089 | RNA polymerase Rpb2, domain 4 |
| zf-nanos | SeqID_121133 | Nanos RNA binding domain |
| RNA_pol_Rpb2_5 | SeqID_122280 SeqID_119390 SeqID_121089 SeqID_124072 | RNA polymerase Rpb2, domain 5 |
| Peptidase_S8 | SeqID_121230 SeqID_123401 SeqID_119631 | Subtilase family |
| PUF | SeqID_122211 SeqID_122825 SeqID_119161 SeqID_121389 SeqID_123824 SeqID_121723 | Pumilio-family RNA binding repeat |

TABLE 1-continued

SCN GENE FAMILIES and ANNOTATIONS
SCN gene families

| Gene name | SCN gene family members | Protein annotation |
| --- | --- | --- |
| RNA_pol_Rpb2_6 | SeqID_122280 SeqID_122552 SeqID_121330 SeqID_123182 SeqID_119390 SeqID_123587 SeqID_123831 | RNA polymerase Rpb2, domain 6 |
| Cyclin_N | SeqID_122428 SeqID_122670 SeqID_122816 SeqID_121486 SeqID_120722 SeqID_121612 SeqID_123768 SeqID_123905 | Cyclin, N-terminal domain |
| Mod_r | SeqID_123251 SeqID_123409 SeqID_120718 SeqID_123566 | Modifier of rudimentary (Mod(r)) protein |
| RNA_pol_Rpb2_7 | SeqID_122552 | RNA polymerase Rpb2, domain 7 |
| Ribosomal_L7Ae | SeqID_121269 SeqID_122134 SeqID_122180 SeqID_122335 SeqID_122367 SeqID_122404 SeqID_122604 SeqID_122718 SeqID_123155 SeqID_123294 SeqID_123455 SeqID_119560 SeqID_123888 SeqID_119859 SeqID_121504 SeqID_123633 SeqID_123660 SeqID_123698 SeqID_123927 SeqID_123935 SeqID_123992 SeqID_124144 | Ribosomal protein L7Ae/L30e/S12e/Gadd4 |
| POLO_box | SeqID_119828 SeqID_121022 | POLO box duplicated region |
| Nucleoporin2 | SeqID_120026 | Nucleoporin autopeptidase |
| zf-BED | SeqID_119515 | BED zinc finger |
| Ets | SeqID_119450 | Ets-domain |
| Ribosomal_S2 | SeqID_122439 SeqID_122525 SeqID_122923 SeqID_122995 SeqID_123127 SeqID_123308 SeqID_123382 SeqID_120337 SeqID_120668 SeqID_123668 SeqID_124044 | Ribosomal protein S2 |
| Rcd1 | SeqID_121351 SeqID_119153 | Cell differentiation family, Rcd1-like |
| Ribosomal_S4 | SeqID_121533 SeqID_121546 | Ribosomal protein S4/S9 N-terminal domai |
| GMC_oxred_C | SeqID_122311 | GMC oxidoreductase |
| Ribosomal_S5 | SeqID_122366 SeqID_123421 SeqID_123632 | Ribosomal protein S5, N-terminal domai |
| DUF1240 | SeqID_120294 | Protein of unknown function (DUF1240) |
| Topoisom_I | SeqID_123167 SeqID_121520 SeqID_121660 SeqID_121884 | Eukaryotic DNA topoisomerase I, catalytic |
| Ribosomal_S6 | SeqID_122928 SeqID_119470 | Ribosomal protein S6 |
| DUF1241 | SeqID_122262 SeqID_120893 | Protein of unknown function (DUF1241) |
| Ribosomal_S7 | SeqID_122487 SeqID_122488 SeqID_122733 SeqID_123383 SeqID_124307 SeqID_123688 SeqID_124272 | Ribosomal protein S7p/S5e |
| Ssl1 | SeqID_122605 SeqID_123911 SeqID_124066 SeqID_121741 | Ssl1-like |
| Ribosomal_S8 | SeqID_122779 SeqID_120839 | Ribosomal protein S8 |
| Nop52 | SeqID_122283 SeqID_120786 SeqID_121201 SeqID_124065 | Nucleolar protein, Nop52 |
| Ribosomal_L22e | SeqID_122791 SeqID_120882 | Ribosomal L22e protein family |
| Ribosomal_L30 | SeqID_121300 SeqID_122251 SeqID_122565 SeqID_123737 SeqID_123736 SeqID_121777 SeqID_121894 SeqID_121896 | Ribosomal protein L30p/L7e |
| AdoHcyase | SeqID_122459 SeqID_123859 | S-adenosyl-L-homocysteine hydrolase |
| Ribosomal_L15e | SeqID_121969 SeqID_122199 SeqID_123299 SeqID_119488 SeqID_119941 SeqID_120030 SeqID_123763 SeqID_123764 SeqID_124342 | Ribosomal L15 |
| V-ATPase_C | SeqID_120905 | V-ATPase subunit C |
| Proteasome | SeqID_121422 SeqID_121276 SeqID_121284 SeqID_121960 SeqID_121962 SeqID_122045 SeqID_122055 SeqID_122190 SeqID_122396 SeqID_122413 SeqID_122474 SeqID_122498 SeqID_121342 SeqID_122780 | Proteasome A-type and B-type |

TABLE 1-continued

SCN GENE FAMILIES and ANNOTATIONS
SCN gene families

| Gene name | SCN gene family members | Protein annotation |
|---|---|---|
| | SeqID_122803 SeqID_123336 | |
| | SeqID_123362 SeqID_123419 | |
| | SeqID_119278 SeqID_119909 | |
| | SeqID_121468 SeqID_120588 | |
| | SeqID_120924 SeqID_123604 | |
| | SeqID_123611 SeqID_123646 | |
| | SeqID_123681 SeqID_123825 | |
| | SeqID_124136 SeqID_124227 | |
| | SeqID_121889 | |
| GMC_oxred_N | SeqID_122311 SeqID_124037 | GMC oxidoreductase |
| PHF5 | SeqID_122542 SeqID_120850 | PHF5-like protein |
| | SeqID_123639 | |
| DNA_gyraseB | SeqID_120500 | DNA gyrase B |
| Cullin | SeqID_122420 SeqID_119796 | Cullin family |
| | SeqID_119797 SeqID_120045 | |
| | SeqID_123756 SeqID_120756 | |
| | SeqID_120773 SeqID_121682 | |
| | SeqID_121780 SeqID_121941 | |
| DUF572 | SeqID_119715 SeqID_120330 | Family of unknown function (DUF572) |
| FAA_hydrolase | SeqID_122355 SeqID_124011 | Fumarylacetoacetate (FAA) hydrolase fam |
| cNMP_binding | SeqID_119563 SeqID_121604 | Cyclic nucleotide-binding domain |
| V-ATPase_G | SeqID_122706 SeqID_123291 | Vacuolar (H+)-ATPase G subunit |
| | SeqID_119894 SeqID_119927 | |
| | SeqID_123872 | |
| V-ATPase_H | SeqID_120190 | V-ATPase subunit H |
| Epimerase | SeqID_119815 SeqID_120284 | NAD dependent epimerase/dehydratase family |
| | SeqID_121143 | |
| Lipase_2 | SeqID_119177 | Lipase (class 2) |
| Ribosomal_L39 | SeqID_122520 SeqID_122799 | Ribosomal L39 protein |
| HCNGP | SeqID_120697 SeqID_120698 | HCNGP-like protein |
| POP1 | SeqID_123216 | Ribonucleases P/MRP protein subunit POP1 |
| SMN | SeqID_122580 SeqID_124165 | Survival motor neuron protein (SMN) |
| ACPS | SeqID_122149 SeqID_124163 | 4'-phosphopantetheinyl transferase superfami |
| Lamp | SeqID_122690 SeqID_123937 | Lysosome-associated membrane glycoprotein (L |
| FragX_IP | SeqID_120422 | Cytoplasmic Fragile-X interacting family |
| Aminotran_1_2 | SeqID_122344 | Aminotransferase class I and II |
| ABC_tran | SeqID_122402 SeqID_119524 | ABC transporter |
| | SeqID_119625 SeqID_120769 | |
| | SeqID_123949 | |
| GRP | SeqID_119747 SeqID_120570 | Glycine rich protein family |
| Vps54 | SeqID_122919 SeqID_119956 | Vps54-like protein |
| Aph-1 | SeqID_122155 SeqID_123059 | Aph-1 protein |
| | SeqID_124013 | |
| Radical_SAM | SeqID_120962 | Radical SAM superfamily |
| Josephin | SeqID_122683 SeqID_123774 | Josephin |
| | SeqID_123928 | |
| EF1G | SeqID_122057 SeqID_123454 | Elongation factor 1 gamma, conserved domain |
| | SeqID_120547 SeqID_123557 | |
| Monooxygenase | SeqID_122333 SeqID_123771 | Monooxygenase |
| EXS | SeqID_120654 | EXS family |
| PCNA_C | SeqID_122062 SeqID_122819 | Proliferating cell nuclear antigen, C-termin |
| | SeqID_120167 | |
| Sad1_UNC | SeqID_119813 SeqID_120250 | Sad1/UNC-like C-terminal |
| AMP-binding | SeqID_123152 SeqID_120233 | AMP-binding enzyme |
| DIM1 | SeqID_123449 SeqID_124285 | Mitosis protein DIM1 |
| ATP_bind_1 | SeqID_122375 SeqID_122533 | Conserved hypothetical ATP binding protein |
| | SeqID_122872 SeqID_119782 | |
| | SeqID_123655 SeqID_123983 | |
| DUF652 | SeqID_122800 SeqID_119259 | Protein of unknown function, DUF652 |
| | SeqID_123553 SeqID_124216 | |
| PCNA_N | SeqID_122062 SeqID_122819 | Proliferating cell nuclear antigen, N-termin |
| | SeqID_122829 SeqID_121061 | |
| | SeqID_124283 | |
| DUF727 | SeqID_122615 SeqID_119316 | Protein of unknown function (DUF727) |
| | SeqID_121702 SeqID_124046 | |

TABLE 1-continued

SCN GENE FAMILIES and ANNOTATIONS
SCN gene families

| Gene name | SCN gene family members | Protein annotation |
|---|---|---|
| Utp11 | SeqID_122295 SeqID_121156 | Utp11 protein |
| ThiF | SeqID_121273 SeqID_122346 SeqID_119266 SeqID_121104 SeqID_124189 | ThiF family |
| MMR_HSR1 | SeqID_121288 SeqID_122204 SeqID_122360 SeqID_122375 SeqID_122392 SeqID_122397 SeqID_122560 SeqID_122575 SeqID_122579 SeqID_122600 SeqID_122619 SeqID_122657 SeqID_122671 SeqID_121329 SeqID_122792 SeqID_122872 SeqID_123422 SeqID_119204 SeqID_121430 SeqID_119311 SeqID_119332 SeqID_119352 SeqID_119367 SeqID_119492 SeqID_119523 SeqID_119645 SeqID_119791 SeqID_120413 SeqID_120523 SeqID_120766 SeqID_121613 SeqID_120900 SeqID_121038 SeqID_121093 SeqID_123568 SeqID_123726 SeqID_123740 SeqID_123754 SeqID_121709 SeqID_123960 SeqID_123950 SeqID_123988 SeqID_123991 SeqID_124180 SeqID_121717 SeqID_121740 | GTPase of unknown function |
| zf-C2H2 | SeqID_122179 SeqID_122249 SeqID_122267 SeqID_123033 SeqID_123091 SeqID_123110 SeqID_123191 SeqID_119156 SeqID_119250 SeqID_119283 SeqID_119315 SeqID_119326 SeqID_119455 SeqID_119515 SeqID_119638 SeqID_119674 SeqID_119915 SeqID_119925 SeqID_120046 SeqID_120117 SeqID_120617 SeqID_120707 SeqID_121133 SeqID_121172 SeqID_123906 SeqID_123914 SeqID_124145 SeqID_121781 SeqID_121822 | Zinc finger, C2H2 type |
| HEAT | SeqID_122200 SeqID_122532 SeqID_121374 SeqID_121380 SeqID_122870 SeqID_119166 SeqID_121402 SeqID_119389 SeqID_119427 SeqID_119658 SeqID_124126 SeqID_119790 SeqID_119852 SeqID_119929 SeqID_121537 SeqID_119998 SeqID_120055 SeqID_120163 SeqID_120538 SeqID_120549 SeqID_120581 SeqID_120656 SeqID_121550 SeqID_121614 SeqID_121006 SeqID_121175 SeqID_121201 SeqID_123600 SeqID_121708 | HEAT repeat |
| PWI | SeqID_122736 SeqID_122749 SeqID_120835 SeqID_124267 SeqID_124270 | PWI domain |
| Syja_N | SeqID_119649 SeqID_120216 | Sac1 homology domain |
| zf-Sec23_Sec24 | SeqID_120593 | Sec23/Sec24 zinc finger |
| Gcd10p | SeqID_122163 SeqID_119505 SeqID_124154 | Gcd10p family |
| Gelsolin | SeqID_119286 SeqID_121187 | Gelsolin repeat |
| FUN14 | SeqID_122589 | FUN14 family |
| UcrQ | SeqID_122007 SeqID_122808 SeqID_119696 SeqID_124290 | UcrQ family |
| Ribosomal_L31e | SeqID_122378 SeqID_123337 SeqID_123982 | Ribosomal protein L31e |
| Ribosomal_L24e | SeqID_122132 SeqID_123616 SeqID_123617 SeqID_124161 | Ribosomal protein L24e |
| Calreticulin | SeqID_122265 SeqID_122837 SeqID_119911 SeqID_123897 | Calreticulin family |

TABLE 1-continued

SCN GENE FAMILIES and ANNOTATIONS
SCN gene families

| Gene name | SCN gene family members | Protein annotation |
|---|---|---|
| eIF-5a | SeqID_122554 SeqID_123204 SeqID_120378 SeqID_123582 | Eukaryotic initiation factor 5A hypusine, DN |
| Pex14_N | SeqID_122174 SeqID_123766 | Peroxisomal membrane anchor protein (Pex14p) |
| DUF663 | SeqID_123123 SeqID_120018 | Protein of unknown function (DUF663) |
| UIM | SeqID_122683 SeqID_123389 SeqID_123774 | Ubiquitin interaction motif |
| COX5A | SeqID_122529 SeqID_120371 SeqID_123670 | Cytochrome c oxidase subunit Va |
| COX5B | SeqID_121281 SeqID_122395 SeqID_122479 SeqID_121428 SeqID_119688 SeqID_123743 SeqID_124156 | Cytochrome c oxidase subunit Vb |
| Ribosomal_L23eN | SeqID_122038 SeqID_123046 SeqID_119380 SeqID_119408 SeqID_123694 | Ribosomal protein L23, N-terminal dom |
| PH | SeqID_121274 SeqID_123067 SeqID_119258 SeqID_119463 SeqID_120842 SeqID_120929 SeqID_121878 | PH domain |
| GTP_EFTU_D2 | SeqID_122391 SeqID_122657 SeqID_121299 SeqID_122792 SeqID_123334 SeqID_123345 SeqID_119311 SeqID_119352 SeqID_121538 SeqID_121551 SeqID_120413 SeqID_120540 SeqID_123754 SeqID_123950 SeqID_123967 SeqID_121805 SeqID_121825 SeqID_121826 | Elongation factor Tu domain 2 |
| Sas10_Utp3 | SeqID_120054 | Sas10/Utp3 family |
| Prp18 | SeqID_123355 SeqID_120394 | Prp18 domain |
| GTP_EFTU_D3 | SeqID_122729 SeqID_122792 SeqID_123334 SeqID_123345 SeqID_121538 SeqID_121551 SeqID_120413 SeqID_123754 SeqID_121664 SeqID_121825 SeqID_121826 SeqID_121939 | Elongation factor Tu C-terminal domain |
| GATA | SeqID_121080 | GATA zinc finger |
| Spectrin | SeqID_119246 SeqID_119482 SeqID_119575 SeqID_120539 SeqID_120627 | Spectrin repeat |
| V-SNARE | SeqID_122066 SeqID_121095 SeqID_123939 | Vesicle transport v-SNARE protein |
| Ribosomal_S5_C | SeqID_122366 SeqID_123632 SeqID_121839 | Ribosomal protein S5, C-terminal domai |
| PX | SeqID_120853 | PX domain |
| KID | SeqID_120763 | KID repeat |
| GSH_synth_ATP | SeqID_122183 SeqID_121436 SeqID_120021 SeqID_120101 SeqID_120121 SeqID_120409 SeqID_120622 SeqID_120666 SeqID_120719 SeqID_120782 SeqID_120886 SeqID_120895 SeqID_121074 SeqID_123719 | Eukaryotic glutathione synthase, ATP bi |
| MCM | SeqID_119742 SeqID_119912 SeqID_120936 | MCM2/3/5 family |
| ETF_alpha | SeqID_121607 | Electron transfer flavoprotein alpha subuni |
| L51_S25_CI-B8 | SeqID_122048 SeqID_123231 SeqID_121114 SeqID_123645 | Mitochondrial ribosomal protein L51/S |
| CBS | SeqID_120735 SeqID_121213 | CBS domain |
| Ribosomal_L18e | SeqID_122342 SeqID_122374 SeqID_123713 SeqID_123753 SeqID_121703 SeqID_124289 | Eukaryotic ribosomal protein L18 |
| OTCace | SeqID_119435 | Aspartate/ornithine carbamoyltransferase, A |
| GRAM | SeqID_122481 SeqID_123794 SeqID_121636 | GRAM domain |
| Rad21_Rec8 | SeqID_122963 | Conserved region of Rad21/Rec8 like prot |
| DUF676 | SeqID_120421 | Putative serine esterase (DUF676) |
| Ribosomal_L18p | SeqID_120495 SeqID_121687 | Ribosomal L18p/L5e family |

TABLE 1-continued

SCN GENE FAMILIES and ANNOTATIONS
SCN gene families

| Gene name | SCN gene family members | Protein annotation |
| --- | --- | --- |
| Metallophos | SeqID_122191 SeqID_122213 SeqID_122289 SeqID_123311 SeqID_123307 SeqID_121426 SeqID_119337 SeqID_119448 SeqID_119502 SeqID_119572 SeqID_119659 SeqID_119751 SeqID_119860 SeqID_121540 SeqID_120128 SeqID_120238 SeqID_120434 SeqID_120484 SeqID_120553 SeqID_120710 SeqID_120825 SeqID_120824 SeqID_120834 SeqID_120873 SeqID_121046 SeqID_121142 SeqID_121188 SeqID_121700 SeqID_124029 SeqID_124030 SeqID_124061 SeqID_121738 SeqID_121746 SeqID_121770 SeqID_121899 SeqID_121900 SeqID_121915 | Calcineurin-like phosphoesterase |
| HECT | SeqID_121283 SeqID_121316 SeqID_119865 SeqID_120854 SeqID_121657 SeqID_121712 | HECT-domain (ubiquitin-transferase) |
| Hormone_recep | SeqID_120699 SeqID_121758 | Ligand-binding domain of nuclear hormon |
| NAC | SeqID_122153 SeqID_122689 SeqID_123502 SeqID_120888 SeqID_123742 | NAC domain |
| C1_1 | SeqID_120222 SeqID_120526 | Phorbol esters/diacylglycerol binding domain |
| Calponin | SeqID_121222 SeqID_122248 SeqID_122936 SeqID_123005 SeqID_123171 SeqID_123188 SeqID_123400 SeqID_120392 SeqID_120928 SeqID_120927 SeqID_123804 SeqID_123842 SeqID_123853 SeqID_124187 | Calponin family repeat |
| RmaAD | SeqID_122723 SeqID_119487 SeqID_123996 | Ribosomal RNA adenine dimethylase |
| SPX | SeqID_120654 | SPX domain |
| C1_3 | SeqID_119379 SeqID_120217 SeqID_120788 | C1-like domain |
| GST_C | SeqID_122057 SeqID_122407 SeqID_122628 SeqID_122642 SeqID_121383 SeqID_123011 SeqID_121623 SeqID_121132 SeqID_123557 SeqID_123625 SeqID_123709 SeqID_123708 SeqID_124298 SeqID_121838 | Glutathione S-transferase, C-terminal domain |
| Na_Ca_ex | SeqID_120053 | Sodium/calcium exchanger protein |
| B3_4 | SeqID_120243 | B3/4 domain |
| Sec23_helical | SeqID_119286 | Sec23/Sec24 helical domain |
| Ribosomal_L40e | SeqID_122033 SeqID_121408 SeqID_119857 SeqID_123721 | Ribosomal L40e family |
| ICIn_channel | SeqID_121998 SeqID_123531 | Nucleotide-sensitive chloride conductanc |
| Histone | SeqID_121234 SeqID_122039 SeqID_122046 SeqID_122096 SeqID_122119 SeqID_122455 SeqID_122483 SeqID_122582 SeqID_122688 SeqID_122744 SeqID_122766 SeqID_122771 SeqID_121314 SeqID_122884 SeqID_122955 SeqID_123003 SeqID_123317 SeqID_123463 SeqID_123466 SeqID_123473 SeqID_121448 SeqID_121446 SeqID_119330 SeqID_119493 SeqID_119512 SeqID_119521 SeqID_119609 SeqID_119776 SeqID_119983 SeqID_121479 SeqID_121482 SeqID_120068 SeqID_120077 SeqID_120480 SeqID_120534 SeqID_120790 SeqID_121570 SeqID_121594 SeqID_121601 SeqID_120813 | Core histone H2A/H2B/H3/H4 |

TABLE 1-continued

SCN GENE FAMILIES and ANNOTATIONS
SCN gene families

| Gene name | SCN gene family members | Protein annotation |
|---|---|---|
| | SeqID_121054 SeqID_123744 | |
| | SeqID_121645 SeqID_121663 | |
| | SeqID_121675 SeqID_121683 | |
| | SeqID_121684 SeqID_121688 | |
| | SeqID_121706 SeqID_121705 | |
| | SeqID_124105 SeqID_124164 | |
| | SeqID_124258 SeqID_124262 | |
| | SeqID_124276 SeqID_124314 | |
| | SeqID_121771 SeqID_121809 | |
| | SeqID_121819 SeqID_121828 | |
| | SeqID_121823 SeqID_121905 | |
| Disintegrin | SeqID_120481 | Disintegrin |
| 3HCDH | SeqID_120447 | 3-hydroxyacyl-CoA dehydrogenase, C-terminal |
| NAP | SeqID_122303 SeqID_119982 SeqID_124050 | Nucleosome assembly protein (NAP) |
| Tubulin | SeqID_122269 SeqID_122332 SeqID_122440 SeqID_121336 SeqID_123013 SeqID_119381 SeqID_119720 SeqID_124114 SeqID_121499 SeqID_121506 SeqID_121543 SeqID_120775 SeqID_121555 SeqID_123545 SeqID_123884 SeqID_124069 SeqID_121761 SeqID_121820 SeqID_121849 SeqID_121893 | Tubulin/FtsZ family, GTPase domain |
| GST_N | SeqID_122057 SeqID_122407 SeqID_122628 SeqID_122642 SeqID_121383 SeqID_123011 SeqID_123274 SeqID_119360 SeqID_121496 SeqID_120438 SeqID_121623 SeqID_123557 SeqID_123625 SeqID_123709 SeqID_123708 SeqID_124297 SeqID_121838 | Glutathione S-transferase, N-terminal domain |
| ETC_C1_NDUFA5 | SeqID_122406 SeqID_123873 | ETC complex I subunit conserved region |
| 2-Hacid_dh | SeqID_120275 | D-isomer specific 2-hydroxyacid dehydrogen |
| Adenylsucc_synt | SeqID_122272 SeqID_121355 SeqID_119162 SeqID_119650 SeqID_120090 SeqID_120822 SeqID_124006 | Adenylosuccinate synthetase |
| RTC | SeqID_122518 SeqID_123729 | RNA 3'-terminal phosphate cyclase |
| Ribosomal_L19e | SeqID_122613 SeqID_122869 SeqID_123303 SeqID_120779 | Ribosomal protein L19e |
| TRAPP_Bet3 | SeqID_122875 | Transport protein particle (TRAPP) compone |
| SMC_C | SeqID_119625 | SMC family, C-terminal domain |
| CDP-OH_P_transf | SeqID_123356 | CDP-alcohol phosphatidyltransferase |
| Frataxin_Cyay | SeqID_122075 SeqID_123508 SeqID_120847 SeqID_124330 | Frataxin-like domain |
| VHS | SeqID_120912 | VHS domain |
| DUF689 | SeqID_122204 | Protein of unknown function (DUF689) |
| SMC_N | SeqID_119887 SeqID_119966 SeqID_120574 SeqID_120702 | RecF/RecN/SMC N terminal domain |
| PTPLA | SeqID_120767 | Protein tyrosine phosphatase-like protein, P |
| PfkB | SeqID_122553 SeqID_123583 | pfkB family carbohydrate kinase |
| DSPc | SeqID_122616 SeqID_122746 SeqID_124323 SeqID_119299 SeqID_119527 SeqID_120116 SeqID_123836 SeqID_124056 | Dual specificity phosphatase, catalytic doma |
| Biotin_lipoyl | SeqID_120976 | Biotin-requiring enzyme |
| Pkinase_C | SeqID_122758 SeqID_122978 SeqID_119365 SeqID_121625 SeqID_120796 | Protein kinase C terminal domain |
| DAD | SeqID_119716 | DAD family |
| Alpha_adaptin_C | SeqID_120950 | Alpha adaptin AP2, C-terminal domain |
| Ribosomal_L6e | SeqID_122489 SeqID_122949 SeqID_121011 SeqID_123683 | Ribosomal protein L6e |

TABLE 1-continued

SCN GENE FAMILIES and ANNOTATIONS
SCN gene families

| Gene name | SCN gene family members | Protein annotation |
| --- | --- | --- |
| S1 | SeqID_122067 SeqID_123689 SeqID_123690 | S1 RNA binding domain |
| Oxidored_q6 | SeqID_121980 SeqID_122154 SeqID_119667 SeqID_124082 | NADH ubiquinone oxidoreductase, 20 Kd sub |
| Extensin_2 | SeqID_120572 SeqID_120593 SeqID_120713 | Extensin-like region |
| Gar1 | SeqID_119747 | Gar1 protein RNA binding region |
| S4 | SeqID_122623 SeqID_121533 SeqID_121546 SeqID_120098 SeqID_124001 | S4 domain |
| Bromodomain | SeqID_119794 | Bromodomain |
| Laminin_N | SeqID_119297 SeqID_119335 | Laminin N-terminal (Domain VI) |
| CDI | SeqID_122878 | Cyclin-dependent kinase inhibitor |
| Mago_nashi | SeqID_123521 SeqID_120904 | Mago nashi protein |
| SNF7 | SeqID_122586 SeqID_119719 SeqID_119746 SeqID_120690 SeqID_121136 SeqID_124098 | SNF7 |
| ShTK | SeqID_122581 SeqID_119601 SeqID_120015 SeqID_120669 | ShTK domain |
| tRNA_anti | SeqID_122633 SeqID_120602 SeqID_124327 | OB-fold nucleic acid binding domain |
| Linker_histone | SeqID_122931 SeqID_120058 | linker histone H1 and H5 family |
| DAO | SeqID_122333 SeqID_122338 SeqID_122411 SeqID_120662 SeqID_121620 SeqID_123933 | FAD dependent oxidoreductase |
| NDUF_B7 | SeqID_120001 SeqID_122009 SeqID_122777 SeqID_123519 SeqID_123938 SeqID_124080 | NADH-ubiquinone oxidoreductase B18 subunit ( |
| Ribosomal_L34e | SeqID_122631 SeqID_123111 SeqID_123332 SeqID_119760 SeqID_123896 | Ribosomal protein L34e |
| DUF906 | SeqID_119497 | Domain of Unknown Function (DUF906) |
| SPC12 | SeqID_122753 SeqID_121566 SeqID_121590 SeqID_124248 | Microsomal signal peptidase 12 kDa subunit ( |
| CLN3 | SeqID_123346 SeqID_120607 SeqID_120681 | CLN3 protein |
| RVT_1 | SeqID_119187 SeqID_119374 SeqID_119417 SeqID_119451 SeqID_119461 SeqID_119462 SeqID_119508 SeqID_119566 SeqID_119662 SeqID_119663 SeqID_119834 SeqID_119855 SeqID_119943 SeqID_120004 SeqID_120103 SeqID_120138 SeqID_120352 SeqID_120433 SeqID_120465 SeqID_120471 SeqID_120546 SeqID_120566 SeqID_120586 SeqID_120687 SeqID_120716 SeqID_120852 SeqID_120935 SeqID_121043 SeqID_121058 SeqID_121128 SeqID_121129 SeqID_121179 | Reverse transcriptase (RNA-dependent DNA pol |
| Gp_dh_C | SeqID_121978 SeqID_122147 SeqID_121379 SeqID_121400 SeqID_121457 SeqID_119718 SeqID_123607 | Glyceraldehyde 3-phosphate dehydrogenase, C- |
| Ldi_recept_b | SeqID_119985 SeqID_120019 | Low-density lipoprotein receptor repeat |
| F_actin_cap_B | SeqID_122095 SeqID_123254 SeqID_123555 | F-actin capping protein, beta subunit |
| Methyltransf_8 | SeqID_122377 SeqID_119368 SeqID_123981 | Hypothetical methyltransferase |
| Mt_ATP-synt_B | SeqID_122761 SeqID_120653 SeqID_124245 SeqID_121789 | Mitochondrial ATP synthase B chain prec |
| KAP_NTPase | SeqID_120368 | KAP family P-loop domain |
| Mt_ATP-synt_D | SeqID_122314 SeqID_123912 | ATP synthase D chain, mitochondrial (AT |

TABLE 1-continued

SCN GENE FAMILIES and ANNOTATIONS
SCN gene families

| Gene name | SCN gene family members | Protein annotation |
|---|---|---|
| SAC3_GANP | SeqID_121169 | SAC3/GANP family |
| Gp_dh_N | SeqID_121986 SeqID_122098 SeqID_122147 SeqID_123064 SeqID_123079 SeqID_123357 SeqID_123457 SeqID_121379 SeqID_121457 SeqID_123840 SeqID_123607 SeqID_123870 SeqID_124339 SeqID_121930 | Glyceraldehyde 3-phosphate dehydrogenase, NA |
| An_peroxidase | SeqID_120092 SeqID_120241 SeqID_120906 | Animal haem peroxidase |
| Ephrin | SeqID_119824 | Ephrin |
| polyprenyl_synt | SeqID_120635 | Polyprenyl synthetase |
| Neur_chan_memb | SeqID_121005 SeqID_121087 | Neurotransmitter-gated ion-channel tra |
| zf-NPL4 | SeqID_123465 SeqID_119522 | NPL4 family, putative zinc binding region |
| XAP5 | SeqID_122814 SeqID_122850 SeqID_121167 | XAP5 protein |
| RNA_pol | SeqID_120255 | DNA-dependent RNA polymerase |
| NMT_C | SeqID_121407 SeqID_120382 | Myristoyl-CoA: protein N-myristoyltransferase |
| Aldose_epim | SeqID_122507 SeqID_120204 SeqID_123603 | Aldose 1-epimerase |
| DUF841 | SeqID_120243 | Eukaryotic protein of unknown function (DUF8 |
| Mov34 | SeqID_121290 SeqID_121294 SeqID_122120 SeqID_122260 SeqID_122735 SeqID_121344 SeqID_122844 SeqID_123535 SeqID_121382 SeqID_121417 SeqID_119999 SeqID_120711 SeqID_123682 SeqID_121693 SeqID_124040 SeqID_124087 SeqID_121736 | Mov34/MPN/PAD-1 family |
| NAD_binding_1 | SeqID_122444 SeqID_123823 | Oxidoreductase NAD-binding domain |
| Ribosomal_L28e | SeqID_122648 SeqID_120682 SeqID_123720 | Ribosomal L28e protein family |
| LIM | SeqID_122321 SeqID_123039 SeqID_123158 SeqID_123185 SeqID_119388 SeqID_119555 SeqID_119701 SeqID_120218 SeqID_123816 SeqID_121638 SeqID_124168 | LIM domain |
| SPC25 | SeqID_122737 SeqID_124254 | Microsomal signal peptidase 25 kDa subunit ( |
| WGR | SeqID_121544 | WGR domain |
| STT3 | SeqID_120152 | Oligosaccharyl transferase STT3 subun |
| WH2 | SeqID_119377 | WH2 motif |
| 14-3-3 | SeqID_122166 SeqID_122862 SeqID_123514 SeqID_119268 SeqID_119536 SeqID_119605 | 14-3-3 protein |
| Alpha_adaptinC2 | SeqID_120950 | Adaptin C-terminal domain |
| CbiA | SeqID_122680 | CobQ/CobB/MinD/ParA nucleotide binding do |
| zf-MIZ | SeqID_120096 | MIZ zinc finger |
| Lipocalin | SeqID_122101 SeqID_122172 SeqID_123222 SeqID_119931 SeqID_120164 SeqID_123572 SeqID_123598 SeqID_121698 | Lipocalin/cytosolic fatty-acid binding pr |
| DLIC | SeqID_122981 | Dynein light intermediate chain (DLIC) |
| tRNA-synt_1c_C | SeqID_120890 | tRNA synthetases class I (E and Q), an |
| Bestrophin | SeqID_119636 | Bestrophin |
| eIF-3_zeta | SeqID_122685 SeqID_120237 SeqID_123560 | Eukaryotic translation initiation factor 3 |
| Porin_3 | SeqID_122330 SeqID_121328 SeqID_119190 SeqID_121557 SeqID_121575 SeqID_123999 | Eukaryotic porin |
| ARID | SeqID_120573 | ARID/BRIGHT DNA binding domain |

TABLE 1-continued

SCN GENE FAMILIES and ANNOTATIONS
SCN gene families

| Gene name | SCN gene family members | Protein annotation |
|---|---|---|
| CybS | SeqID_122786 SeqID_124202 | CybS |
| BCAS2 | SeqID_122510 SeqID_123556 | Breast carcinoma amplified sequence 2 (BCAS2 |
| Motile_Sperm | SeqID_122721 SeqID_123310 SeqID_119174 SeqID_119175 SeqID_119281 SeqID_119604 SeqID_119641 SeqID_119724 SeqID_120035 SeqID_120095 SeqID_120327 SeqID_120441 SeqID_120517 SeqID_120563 SeqID_120632 SeqID_120633 SeqID_120910 SeqID_124175 SeqID_121850 | MSP (Major sperm protein) domain |
| Transket_pyr | SeqID_122651 SeqID_119346 SeqID_120804 SeqID_120844 SeqID_123846 | Transketolase, pyridine binding domai |
| Fibrillarin | SeqID_123301 SeqID_119795 | Fibrillarin |
| PABP | SeqID_122526 SeqID_121469 SeqID_123820 SeqID_121869 | Poly-adenylate binding protein, unique domai |
| BRCT | SeqID_121491 SeqID_120459 SeqID_121621 | BRCA1 C Terminus (BRCT) domain |
| Psf2 | SeqID_119632 | Partner of SLD five, PSF2 |
| tRNA-synt_1 | SeqID_123431 SeqID_119678 SeqID_121502 | tRNA synthetases class I (I, L, M and V) |
| Psf3 | SeqID_122668 SeqID_123586 | Partner of SLD five, PSF3 |
| tRNA-synt_2 | SeqID_122301 SeqID_124123 SeqID_119833 SeqID_124052 SeqID_121567 SeqID_121591 SeqID_121045 | tRNA synthetases class II (D, K and N) |
| NDK | SeqID_121977 SeqID_122294 SeqID_121345 SeqID_123201 SeqID_123452 SeqID_123451 SeqID_121388 SeqID_123559 | Nucleoside diphosphate kinase |
| ATP-synt_DE_N | SeqID_122751 SeqID_121401 SeqID_124264 SeqID_123752 | ATP synthase, Delta/Epsilon chain, beta |
| zf-C4 | SeqID_122310 SeqID_122617 SeqID_122812 SeqID_123080 SeqID_123445 SeqID_119666 SeqID_120699 SeqID_120820 SeqID_124333 | Zinc-finger, C4 type (two domains) |
| DIRP | SeqID_119217 | DIRP |
| Ribosomal_L36e | SeqID_122112 SeqID_123552 | Ribosomal protein L36e |
| Filament | SeqID_121260 SeqID_122400 SeqID_122546 SeqID_123386 SeqID_119327 SeqID_121473 SeqID_120922 SeqID_123579 SeqID_123618 SeqID_123953 | Intermediate filament protein |
| TFIID_30kDa | SeqID_120863 | Transcription initiation factor TFIID 23- |
| DUF926 | SeqID_120692 | Domain of Unknown Function (DUF926) |
| DUF854 | SeqID_119289 SeqID_120777 | *Caenorhabditis elegans* repeat of unknown fun |
| TPP_enzyme_M | SeqID_120595 | Thiamine pyrophosphate enzyme, central d |
| PPI_Ypi1 | SeqID_122389 SeqID_120052 SeqID_123885 | Protein phosphatase inhibitor |
| Myosin_head | SeqID_119861 | Myosin head (motor domain) |
| MH1 | SeqID_122197 SeqID_123448 SeqID_121021 | MH1 domain |
| RWD | SeqID_122537 SeqID_120442 | RWD domain |
| DUF858 | SeqID_122961 | Eukaryotic protein of unknown function (DUF8 |
| 3Beta_HSD | SeqID_123272 SeqID_121396 SeqID_119630 SeqID_121143 | 3-beta hydroxysteroid dehydrogenase/isomera |
| BIR | SeqID_123175 SeqID_119442 SeqID_121665 | Inhibitor of Apoptosis domain |
| MTHFR | SeqID_122188 SeqID_120829 SeqID_124115 | Methylenetetrahydrofolate reductase |
| GYF | SeqID_121994 | GYF domain |
| E1_dh | SeqID_122564 SeqID_122651 SeqID_123263 SeqID_123821 SeqID_123846 | Dehydrogenase E1 component |

TABLE 1-continued

SCN GENE FAMILIES and ANNOTATIONS
SCN gene families

| Gene name | SCN gene family members | Protein annotation |
| --- | --- | --- |
| Fork_head | SeqID_120305 | Fork head domain |
| DUF1604 | SeqID_119654 | Protein of unknown function (DUF1604) |
| OST3_OST6 | SeqID_123025 | OST3/OST6 family |
| Cadherin | SeqID_119235 SeqID_119705 | Cadherin domain |
| PPTA | SeqID_122418 SeqID_123390 SeqID_121057 SeqID_123924 | Protein prenyltransferase alpha subunit repe |
| GCV_H | SeqID_122462 SeqID_123213 SeqID_119530 | Glycine cleavage H-protein |
| Aldolase_II | SeqID_121238 SeqID_122401 SeqID_122499 SeqID_121462 SeqID_121475 SeqID_123767 SeqID_121689 SeqID_123952 SeqID_121934 | Class II Aldolase and Adducin N-terminal |
| AIG1 | SeqID_119367 | AIG1 family |
| RNase_PH | SeqID_122716 SeqID_122887 SeqID_120679 SeqID_124199 | 3' exoribonuclease family, domain 1 |
| Ribosomal_L18ae | SeqID_122646 SeqID_122664 SeqID_122858 SeqID_123114 SeqID_123121 SeqID_120878 SeqID_123624 SeqID_123886 SeqID_124236 SeqID_121791 SeqID_121797 SeqID_121925 | Ribosomal L18ae protein family |
| Nucleoside_tran | SeqID_123441 SeqID_124095 | Nucleoside transporter |
| Ribosomal_L37e | SeqID_122591 SeqID_121170 SeqID_123963 | Ribosomal protein L37e |
| Prefoldin | SeqID_120211 SeqID_123679 | Prefoldin subunit |
| Beta-lactamase | SeqID_122907 SeqID_120056 | Beta-lactamase |
| PC_rep | SeqID_122969 | Proteasome/cyclosome repeat |
| DEAD | SeqID_122207 SeqID_122277 SeqID_122318 SeqID_122319 SeqID_122381 SeqID_123007 SeqID_123018 SeqID_119170 SeqID_121414 SeqID_121443 SeqID_119233 SeqID_119256 SeqID_119300 SeqID_119324 SeqID_119657 SeqID_119712 SeqID_119766 SeqID_120168 SeqID_120342 SeqID_120509 SeqID_120575 SeqID_121032 SeqID_121200 SeqID_123835 SeqID_123976 SeqID_124021 SeqID_124074 SeqID_124119 | DEAD/DEAH box helicase |
| SURF4 | SeqID_120816 | SURF4 family |
| NCD3G | SeqID_120999 | Nine Cysteines Domain of family 3 GPCR |
| SURF6 | SeqID_122863 | Surfeit locus protein 6 |
| Sec10 | SeqID_120206 | Exocyst complex component Sec10 |
| Oxidored_molyb | SeqID_122426 SeqID_123908 | Oxidoreductase molybdopterin binding d |
| Cation_efflux | SeqID_119547 SeqID_119854 | Cation efflux family |
| HisKA_2 | SeqID_121848 | Histidine kinase |
| RNA_pol_Rpb5_C | SeqID_122441 SeqID_123528 SeqID_123883 | RNA polymerase Rpb5, C-terminal domain |
| dUTPase | SeqID_120762 | dUTPase |
| Calx-beta | SeqID_120919 | Calx-beta domain |
| FA_desaturase | SeqID_122220 SeqID_122258 | Fatty acid desaturase |
| BRF1 | SeqID_119280 | Brf1-like TBP-binding domain |
| W2 | SeqID_119265 SeqID_121487 | eIF4-gamma/eIF5/eIF2-epsilon |
| PIP5K | SeqID_123028 | Phosphatidylinositol-4-phosphate 5-Kinase |
| Ribosomal_L35Ae | SeqID_122114 SeqID_122827 SeqID_123435 SeqID_123889 SeqID_124288 | Ribosomal protein L35Ae |
| RTC_insert | SeqID_122518 SeqID_120776 SeqID_123973 | RNA 3'-terminal phosphate cyclase (RTC), i |
| SKIP_SNW | SeqID_121033 | SKIP/SNW domain |
| PAP_assoc | SeqID_122124 SeqID_123088 SeqID_120195 | PAP/25A associated domain |
| DNA_pol_E_B | SeqID_122568 SeqID_124351 | DNA polymerase epsilon subunit B |
| RNA_pol_Rpb5_N | SeqID_122441 SeqID_123137 SeqID_123528 SeqID_119977 SeqID_123883 | RNA polymerase Rpb5, N-terminal domain |

TABLE 1-continued

SCN GENE FAMILIES and ANNOTATIONS
SCN gene families

| Gene name | SCN gene family members | Protein annotation |
| --- | --- | --- |
| Vicilin_N | SeqID_121108 | Vicilin N terminal region |
| DEP | SeqID_120527 | Domain found in Dishevelled, Egl-10, and Ple |
| Cytochrom_C | SeqID_122036 SeqID_123651 | Cytochrome c |
| Ribosomal_L38e | SeqID_122040 SeqID_119735 SeqID_123834 | Ribosomal L38e protein family |
| GRIM-19 | SeqID_123149 SeqID_119221 SeqID_121885 | GRIM-19 protein |
| DUF947 | SeqID_120569 | Domain of unknown function (DUF947) |
| DnaJ | SeqID_121245 SeqID_122232 SeqID_122521 SeqID_122541 SeqID_122667 SeqID_122722 SeqID_119277 SeqID_119288 SeqID_119644 SeqID_120879 SeqID_120983 SeqID_121206 SeqID_123640 SeqID_123715 SeqID_123882 SeqID_124112 SeqID_124311 | DnaJ domain |
| G6PD_C | SeqID_122743 SeqID_124271 | Glucose-6-phosphate dehydrogenase, C-termina |
| PHO4 | SeqID_122752 SeqID_120810 SeqID_124256 | Phosphate transporter family |
| Reprolysin | SeqID_120801 | Reprolysin (M12B) family zinc metalloprote |
| MIT | SeqID_120407 | MIT domain |
| LRR_1 | SeqID_122148 SeqID_122601 SeqID_119275 SeqID_119350 SeqID_120299 SeqID_120639 SeqID_121187 SeqID_123576 SeqID_123887 | Leucine Rich Repeat |
| Ribosomal_S21e | SeqID_123512 SeqID_119578 SeqID_123570 | Ribosomal protein S21e |
| tRNA-synt_1d_C | SeqID_122724 | DALR anticodon binding domain |
| RNA_pol_A_bac | SeqID_120230 SeqID_121039 | RNA polymerase Rpb3/RpoA insert domain |
| KOW | SeqID_122127 SeqID_122516 SeqID_122554 SeqID_122701 SeqID_122710 SeqID_123295 SeqID_123458 SeqID_119904 SeqID_123548 SeqID_123582 SeqID_123634 SeqID_123734 | KOW motif |
| ECH | SeqID_122281 SeqID_122454 SeqID_119372 SeqID_123865 SeqID_124071 SeqID_121747 | Enoyl-CoA hydratase/isomerase family |
| IF_tail | SeqID_121260 SeqID_122400 SeqID_120920 SeqID_123579 | Intermediate filament tail domain |
| PAN | SeqID_120695 | PAN domain |
| zf-C3HC4 | SeqID_122347 SeqID_122496 SeqID_123384 SeqID_123511 SeqID_119241 SeqID_119357 SeqID_120644 SeqID_123692 SeqID_124075 | Zinc finger, C3HC4 type (RING finger) |
| WW | SeqID_122257 SeqID_122416 SeqID_119608 SeqID_120846 SeqID_120854 SeqID_123538 | WW domain |
| PB1 | SeqID_120217 | PB1 domain |
| NOG1 | SeqID_119367 | Nucleolar GTP-binding protein 1 (NOG1) |
| PAS | SeqID_122206 | PAS domain |
| EI24 | SeqID_121718 | Etoposide-induced protein 2.4 (EI24) |
| MIF4G | SeqID_120041 | MIF4G domain |
| PI3_PI4_kinase | SeqID_119291 SeqID_119922 SeqID_120521 SeqID_121582 SeqID_120853 SeqID_121831 | Phosphatidylinositol 3- and 4-kinase |
| PAZ | SeqID_121243 SeqID_119347 SeqID_119944 SeqID_121539 SeqID_120129 SeqID_121552 SeqID_121086 SeqID_121913 | PAZ domain |
| Cpn60_TCP1 | SeqID_122080 SeqID_122245 SeqID_123243 SeqID_123369 SeqID_119577 SeqID_119896 SeqID_121517 SeqID_120191 SeqID_120292 SeqID_120613 | TCP-1/cpn60 chaperonin family |

TABLE 1-continued

SCN GENE FAMILIES and ANNOTATIONS
SCN gene families

| Gene name | SCN gene family members | Protein annotation |
|---|---|---|
| Tim17 | SeqID_120876 SeqID_121091 SeqID_123615 SeqID_123735 SeqID_121655 SeqID_123955 SeqID_122097 SeqID_124320 SeqID_121063 | Tim17/Tim22/Tim23 family |
| Ligase_CoA | SeqID_122725 SeqID_124060 | CoA-ligase |
| Trehalase | SeqID_121616 | Trehalase |
| PQ-loop | SeqID_122891 SeqID_123245 SeqID_123591 | PQ loop repeat |
| TTL | SeqID_119185 | Tubulin-tyrosine ligase family |
| Myb_DNA-binding | SeqID_119288 SeqID_119345 SeqID_120201 SeqID_121080 SeqID_121197 | Myb-like DNA-binding domain |
| Ribonuclease_3 | SeqID_121044 | RNase3 domain |
| Ribophorin_I | SeqID_121320 SeqID_120333 SeqID_121666 | Ribophorin I |
| CAS_CSE1 | SeqID_119961 | CAS/CSE protein, C-terminus |
| Pex2_Pex12 | SeqID_122740 SeqID_123980 | Pex2/Pex12 amino terminal region |

Table 1 Legend:
Column 1 - pfam name or designation
Column 2 - gene family member listed by SEQ ID NO corresponding to amino acid sequence translation from vcDNA SEQ ID NO identified in feature field of peptide sequence
Column 3 - Protein annotation based on BLASTP comparisons In order to construct a dsRNA sequence, or concatamers or chimeras of dsRNA sequences from various genes either within SCN, from other pest nucleotide sequences, or a combination thereof, nucleotide sequences corresponding to the SCN genome sequences were BLASTed against known vertebrate, soybean, and *Rhizobium* nucleotide sequences to first eliminate contiguous sequences in SCN that matched sequences in known vertebrate, soybean, and *Rhozobium* sequences that are at least about 21 nucleotides in length. This redacted set of SCN sequences was then compared to known nucleotide sequences in parasitic nematodes, insects, and fungi to identify sequences of substantial identity that could be useful in constructing sequences that, when expressed as a dsRNA sequence, are capable of effecting gene suppression in SCN as well as in another parasitic nematode, or insect, or fungal pest. The results of comparisons to other parasitic nematode sequences are shown in Table 2.

TABLE 2

| Diverse Parasitic Nematode Nucleotide Coding Sequences Matching *H. glycines* vcDNA sequences | | | | |
|---|---|---|---|---|
| *H. glycines* Sequence[1] | Position[2] | GeneID[3] | Position[4] | % identity[5] |
| Seq ID NO: 50950 | 21-138 | gi\|28916076 | 1-119 | 91% |
| Seq ID NO: 50950 | 14-41 | gi\|159473 | 34-61 | 100% |
| Seq ID NO: 50950 | 14-41 | gi\|2454547 | 227-200 | 100% |
| Seq ID NO: 50950 | 14-41 | gi\|551594 | 194-221 | 100% |
| Seq ID NO: 50950 | 14-41 | gi\|551595 | 669-696 | 100% |
| Seq ID NO: 50950 | 14-41 | gi\|18032254 | 34-61 | 100% |
| Seq ID NO: 50950 | 18-41 | gi\|18477256 | 279-256 | 100% |
| Seq ID NO: 50950 | 18-41 | gi\|18477260 | 325-302 | 100% |
| Seq ID NO: 50950 | 18-41 | gi\|18477262 | 634-611 | 100% |
| Seq ID NO: 50950 | 14-35 | gi\|18477259 | 22-1 | 100% |
| Seq ID NO: 50950 | 14-35 | gi\|18477261 | 22-1 | 100% |
| Seq ID NO: 50950 | 14-35 | gi\|37780968 | 22-1 | 100% |
| Seq ID NO: 50973 | 88-108 | gi\|19267657 | 465-445 | 100% |
| Seq ID NO: 51012 | 302-411 | gi\|18080245 | 178-69 | 84% |
| Seq ID NO: 51132 | 182-360 | gi\|32323955 | 5-183 | 96% |
| Seq ID NO: 51132 | 184-359 | gi\|33139778 | 6-182 | 96% |
| Seq ID NO: 51132 | 182-351 | gi\|33140274 | 5-174 | 95% |
| Seq ID NO: 51132 | 195-360 | gi\|32324510 | 1-166 | 95% |

TABLE 2-continued

| Diverse Parasitic Nematode Nucleotide Coding Sequences Matching *H. glycines* vcDNA sequences | | | | |
|---|---|---|---|---|
| *H. glycines* Sequence[1] | Position[2] | GeneID[3] | Position[4] | % identity[5] |
| Seq ID NO: 51132 | 218-354 | gi\|33140264 | 1-137 | 95% |
| Seq ID NO: 51132 | 182-284 | gi\|32324219 | 5-107 | 94% |
| Seq ID NO: 51164 | 117-137 | gi\|22543645 | 32-12 | 100% |
| Seq ID NO: 51169 | 1-236 | gi\|47118285 | 740-975 | 97% |
| Seq ID NO: 51169 | 1-236 | gi\|47118286 | 753-988 | 97% |
| Seq ID NO: 51169 | 1-219 | gi\|16797830 | 731-950 | 97% |
| Seq ID NO: 51169 | 1-219 | gi\|21885260 | 751-969 | 97% |
| Seq ID NO: 51169 | 1-219 | gi\|26000759 | 727-945 | 97% |
| Seq ID NO: 51169 | 1-219 | gi\|31442322 | 728-946 | 97% |
| Seq ID NO: 51169 | 1-219 | gi\|31442320 | 728-946 | 96% |
| Seq ID NO: 51169 | 4-219 | gi\|16797831 | 732-947 | 96% |
| Seq ID NO: 51169 | 1-219 | gi\|38096133 | 730-948 | 94% |
| Seq ID NO: 51169 | 1-33 | gi\|16797827 | 776-807 | 96% |
| Seq ID NO: 51169 | 131-159 | gi\|16797844 | 862-890 | 96% |
| Seq ID NO: 51169 | 216-236 | gi\|48479719 | 1112-1132 | 100% |
| Seq ID NO: 51184 | 16-47 | gi\|32324419 | 271-302 | 100% |
| Seq ID NO: 51378 | 184-459 | gi\|32325335 | 36-311 | 97% |
| Seq ID NO: 51378 | 504-626 | gi\|32325335 | 311-433 | 100% |
| Seq ID NO: 51378 | 753-841 | gi\|32325335 | 453-541 | 97% |
| Seq ID NO: 51378 | 101-139 | gi\|32325335 | 1-39 | 100% |
| Seq ID NO: 51378 | 676-702 | gi\|32325335 | 430-456 | 100% |
| Seq ID NO: 51561 | 402-476 | gi\|33139584 | 80-6 | 100% |
| Seq ID NO: 51561 | 192-229 | gi\|33139584 | 115-78 | 100% |
| Seq ID NO: 51561 | 192-215 | gi\|6969910 | 34-11 | 100% |
| Seq ID NO: 51579 | 1-138 | gi\|33139914 | 209-346 | 97% |
| Seq ID NO: 51823 | 55-187 | gi\|18081060 | 80-212 | 86% |
| Seq ID NO: 51824 | 3-97 | gi\|54548889 | 100-194 | 87% |
| Seq ID NO: 51824 | 3-97 | gi\|18089540 | 421-515 | 85% |
| Seq ID NO: 51824 | 3-79 | gi\|18081060 | 404-480 | 87% |
| Seq ID NO: 51978 | 1-314 | gi\|33139071 | 85-397 | 96% |
| Seq ID NO: 51978 | 307-395 | gi\|33139071 | 406-494 | 97% |
| Seq ID NO: 51978 | 406-452 | gi\|33139071 | 505-551 | 97% |
| Seq ID NO: 51978 | 406-475 | gi\|32325389 | 507-576 | 97% |
| Seq ID NO: 51978 | 1-237 | gi\|33140521 | 87-323 | 94% |
| Seq ID NO: 51991 | 239-260 | gi\|30028357 | 64-85 | 100% |
| Seq ID NO: 52051 | 1-78 | gi\|33140098 | 496-573 | 100% |
| Seq ID NO: 52051 | 1-74 | gi\|32324423 | 496-569 | 100% |
| Seq ID NO: 52051 | 1-61 | gi\|33139933 | 499-559 | 100% |
| Seq ID NO: 52051 | 1-58 | gi\|33139533 | 495-552 | 100% |
| Seq ID NO: 52051 | 56-168 | gi\|18082418 | 136-248 | 85% |

TABLE 2-continued Diverse Parasitic Nematode Nucleotide Coding Sequences Matching *H. glycines* vcDNA sequences

| H. glycines Sequence[1] | Position[2] | Gene

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 54847 | 3-101 | gi\|28916076 | 176-79 | 89% |
| Seq ID NO: 54865 | 54-202 | gi\|33140673 | 199-51 | 88% |
| Seq ID NO: 54865 | 61-202 | gi\|33139639 | 245-386 | 88% |
| Seq ID NO: 54865 | 59-199 | gi\|33139131 | 99-239 | 86% |
| Seq ID NO: 45847 | 183-308 | gi\|18080348 | 231-356 | 85% |
| Seq ID NO: 45847 | 190-308 | gi\|7144294 | 198-316 | 85% |
| Seq ID NO: 54946 | 128-285 | gi\|54546846 | 415-257 | 85% |
| Seq ID NO: 54981 | 83-126 | gi\|551594 | 1028-1070 | 93% |
| Seq ID NO: 54981 | 83-126 | gi\|551595 | 267-309 | 93% |
| Seq ID NO: 54999 | 328-498 | gi\|18382277 | 801-971 | 82% |
| Seq ID NO: 55025 | 372-395 | gi\|33138439 | 263-286 | 100% |
| Seq ID NO: 55025 | 419-439 | gi\|33952838 | 448-428 | 100% |
| Seq ID NO: 55106 | 21-138 | gi\|28916076 | 1-119 | 91% |
| Seq ID NO: 55106 | 14-41 | gi\|159473 | 34-61 | 100% |
| Seq ID NO: 55106 | 14-41 | gi\|2454547 | 227-200 | 100% |
| Seq ID NO: 55106 | 14-41 | gi\|551594 | 194-221 | 100% |
| Seq ID NO: 55106 | 14-41 | gi\|551595 | 669-696 | 100% |
| Seq ID NO: 55106 | 14-41 | gi\|18032254 | 34-81 | 100% |
| Seq ID NO: 55106 | 18-41 | gi\|18477256 | 279-256 | 100% |
| Seq ID NO: 55106 | 18-41 | gi\|18477260 | 325-302 | 100% |
| Seq ID NO: 55106 | 18-41 | gi\|18477262 | 634-611 | 100% |
| Seq ID NO: 55106 | 14-35 | gi\|18477259 | 22-1 | 100% |
| Seq ID NO: 55106 | 14-35 | gi\|18477261 | 22-1 | 100% |
| Seq ID NO: 55106 | 14-35 | gi\|37780968 | 22-1 | 100% |
| Seq ID NO: 55108 | 1-93 | gi\|7143864 | 42-134 | 82% |
| Seq ID NO: 55117 | 35-57 | gi\|7144284 | 325-303 | 100% |
| Seq ID NO: 55119 | 36-155 | gi\|28916076 | 140-20 | 90% |
| Seq ID NO: 55175 | 1-160 | gi\|5107411 | 189-30 | 100% |
| Seq ID NO: 55175 | 1-160 | gi\|2149587 | 189-30 | 95% |
| Seq ID NO: 55175 | 47-160 | gi\|34105813 | 1719-1606 | 100% |
| Seq ID NO: 55175 | 1-160 | gi\|2149585 | 189-30 | 92% |
| Seq ID NO: 55175 | 1-160 | gi\|2738785 | 190-30 | 92% |
| Seq ID NO: 55175 | 1-160 | gi\|2738792 | 190-30 | 92% |
| Seq ID NO: 55175 | 1-160 | gi\|2738799 | 190-30 | 92% |
| Seq ID NO: 55175 | 1-160 | gi\|2738800 | 190-30 | 92% |
| Seq ID NO: 55175 | 2-160 | gi\|2707748 | 1766-1607 | 90% |
| Seq ID NO: 55175 | 1-80 | gi\|48479719 | 191-112 | 98% |
| Seq ID NO: 55175 | 1-80 | gi\|37674501 | 194-115 | 98% |
| Seq ID NO: 55175 | 115-160 | gi\|37674501 | 75-30 | 95% |
| Seq ID NO: 55175 | 1-78 | gi\|1147729 | 2525-2448 | 98% |
| Seq ID NO: 55175 | 115-160 | gi\|1147729 | 2413-2368 | 97% |
| Seq ID NO: 55175 | 1-78 | gi\|2232021 | 87-10 | 98% |
| Seq ID NO: 55226 | 1-24 | gi\|33139696 | 554-577 | 100% |
| Seq ID NO: 55245 | 1-25 | gi\|32324959 | 40-64 | 96% |
| Seq ID NO: 55392 | 173-276 | gi\|35504550 | 57-160 | 99% |
| Seq ID NO: 55392 | 326-425 | gi\|35504550 | 164-263 | 97% |
| Seq ID NO: 55392 | 1-66 | gi\|35504862 | 10-74 | 89% |
| Seq ID NO: 55425 | 57-187 | gi\|54545475 | 93-224 | 92% |
| Seq ID NO: 55425 | 231-321 | gi\|54545475 | 220-310 | 90% |
| Seq ID NO: 55468 | 1-141 | gi\|32325191 | 449-589 | 94% |
| Seq ID NO: 55545 | 75-99 | gi\|32325459 | 266-290 | 100% |
| Seq ID NO: 55553 | 1-116 | gi\|33139587 | 121-6 | 94% |
| Seq ID NO: 55566 | 167-228 | gi\|18083080 | 182-243 | 88% |
| Seq ID NO: 55640 | 887-1044 | gi\|33139586 | 1-158 | 96% |
| Seq ID NO: 55660 | 21-138 | gi\|28916076 | 1-119 | 91% |
| Seq ID NO: 55660 | 14-41 | gi\|159473 | 34-61 | 100% |
| Seq ID NO: 55660 | 14-41 | gi\|2454547 | 227-200 | 100% |
| Seq ID NO: 55660 | 14-41 | gi\|551594 | 194-221 | 100% |
| Seq ID NO: 55660 | 14-41 | gi\|551595 | 669-696 | 100% |
| Seq ID NO: 55660 | 14-41 | gi\|18032254 | 34-61 | 100% |
| Seq ID NO: 55660 | 18-41 | gi\|18477256 | 279-256 | 100% |
| Seq ID NO: 55660 | 18-41 | gi\|18477260 | 325-302 | 100% |
| Seq ID NO: 55660 | 18-41 | gi\|18477262 | 634-611 | 100% |
| Seq ID NO: 55660 | 14-35 | gi\|18477259 | 22-1 | 100% |
| Seq ID NO: 55660 | 14-35 | gi\|18477261 | 22-1 | 100% |
| Seq ID NO: 55660 | 14-35 | gi\|37780968 | 22-1 | 100% |
| Seq ID NO: 55719 | 1-146 | gi\|18080802 | 354-209 | 97% |
| Seq ID NO: 55719 | 1-131 | gi\|7144157 | 137-7 | 97% |
| Seq ID NO: 55719 | 1-130 | gi\|18088100 | 130-1 | 97% |
| Seq ID NO: 55719 | 1-124 | gi\|54549688 | 124-1 | 96% |
| Seq ID NO: 55719 | 1-118 | gi\|18089409 | 118-1 | 97% |
| Seq ID NO: 55719 | 1-117 | gi\|18090782 | 117-1 | 97% |
| Seq ID NO: 55719 | 25-146 | gi\|52128973 | 94-215 | 88% |
| Seq ID NO: 55719 | 1-78 | gi\|18083086 | 537-614 | 96% |

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 55719 | 1-75 | gi\|18090403 | 75-1 | 96% |
| Seq ID NO: 55719 | 25-121 | gi\|52129301 | 319-415 | 86% |
| Seq ID NO: 55719 | 100-146 | gi\|52129005 | 1-47 | 95% |
| Seq ID NO: 55719 | 83-146 | gi\|9033884 | 441-503 | 90% |
| Seq ID NO: 55719 | 83-146 | gi\|15768080 | 331-393 | 90% |
| Seq ID NO: 55719 | 71-146 | gi\|19383550 | 397-471 | 88% |
| Seq ID NO: 55719 | 83-146 | gi\|39747546 | 344-406 | 90% |
| Seq ID NO: 55719 | 100-146 | gi\|39747568 | 266-312 | 95% |
| Seq ID NO: 55719 | 100-146 | gi\|46984679 | 145-99 | 95% |
| Seq ID NO: 55719 | 105-146 | gi\|15769768 | 391-432 | 97% |
| Seq ID NO: 55719 | 105-146 | gi\|40669510 | 255-296 | 97% |
| Seq ID NO: 55719 | 100-140 | gi\|46986671 | 175-135 | 97% |
| Seq ID NO: 55719 | 108-146 | gi\|31326272 | 1-39 | 97% |
| Seq ID NO: 55719 | 105-146 | gi\|159682 | 379-420 | 92% |
| Seq ID NO: 55759 | 302-322 | gi\|46984484 | 89-109 | 100% |
| Seq ID NO: 55808 | 1-74 | gi\|54545841 | 238-311 | 91% |
| Seq ID NO: 55827 | 140-161 | gi\|46983788 | 125-146 | 100% |
| Seq ID NO: 55849 | 95-269 | gi\|54548527 | 231-405 | 87% |
| Seq ID NO: 55849 | 138-269 | gi\|54545989 | 2-133 | 88% |
| Seq ID NO: 55931 | 140-268 | gi\|33139063 | 130-258 | 96% |
| Seq ID NO: 55931 | 1-60 | gi\|33139063 | 71-130 | 98% |
| Seq ID NO: 56068 | 123-187 | gi\|21432594 | 122-186 | 86% |
| Seq ID NO: 56211 | 1-101 | gi\|7144157 | 39-139 | 97% |
| Seq ID NO: 56211 | 1-101 | gi\|54549688 | 26-126 | 96% |
| Seq ID NO: 56211 | 22-101 | gi\|18083086 | 614-535 | 96% |
| Seq ID NO: 56211 | 25-101 | gi\|18090403 | 1-77 | 96% |
| Seq ID NO: 56211 | 54-75 | gi\|52129301 | 340-319 | 100% |
| Seq ID NO: 56333 | 36-56 | gi\|33140432 | 264-284 | 100% |
| Seq ID NO: 56402 | 639-718 | gi\|33139730 | 156-76 | 93% |
| Seq ID NO: 56411 | 1-73 | gi\|16797830 | 749-821 | 100% |
| Seq ID NO: 56411 | 1-73 | gi\|16797832 | 747-819 | 100% |
| Seq ID NO: 56411 | 1-73 | gi\|26000759 | 745-817 | 100% |
| Seq ID NO: 56411 | 1-73 | gi\|31442320 | 746-818 | 100% |
| Seq ID NO: 56411 | 1-73 | gi\|31442322 | 746-818 | 98% |
| Seq ID NO: 56411 | 8-73 | gi\|21885259 | 776-841 | 98% |
| Seq ID NO: 45947 | 974-995 | gi\|46988291 | 426-405 | 100% |
| Seq ID NO: 56551 | 187-242 | gi\|18381363 | 1139-1194 | 91% |
| Seq ID NO: 56640 | 1-65 | gi\|33140765 | 16-80 | 98% |
| Seq ID NO: 56699 | 36-174 | gi\|28916076 | 140-1 | 92% |
| Seq ID NO: 56699 | 154-181 | gi\|159473 | 61-34 | 100% |
| Seq ID NO: 56699 | 154-181 | gi\|2454547 | 200-227 | 100% |
| Seq ID NO: 56699 | 154-181 | gi\|551594 | 221-194 | 100% |
| Seq ID NO: 56699 | 154-181 | gi\|551595 | 696-669 | 100% |
| Seq ID NO: 56699 | 154-181 | gi\|18032254 | 61-34 | 100% |
| Seq ID NO: 56699 | 154-177 | gi\|18477256 | 256-279 | 100% |
| Seq ID NO: 56699 | 154-177 | gi\|18477260 | 302-325 | 100% |
| Seq ID NO: 56699 | 154-177 | gi\|18477262 | 611-634 | 100% |
| Seq ID NO: 56699 | 160-181 | gi\|18477259 | 1-22 | 100% |
| Seq ID NO: 56699 | 160-181 | gi\|18477261 | 1-22 | 100% |
| Seq ID NO: 56699 | 160-181 | gi\|37780968 | 1-22 | 100% |
| Seq ID NO: 56752 | 348-369 | gi\|7235459 | 41-20 | 100% |
| Seq ID NO: 45973 | 404-544 | gi\|54546305 | 483-623 | 88% |
| Seq ID NO: 45973 | 181-293 | gi\|54546305 | 345-457 | 83% |
| Seq ID NO: 45973 | 434-544 | gi\|54544886 | 269-379 | 90% |
| Seq ID NO: 56872 | 764-956 | gi\|33140201 | 149-341 | 99% |
| Seq ID NO: 56872 | 569-719 | gi\|33140201 | 1-151 | 98% |
| Seq ID NO: 56889 | 189-333 | gi\|54544976 | 245-389 | 89% |
| Seq ID NO: 56927 | 75-226 | gi\|33139131 | 99-250 | 87% |
| Seq ID NO: 56927 | 81-221 | gi\|32324211 | 1-141 | 87% |
| Seq ID NO: 56972 | 1-101 | gi\|35504916 | 448-548 | 96% |
| Seq ID NO: 56972 | 1-85 | gi\|35504725 | 448-533 | 94% |
| Seq ID NO: 57065 | 168-188 | gi\|33952655 | 9-29 | 100% |
| Seq ID NO: 57065 | 168-188 | gi\|46422144 | 284-304 | 100% |
| Seq ID NO: 57084 | 62-214 | gi\|33140673 | 201-49 | 92% |
| Seq ID NO: 57084 | 71-214 | gi\|33139639 | 245-388 | 93% |
| Seq ID NO: 57086 | 190-217 | gi\|54547991 | 157-184 | 96% |
| Seq ID NO: 57220 | 1-66 | gi\|37517244 | 1816-1881 | 96% |
| Seq ID NO: 57351 | 5-196 | gi\|32323971 | 353-544 | 98% |
| Seq ID NO: 57416 | 412-434 | gi\|551595 | 853-875 | 100% |
| Seq ID NO: 57422 | 783-808 | gi\|46986223 | 315-290 | 100% |
| Seq ID NO: 57468 | 1-221 | gi\|2239108 | 36-256 | 100% |
| Seq ID NO: 57539 | 18-223 | gi\|32325381 | 184-389 | 92% |
| Seq ID NO: 57539 | 415-498 | gi\|32325381 | 398-481 | 97% |
| Seq ID NO: 57539 | 174-223 | gi\|33139814 | 8-57 | 100% |

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 57713 | 253-552 | gi\|33139068 | 28-327 | 97% |
| Seq ID NO: 57713 | 633-701 | gi\|33139068 | 334-402 | 98% |
| Seq ID NO: 57713 | 169-198 | gi\|33139068 | 1-30 | 100% |
| Seq ID NO: 57713 | 750-877 | gi\|33139557 | 441-568 | 93% |
| Seq ID NO: 57713 | 176-198 | gi\|33139557 | 1-23 | 100% |
| Seq ID NO: 57713 | 750-892 | gi\|33140099 | 424-566 | 92% |
| Seq ID NO: 57713 | 255-552 | gi\|33139079 | 16-313 | 97% |
| Seq ID NO: 57713 | 750-849 | gi\|33139079 | 434-533 | 94% |
| Seq ID NO: 57713 | 1-198 | gi\|32324666 | 26-223 | 96% |
| Seq ID NO: 57713 | 633-661 | gi\|32324666 | 527-555 | 100% |
| Seq ID NO: 57713 | 271-552 | gi\|33139103 | 1-282 | 97% |
| Seq ID NO: 57713 | 287-554 | gi\|33139308 | 38-306 | 97% |
| Seq ID NO: 57713 | 637-864 | gi\|33139308 | 315-545 | 90% |
| Seq ID NO: 57713 | 1232-1423 | gi\|33139521 | 162-353 | 96% |
| Seq ID NO: 57713 | 811-966 | gi\|33139521 | 1-159 | 89% |
| Seq ID NO: 57713 | 750-878 | gi\|33140185 | 112-240 | 93% |
| Seq ID NO: 57713 | 636-701 | gi\|33140185 | 1-66 | 98% |
| Seq ID NO: 57713 | 300-551 | gi\|32325329 | 51-302 | 90% |
| Seq ID NO: 57713 | 1229-1384 | gi\|32325562 | 408-563 | 99% |
| Seq ID NO: 57713 | 750-966 | gi\|32325562 | 189-408 | 89% |
| Seq ID NO: 57713 | 598-701 | gi\|32325562 | 40-143 | 96% |
| Seq ID NO: 57713 | 300-534 | gi\|32324015 | 367-601 | 90% |
| Seq ID NO: 57713 | 1229-1374 | gi\|33140373 | 408-553 | 100% |
| Seq ID NO: 57713 | 655-698 | gi\|32325327 | 481-524 | 90% |
| Seq ID NO: 57713 | 655-776 | gi\|32325443 | 481-599 | 83% |
| Seq ID NO: 57713 | 300-533 | gi\|33140304 | 225-458 | 89% |
| Seq ID NO: 57713 | 300-517 | gi\|33140764 | 367-584 | 89% |
| Seq ID NO: 57713 | 1229-1347 | gi\|32324619 | 408-526 | 100% |
| Seq ID NO: 57713 | 300-490 | gi\|32325078 | 367-557 | 90% |
| Seq ID NO: 57713 | 1254-1423 | gi\|33139825 | 258-427 | 90% |
| Seq ID NO: 57713 | 300-453 | gi\|33139892 | 410-563 | 90% |
| Seq ID NO: 57713 | 300-452 | gi\|33140637 | 410-562 | 90% |
| Seq ID NO: 57713 | 1288-1423 | gi\|32324536 | 247-382 | 91% |
| Seq ID NO: 57713 | 414-551 | gi\|32324536 | 10-147 | 89% |
| Seq ID NO: 57713 | 384-551 | gi\|33140589 | 1-168 | 88% |
| Seq ID NO: 57713 | 393-551 | gi\|33140074 | 4-162 | 88% |
| Seq ID NO: 57713 | 655-896 | gi\|32325371 | 173-411 | 83% |
| Seq ID NO: 57713 | 300-401 | gi\|32324162 | 476-577 | 92% |
| Seq ID NO: 57713 | 428-551 | gi\|32324623 | 225-348 | 88% |
| Seq ID NO: 57713 | 300-375 | gi\|32324623 | 103-178 | 93% |
| Seq ID NO: 57713 | 300-353 | gi\|33139035 | 491-544 | 94% |
| Seq ID NO: 57793 | 1-189 | gi\|33139897 | 347-535 | 91% |
| Seq ID NO: 57824 | 6-146 | gi\|32324211 | 1-141 | 88% |
| Seq ID NO: 57824 | 17-151 | gi\|33139131 | 116-250 | 88% |
| Seq ID NO: 57824 | 1-145 | gi\|33140673 | 193-49 | 83% |
| Seq ID NO: 57824 | 13-145 | gi\|33139639 | 256-388 | 82% |
| Seq ID NO: 57824 | 152-172 | gi\|45563795 | 521-501 | 100% |
| Seq ID NO: 57907 | 1213-1367 | gi\|18081696 | 127-281 | 85% |
| Seq ID NO: 57996 | 664-684 | gi\|39747573 | 93-113 | 100% |
| Seq ID NO: 58001 | 4-65 | gi\|27541441 | 265-326 | 84% |
| Seq ID NO: 46037 | 415-488 | gi\|21393234 | 329-402 | 91% |
| Seq ID NO: 46037 | 117-143 | gi\|21393234 | 148-174 | 100% |
| Seq ID NO: 46037 | 377-488 | gi\|18080246 | 261-372 | 85% |
| Seq ID NO: 46037 | 418-488 | gi\|18381808 | 299-229 | 90% |
| Seq ID NO: 46037 | 427-488 | gi\|52128281 | 271-332 | 91% |
| Seq ID NO: 58171 | 85-106 | gi\|22139607 | 133-112 | 100% |
| Seq ID NO: 58223 | 117-138 | gi\|16746280 | 49-70 | 100% |
| Seq ID NO: 58237 | 123-269 | gi\|33139639 | 245-388 | 89% |
| Seq ID NO: 58237 | 114-269 | gi\|33140673 | 201-49 | 87% |
| Seq ID NO: 58237 | 121-246 | gi\|33139131 | 99-224 | 82% |
| Seq ID NO: 58237 | 333-378 | gi\|32324211 | 211-256 | 91% |
| Seq ID NO: 58264 | 869-1010 | gi\|18082514 | 100-241 | 90% |
| Seq ID NO: 58264 | 1203-1298 | gi\|18082514 | 245-340 | 92% |
| Seq ID NO: 58357 | 136-238 | gi\|54549492 | 497-599 | 88% |
| Seq ID NO: 58357 | 369-416 | gi\|54549492 | 633-680 | 91% |
| Seq ID NO: 58382 | 12-159 | gi\|18383012 | 1144-1291 | 84% |
| Seq ID NO: 58427 | 1-143 | gi\|16797830 | 62-204 | 97% |
| Seq ID NO: 58427 | 1-143 | gi\|16797831 | 62-202 | 97% |
| Seq ID NO: 58427 | 1-143 | gi\|16797832 | 63-203 | 97% |
| Seq ID NO: 58427 | 1-143 | gi\|47118285 | 74-214 | 96% |
| Seq ID NO: 58427 | 1-142 | gi\|26000762 | 62-201 | 95% |
| Seq ID NO: 58427 | 1-143 | gi\|31442322 | 62-202 | 95% |
| Seq ID NO: 58427 | 1-143 | gi\|38096133 | 62-202 | 93% |
| Seq ID NO: 58438 | 319-443 | gi\|32324393 | 180-307 | 96% |
| Seq ID NO: 58438 | 1-83 | gi\|32324393 | 25-108 | 98% |
| Seq ID NO: 58438 | 154-195 | gi\|32324393 | 107-148 | 100% |
| Seq ID NO: 58438 | 239-273 | gi\|32324393 | 147-181 | 100% |
| Seq ID NO: 58438 | 319-383 | gi\|33140257 | 413-477 | 98% |
| Seq ID NO: 58438 | 154-191 | gi\|33140257 | 345-382 | 100% |
| Seq ID NO: 58478 | 192-238 | gi\|18089268 | 22-68 | 89% |
| Seq ID NO: 58670 | 81-148 | gi\|18090251 | 452-519 | 88% |
| Seq ID NO: 58722 | 346-432 | gi\|19266104 | 21-107 | 84% |
| Seq ID NO: 46083 | 1-119 | gi\|33139765 | 458-576 | 99% |
| Seq ID NO: 46083 | 265-305 | gi\|52128426 | 396-436 | 95% |
| Seq ID NO: 46084 | 295-415 | gi\|33139765 | 576-456 | 99% |
| Seq ID NO: 46084 | 479-528 | gi\|33139765 | 454-405 | 100% |
| Seq ID NO: 46084 | 109-149 | gi\|52128426 | 436-396 | 95% |
| Seq ID NO: 58765 | 150-170 | gi\|18081306 | 417-437 | 100% |
| Seq ID NO: 58768 | 2-66 | gi\|7143917 | 219-283 | 90% |
| Seq ID NO: 58912 | 483-676 | gi\|7144233 | 308-501 | 87% |
| Seq ID NO: 58912 | 483-667 | gi\|7144339 | 311-495 | 86% |
| Seq ID NO: 58913 | 201-271 | gi\|52128794 | 102-172 | 90% |
| Seq ID NO: 58913 | 187-272 | gi\|46985091 | 319-234 | 85% |
| Seq ID NO: 58913 | 85-121 | gi\|18080422 | 365-401 | 94% |
| Seq ID NO: 58913 | 249-272 | gi\|46985022 | 259-236 | 100% |
| Seq ID NO: 59048 | 23-135 | gi\|33139660 | 491-603 | 98% |
| Seq ID NO: 59083 | 221-245 | gi\|46987193 | 49-25 | 96% |
| Seq ID NO: 59131 | 1-107 | gi\|18082168 | 3-109 | 94% |
| Seq ID NO: 59131 | 16-108 | gi\|51334509 | 37-129 | 88% |
| Seq ID NO: 59131 | 70-108 | gi\|52129549 | 138-176 | 89% |
| Seq ID NO: 59132 | 1-56 | gi\|7641359 | 475-420 | 91% |
| Seq ID NO: 59132 | 1-59 | gi\|14085900 | 55-113 | 90% |
| Seq ID NO: 59132 | 1-47 | gi\|14086110 | 51-97 | 93% |
| Seq ID NO: 59132 | 1-56 | gi\|15767660 | 65-120 | 89% |
| Seq ID NO: 59132 | 1-56 | gi\|18495580 | 501-446 | 89% |
| Seq ID NO: 59132 | 19-59 | gi\|39747527 | 61-101 | 92% |
| Seq ID NO: 59201 | 21-138 | gi\|28916076 | 1-119 | 91% |
| Seq ID NO: 59201 | 14-41 | gi\|159473 | 34-61 | 100% |
| Seq ID NO: 59201 | 14-41 | gi\|2454547 | 227-200 | 100% |
| Seq ID NO: 59201 | 14-41 | gi\|551594 | 194-221 | 100% |
| Seq ID NO: 59201 | 14-41 | gi\|551595 | 669-696 | 100% |
| Seq ID NO: 59201 | 14-41 | gi\|18032254 | 34-61 | 100% |
| Seq ID NO: 59201 | 18-41 | gi\|18477256 | 279-256 | 100% |
| Seq ID NO: 59201 | 18-41 | gi\|18477260 | 325-302 | 100% |
| Seq ID NO: 59201 | 18-41 | gi\|18477262 | 634-611 | 100% |
| Seq ID NO: 59201 | 14-35 | gi\|18477259 | 22-1 | 100% |
| Seq ID NO: 59201 | 14-35 | gi\|18477261 | 22-1 | 100% |
| Seq ID NO: 59201 | 14-35 | gi\|37780968 | 22-1 | 100% |
| Seq ID NO: 59268 | 131-256 | gi\|33139189 | 152-277 | 99% |
| Seq ID NO: 59268 | 1-56 | gi\|33139189 | 96-151 | 98% |
| Seq ID NO: 59269 | 3-85 | gi\|7143543 | 482-564 | 88% |
| Seq ID NO: 59311 | 1-81 | gi\|7144052 | 441-521 | 90% |
| Seq ID NO: 59484 | 1-118 | gi\|18080802 | 329-209 | 95% |
| Seq ID NO: 59484 | 1-103 | gi\|7144157 | 112-7 | 95% |
| Seq ID NO: 59484 | 1-102 | gi\|18088100 | 105-1 | 95% |
| Seq ID NO: 59484 | 1-96 | gi\|54549688 | 99-1 | 93% |
| Seq ID NO: 59484 | 1-90 | gi\|18089409 | 93-1 | 94% |
| Seq ID NO: 59484 | 1-89 | gi\|18090782 | 92-1 | 94% |
| Seq ID NO: 59484 | 56-118 | gi\|9033884 | 441-503 | 90% |
| Seq ID NO: 59484 | 56-118 | gi\|15768080 | 331-393 | 90% |
| Seq ID NO: 59484 | 56-118 | gi\|39747546 | 344-406 | 90% |
| Seq ID NO: 59484 | 77-118 | gi\|15769768 | 391-432 | 97% |
| Seq ID NO: 59484 | 77-118 | gi\|19383550 | 430-471 | 97% |
| Seq ID NO: 59484 | 77-118 | gi\|39747568 | 271-312 | 97% |
| Seq ID NO: 59484 | 77-112 | gi\|46986671 | 170-135 | 100% |
| Seq ID NO: 59484 | 80-118 | gi\|31326272 | 1-39 | 97% |
| Seq ID NO: 59484 | 77-118 | gi\|159682 | 379-420 | 92% |
| Seq ID NO: 59484 | 77-118 | gi\|15784370 | 177-218 | 92% |
| Seq ID NO: 59530 | 1-129 | gi\|33139697 | 192-63 | 97% |
| Seq ID NO: 59558 | 15-54 | gi\|28916076 | 1-40 | 97% |
| Seq ID NO: 59558 | 8-35 | gi\|159473 | 34-61 | 100% |
| Seq ID NO: 59558 | 8-35 | gi\|2454547 | 227-200 | 100% |
| Seq ID NO: 59558 | 8-35 | gi\|551594 | 194-221 | 100% |
| Seq ID NO: 59558 | 8-35 | gi\|551595 | 669-696 | 100% |
| Seq ID NO: 59558 | 8-35 | gi\|18032254 | 34-61 | 100% |
| Seq ID NO: 59558 | 12-35 | gi\|18477256 | 279-256 | 100% |
| Seq ID NO: 59558 | 12-35 | gi\|18477260 | 325-302 | 100% |
| Seq ID NO: 59558 | 12-35 | gi\|18477262 | 634-611 | 100% |

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 59558 | 8-29 | gi\|18477259 | 22-1 | 100% |
| Seq ID NO: 59558 | 8-29 | gi\|18477261 | 22-1 | 100% |
| Seq ID NO: 59558 | 8-29 | gi\|37780968 | 22-1 | 100% |
| Seq ID NO: 59597 | 141-230 | gi\|33139639 | 297-386 | 85% |
| Seq ID NO: 59597 | 141-193 | gi\|33140673 | 140-88 | 90% |
| Seq ID NO: 59652 | 7-89 | gi\|33140014 | 182-264 | 100% |
| Seq ID NO: 59901 | 94-114 | gi\|7798143 | 245-225 | 100% |
| Seq ID NO: 59911 | 1-141 | gi\|2239106 | 1166-1307 | 98% |
| Seq ID NO: 59911 | 1-141 | gi\|37517243 | 1166-1307 | 98% |
| Seq ID NO: 59944 | 178-340 | gi\|33139639 | 257-419 | 89% |
| Seq ID NO: 59944 | 159-310 | gi\|33140673 | 199-48 | 87% |
| Seq ID NO: 60099 | 81-221 | gi\|32324211 | 1-141 | 90% |
| Seq ID NO: 60099 | 92-226 | gi\|33139131 | 116-250 | 89% |
| Seq ID NO: 60099 | 305-349 | gi\|33139131 | 293-337 | 93% |
| Seq ID NO: 60099 | 70-220 | gi\|33140673 | 199-49 | 86% |
| Seq ID NO: 60099 | 89-264 | gi\|33139639 | 257-429 | 84% |
| Seq ID NO: 60155 | 1-67 | gi\|7144157 | 200-134 | 91% |
| Seq ID NO: 60155 | 1-67 | gi\|54549688 | 187-121 | 91% |
| Seq ID NO: 60206 | 46-72 | gi\|159473 | 61-35 | 100% |
| Seq ID NO: 60206 | 46-72 | gi\|2454547 | 200-226 | 100% |
| Seq ID NO: 60206 | 46-72 | gi\|551594 | 221-195 | 100% |
| Seq ID NO: 60206 | 46-72 | gi\|551595 | 696-670 | 100% |
| Seq ID NO: 60206 | 46-72 | gi\|18032254 | 61-35 | 100% |
| Seq ID NO: 60206 | 46-69 | gi\|18477256 | 256-279 | 100% |
| Seq ID NO: 60206 | 46-69 | gi\|18477260 | 302-325 | 100% |
| Seq ID NO: 60206 | 46-69 | gi\|18477262 | 611-634 | 100% |
| Seq ID NO: 60206 | 52-72 | gi\|18477259 | 1-21 | 100% |
| Seq ID NO: 60206 | 52-72 | gi\|18477261 | 1-21 | 100% |
| Seq ID NO: 60206 | 52-72 | gi\|37780968 | 1-21 | 100% |
| Seq ID NO: 60211 | 305-361 | gi\|18081798 | 206-262 | 91% |
| Seq ID NO: 60211 | 305-361 | gi\|54547765 | 204-260 | 89% |
| Seq ID NO: 60211 | 52-77 | gi\|9829211 | 55-80 | 100% |
| Seq ID NO: 60211 | 52-77 | gi\|21652727 | 26-51 | 100% |
| Seq ID NO: 60220 | 1-95 | gi\|33140348 | 161-255 | 96% |
| Seq ID NO: 60378 | 15-74 | gi\|28916076 | 1-60 | 93% |
| Seq ID NO: 60378 | 8-35 | gi\|159473 | 34-61 | 100% |
| Seq ID NO: 60378 | 8-35 | gi\|2454547 | 227-200 | 100% |
| Seq ID NO: 60378 | 8-35 | gi\|551594 | 194-221 | 100% |
| Seq ID NO: 60378 | 8-35 | gi\|551595 | 669-696 | 100% |
| Seq ID NO: 60378 | 8-35 | gi\|18032254 | 34-61 | 100% |
| Seq ID NO: 60378 | 12-35 | gi\|18477256 | 279-256 | 100% |
| Seq ID NO: 60378 | 12-35 | gi\|18477260 | 325-302 | 100% |
| Seq ID NO: 60378 | 12-35 | gi\|18477262 | 634-611 | 100% |
| Seq ID NO: 60378 | 8-29 | gi\|18477259 | 22-1 | 100% |
| Seq ID NO: 60378 | 8-29 | gi\|18477261 | 22-1 | 100% |
| Seq ID NO: 60378 | 8-29 | gi\|37780968 | 22-1 | 100% |
| Seq ID NO: 60409 | 273-620 | gi\|32324347 | 2-350 | 96% |
| Seq ID NO: 60409 | 680-806 | gi\|32324347 | 351-477 | 98% |
| Seq ID NO: 60409 | 680-784 | gi\|33139657 | 351-455 | 98% |
| Seq ID NO: 60409 | 289-615 | gi\|33140241 | 13-338 | 97% |
| Seq ID NO: 60409 | 677-806 | gi\|33140241 | 341-470 | 98% |
| Seq ID NO: 60409 | 272-619 | gi\|33139259 | 1-348 | 95% |
| Seq ID NO: 60409 | 278-620 | gi\|33139000 | 12-355 | 96% |
| Seq ID NO: 60409 | 272-615 | gi\|33139478 | 1-339 | 96% |
| Seq ID NO: 60409 | 268-620 | gi\|32324919 | 1-354 | 95% |
| Seq ID NO: 60409 | 273-609 | gi\|33139390 | 2-339 | 95% |
| Seq ID NO: 60409 | 391-620 | gi\|33140350 | 66-296 | 96% |
| Seq ID NO: 60409 | 273-337 | gi\|33140350 | 2-66 | 93% |
| Seq ID NO: 60409 | 498-615 | gi\|33139683 | 1-118 | 98% |
| Seq ID NO: 60495 | 1-88 | gi\|5107411 | 569-656 | 100% |
| Seq ID NO: 60495 | 1-88 | gi\|16797830 | 379-466 | 100% |
| Seq ID NO: 60495 | 1-88 | gi\|16797831 | 377-464 | 98% |
| Seq ID NO: 60495 | 1-88 | gi\|16797832 | 378-465 | 98% |
| Seq ID NO: 60495 | 1-88 | gi\|31442322 | 377-464 | 98% |
| Seq ID NO: 60495 | 5-88 | gi\|26000760 | 381-464 | 98% |
| Seq ID NO: 60495 | 1-88 | gi\|38096135 | 377-465 | 95% |
| Seq ID NO: 60495 | 12-86 | gi\|31442314 | 392-467 | 93% |
| Seq ID NO: 60495 | 4-86 | gi\|38096138 | 386-468 | 90% |
| Seq ID NO: 60495 | 3-86 | gi\|16797838 | 399-482 | 89% |
| Seq ID NO: 60532 | 243-263 | gi\|46986928 | 44-64 | 100% |
| Seq ID NO: 60533 | 237-257 | gi\|46986928 | 64-44 | 100% |
| Seq ID NO: 60534 | 122-248 | gi\|33139568 | 363-489 | 99% |
| Seq ID NO: 60534 | 1-75 | gi\|33139568 | 293-367 | 98% |
| Seq ID NO: 60596 | 1-99 | gi\|33139131 | 122-220 | 89% |

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 60596 | 29-92 | gi\|33140673 | 143-80 | 87% |
| Seq ID NO: 60782 | 367-405 | gi\|54547981 | 61-24 | 94% |
| Seq ID NO: 60782 | 792-812 | gi\|19435901 | 24-4 | 100% |
| Seq ID NO: 60783 | 218-256 | gi\|54547981 | 24-61 | 94% |
| Seq ID NO: 60788 | 36-165 | gi\|28916076 | 140-10 | 92% |
| Seq ID NO: 60644 | 26-217 | gi\|18080216 | 20-211 | 86% |
| Seq ID NO: 60947 | 1-85 | gi\|33140348 | 171-255 | 97% |
| Seq ID NO: 61051 | 73-95 | gi\|39746742 | 647-625 | 100% |
| Seq ID NO: 61179 | 139-160 | gi\|34316675 | 229-208 | 100% |
| Seq ID NO: 61217 | 76-324 | gi\|33139639 | 245-493 | 87% |
| Seq ID NO: 61217 | 71-219 | gi\|33140673 | 197-49 | 89% |
| Seq ID NO: 61217 | 115-219 | gi\|32324211 | 36-140 | 88% |
| Seq ID NO: 61303 | 36-174 | gi\|28916076 | 140-1 | 92% |
| Seq ID NO: 61303 | 154-181 | gi\|159473 | 61-34 | 100% |
| Seq ID NO: 61303 | 154-181 | gi\|2454547 | 200-227 | 100% |
| Seq ID NO: 61303 | 154-181 | gi\|551594 | 221-194 | 100% |
| Seq ID NO: 61303 | 154-181 | gi\|551595 | 696-669 | 100% |
| Seq ID NO: 61303 | 154-181 | gi\|18032254 | 61-34 | 100% |
| Seq ID NO: 61303 | 154-177 | gi\|18477256 | 256-279 | 100% |
| Seq ID NO: 61303 | 154-177 | gi\|18477260 | 302-325 | 100% |
| Seq ID NO: 61303 | 154-177 | gi\|18477262 | 611-634 | 100% |
| Seq ID NO: 61303 | 160-181 | gi\|18477259 | 1-22 | 100% |
| Seq ID NO: 61303 | 160-181 | gi\|18477261 | 1-22 | 100% |
| Seq ID NO: 61303 | 160-181 | gi\|37780968 | 1-22 | 100% |
| Seq ID NO: 61351 | 4-140 | gi\|18080057 | 229-93 | 85% |
| Seq ID NO: 61351 | 4-140 | gi\|54547707 | 233-97 | 84% |
| Seq ID NO: 61352 | 186-312 | gi\|18080057 | 303-429 | 90% |
| Seq ID NO: 61352 | 1-134 | gi\|18080057 | 159-292 | 88% |
| Seq ID NO: 61352 | 1-139 | gi\|54547707 | 163-300 | 88% |
| Seq ID NO: 61352 | 186-312 | gi\|54547707 | 307-433 | 89% |
| Seq ID NO: 61352 | 363-405 | gi\|54547707 | 443-485 | 90% |
| Seq ID NO: 61526 | 29-138 | gi\|28916076 | 9-119 | 91% |
| Seq ID NO: 61553 | 31-90 | gi\|51237572 | 280-339 | 86% |
| Seq ID NO: 46246 | 1-165 | gi\|33139608 | 404-567 | 98% |
| Seq ID NO: 46246 | 1-62 | gi\|32323997 | 404-464 | 98% |
| Seq ID NO: 61561 | 480-500 | gi\|54546754 | 60-40 | 100% |
| Seq ID NO: 61600 | 3-49 | gi\|32324211 | 94-140 | 93% |
| Seq ID NO: 61643 | 680-700 | gi\|23260226 | 280-260 | 100% |
| Seq ID NO: 61686 | 1-73 | gi\|16797830 | 749-821 | 100% |
| Seq ID NO: 61686 | 1-73 | gi\|16797832 | 747-819 | 100% |
| Seq ID NO: 61686 | 1-73 | gi\|26000759 | 745-817 | 100% |
| Seq ID NO: 61686 | 1-73 | gi\|31442320 | 746-818 | 100% |
| Seq ID NO: 61686 | 1-73 | gi\|31442322 | 746-818 | 98% |
| Seq ID NO: 61686 | 8-73 | gi\|21885259 | 776-841 | 98% |
| Seq ID NO: 61688 | 97-117 | gi\|52128725 | 61-81 | 100% |
| Seq ID NO: 61719 | 701-721 | gi\|32185118 | 164-144 | 100% |
| Seq ID NO: 61810 | 13-290 | gi\|33140136 | 39-317 | 85% |
| Seq ID NO: 61937 | 5-25 | gi\|19267937 | 180-160 | 100% |
| Seq ID NO: 61955 | 1-89 | gi\|33139270 | 471-383 | 100% |
| Seq ID NO: 61980 | 1-78 | gi\|33140673 | 126-49 | 92% |
| Seq ID NO: 61980 | 19-84 | gi\|33139131 | 185-250 | 92% |
| Seq ID NO: 61980 | 250-309 | gi\|33139639 | 521-580 | 91% |
| Seq ID NO: 46268 | 777-960 | gi\|33140770 | 55-237 | 99% |
| Seq ID NO: 46268 | 639-695 | gi\|33140770 | 1-57 | 98% |
| Seq ID NO: 62170 | 207-227 | gi\|46422740 | 369-349 | 100% |
| Seq ID NO: 62176 | 200-225 | gi\|30028086 | 358-383 | 100% |
| Seq ID NO: 62176 | 198-218 | gi\|16005270 | 477-497 | 100% |
| Seq ID NO: 46279 | 5-190 | gi\|35504456 | 365-180 | 96% |
| Seq ID NO: 46279 | 63-188 | gi\|7143616 | 133-258 | 91% |
| Seq ID NO: 46279 | 63-188 | gi\|18381740 | 382-507 | 91% |
| Seq ID NO: 46279 | 63-184 | gi\|18381740 | 131-252 | 91% |
| Seq ID NO: 46279 | 76-188 | gi\|18381923 | 603-491 | 92% |
| Seq ID NO: 46279 | 73-188 | gi\|21493480 | 425-310 | 85% |
| Seq ID NO: 62414 | 1-128 | gi\|32323987 | 182-309 | 100% |
| Seq ID NO: 62414 | 173-246 | gi\|32323987 | 309-382 | 100% |
| Seq ID NO: 62414 | 173-222 | gi\|33140527 | 311-360 | 98% |
| Seq ID NO: 62539 | 200-225 | gi\|54547695 | 79-104 | 96% |
| Seq ID NO: 62576 | 170-298 | gi\|33139556 | 85-213 | 94% |
| Seq ID NO: 62576 | 42-126 | gi\|33139556 | 1-85 | 98% |
| Seq ID NO: 46293 | 154-303 | gi\|18080373 | 337-486 | 91% |
| Seq ID NO: 62611 | 1-45 | gi\|33139645 | 197-241 | 97% |
| Seq ID NO: 62636 | 254-285 | gi\|18382597 | 630-661 | 96% |
| Seq ID NO: 46302 | 262-359 | gi\|18381117 | 806-709 | 92% |
| Seq ID NO: 46302 | 262-362 | gi\|7144103 | 148-248 | 91% |

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 46305 | 314-411 | gi|54548221 | 329-232 | 88% |
| Seq ID NO: 62776 | 3-93 | gi|33140348 | 248-158 | 89% |
| Seq ID NO: 62899 | 1-140 | gi|32325217 | 127-267 | 96% |
| Seq ID NO: 62904 | 154-306 | gi|18082113 | 218-370 | 89% |
| Seq ID NO: 62904 | 158-306 | gi|54549200 | 528-380 | 87% |
| Seq ID NO: 62904 | 159-306 | gi|54545591 | 457-310 | 87% |
| Seq ID NO: 62904 | 179-306 | gi|7144024 | 503-377 | 87% |
| Seq ID NO: 62986 | 504-558 | gi|32324842 | 158-212 | 92% |
| Seq ID NO: 63015 | 1-98 | gi|32324253 | 114-17 | 94% |
| Seq ID NO: 63100 | 554-708 | gi|32324459 | 81-235 | 95% |
| Seq ID NO: 63107 | 36-174 | gi|28916076 | 140-1 | 92% |
| Seq ID NO: 63107 | 154-181 | gi|159473 | 61-34 | 100% |
| Seq ID NO: 63107 | 154-181 | gi|2454547 | 200-227 | 100% |
| Seq ID NO: 63107 | 154-181 | gi|551594 | 221-194 | 100% |
| Seq ID NO: 63107 | 154-181 | gi|551595 | 696-669 | 100% |
| Seq ID NO: 63107 | 154-181 | gi|18032254 | 61-34 | 100% |
| Seq ID NO: 63107 | 154-177 | gi|18477256 | 256-279 | 100% |
| Seq ID NO: 63107 | 154-177 | gi|18477260 | 302-325 | 100% |
| Seq ID NO: 63107 | 154-177 | gi|18477262 | 611-634 | 100% |
| Seq ID NO: 63107 | 160-181 | gi|18477259 | 1-22 | 100% |
| Seq ID NO: 63107 | 160-181 | gi|18477261 | 1-22 | 100% |
| Seq ID NO: 63107 | 160-181 | gi|37780968 | 1-22 | 100% |
| Seq ID NO: 63189 | 13-47 | gi|7143962 | 302-269 | 94% |
| Seq ID NO: 63384 | 576-772 | gi|32325427 | 297-493 | 97% |
| Seq ID NO: 63384 | 217-381 | gi|32325427 | 50-214 | 98% |
| Seq ID NO: 63384 | 428-514 | gi|32325427 | 213-299 | 100% |
| Seq ID NO: 63384 | 110-159 | gi|32325427 | 1-50 | 94% |
| Seq ID NO: 63384 | 629-772 | gi|18089917 | 1-144 | 88% |
| Seq ID NO: 63450 | 15-54 | gi|28916076 | 1-40 | 97% |
| Seq ID NO: 63450 | 8-35 | gi|159473 | 34-61 | 100% |
| Seq ID NO: 63450 | 8-35 | gi|2454547 | 227-200 | 100% |
| Seq ID NO: 63450 | 8-35 | gi|551594 | 194-221 | 100% |
| Seq ID NO: 63450 | 8-35 | gi|551595 | 669-696 | 100% |
| Seq ID NO: 63450 | 8-35 | gi|18032254 | 34-61 | 100% |
| Seq ID NO: 63450 | 12-35 | gi|18477256 | 279-256 | 100% |
| Seq ID NO: 63450 | 12-35 | gi|18477260 | 325-302 | 100% |
| Seq ID NO: 63450 | 12-35 | gi|18477262 | 634-611 | 100% |
| Seq ID NO: 63450 | 8-29 | gi|18477259 | 22-1 | 100% |
| Seq ID NO: 63450 | 8-29 | gi|18477261 | 22-1 | 100% |
| Seq ID NO: 63450 | 8-29 | gi|37780968 | 22-1 | 100% |
| Seq ID NO: 63508 | 16-41 | gi|30166029 | 39-64 | 96% |
| Seq ID NO: 63529 | 4-111 | gi|33140348 | 148-255 | 93% |
| Seq ID NO: 46344 | 3-176 | gi|54548367 | 26-199 | 85% |
| Seq ID NO: 46344 | 461-533 | gi|54548367 | 299-371 | 90% |
| Seq ID NO: 63626 | 1-138 | gi|18090776 | 20-157 | 88% |
| Seq ID NO: 46358 | 286-423 | gi|7144085 | 453-591 | 91% |
| Seq ID NO: 63905 | 1-73 | gi|16797830 | 749-821 | 100% |
| Seq ID NO: 63905 | 1-73 | gi|16797832 | 747-819 | 100% |
| Seq ID NO: 63905 | 1-73 | gi|26000759 | 745-817 | 100% |
| Seq ID NO: 63905 | 1-73 | gi|31442320 | 746-818 | 100% |
| Seq ID NO: 63905 | 1-73 | gi|31442322 | 746-818 | 98% |
| Seq ID NO: 63905 | 8-73 | gi|21885259 | 776-841 | 98% |
| Seq ID NO: 63930 | 36-103 | gi|18080500 | 393-460 | 86% |
| Seq ID NO: 64030 | 21-138 | gi|28916076 | 1-119 | 91% |
| Seq ID NO: 64030 | 14-41 | gi|159473 | 34-61 | 100% |
| Seq ID NO: 64030 | 14-41 | gi|2454547 | 227-200 | 100% |
| Seq ID NO: 64030 | 14-41 | gi|551594 | 194-221 | 100% |
| Seq ID NO: 64030 | 14-41 | gi|551595 | 669-696 | 100% |
| Seq ID NO: 64030 | 14-41 | gi|18032254 | 34-61 | 100% |
| Seq ID NO: 64030 | 18-41 | gi|18477256 | 279-256 | 100% |
| Seq ID NO: 64030 | 18-41 | gi|18477260 | 325-302 | 100% |
| Seq ID NO: 64030 | 18-41 | gi|18477262 | 634-611 | 100% |
| Seq ID NO: 64030 | 14-35 | gi|18477259 | 22-1 | 100% |
| Seq ID NO: 64030 | 14-35 | gi|18477261 | 22-1 | 100% |
| Seq ID NO: 64030 | 14-35 | gi|37780968 | 22-1 | 100% |
| Seq ID NO: 64057 | 318-354 | gi|33139730 | 82-119 | 97% |
| Seq ID NO: 64082 | 276-364 | gi|32325034 | 20-108 | 96% |
| Seq ID NO: 64082 | 74-140 | gi|32324889 | 134-68 | 100% |
| Seq ID NO: 64082 | 325-364 | gi|33139589 | 1-40 | 97% |
| Seq ID NO: 64082 | 74-147 | gi|21393259 | 27-100 | 85% |
| Seq ID NO: 64082 | 74-147 | gi|20498904 | 25-98 | 85% |
| Seq ID NO: 64106 | 2-35 | gi|20064584 | 1-34 | 97% |
| Seq ID NO: 64146 | 339-442 | gi|33140237 | 332-229 | 100% |
| Seq ID NO: 64146 | 21-109 | gi|33140237 | 419-331 | 97% |
| Seq ID NO: 64146 | 452-518 | gi|33140237 | 219-153 | 98% |
| Seq ID NO: 64146 | 580-617 | gi|33140237 | 151-114 | 100% |
| Seq ID NO: 64148 | 457-691 | gi|32325211 | 200-434 | 98% |
| Seq ID NO: 64148 | 302-406 | gi|32325211 | 96-200 | 96% |
| Seq ID NO: 64148 | 145-221 | gi|32325211 | 24-99 | 96% |
| Seq ID NO: 64148 | 735-788 | gi|32325211 | 434-487 | 100% |
| Seq ID NO: 64148 | 897-948 | gi|32325211 | 540-591 | 100% |
| Seq ID NO: 64148 | 798-842 | gi|32325211 | 497-541 | 100% |
| Seq ID NO: 64148 | 75-101 | gi|32325211 | 1-27 | 100% |
| Seq ID NO: 64148 | 897-1003 | gi|32324168 | 477-583 | 99% |
| Seq ID NO: 64148 | 186-221 | gi|32324168 | 1-36 | 97% |
| Seq ID NO: 64148 | 457-684 | gi|33139272 | 319-546 | 98% |
| Seq ID NO: 64148 | 1-101 | gi|33139272 | 46-146 | 99% |
| Seq ID NO: 64148 | 897-996 | gi|33139975 | 485-584 | 99% |
| Seq ID NO: 64148 | 178-221 | gi|33139735 | 1-44 | 97% |
| Seq ID NO: 64181 | 21-138 | gi|28916076 | 1-119 | 91% |
| Seq ID NO: 64181 | 14-41 | gi|159473 | 34-61 | 100% |
| Seq ID NO: 64181 | 14-41 | gi|2454547 | 227-200 | 100% |
| Seq ID NO: 64181 | 14-41 | gi|551594 | 194-221 | 100% |
| Seq ID NO: 64181 | 14-41 | gi|551595 | 669-696 | 100% |
| Seq ID NO: 64181 | 14-41 | gi|18032254 | 34-61 | 100% |
| Seq ID NO: 64181 | 18-41 | gi|18477256 | 279-256 | 100% |
| Seq ID NO: 64181 | 18-41 | gi|18477260 | 325-302 | 100% |
| Seq ID NO: 64181 | 18-41 | gi|18477262 | 634-611 | 100% |
| Seq ID NO: 64181 | 14-35 | gi|18477259 | 22-1 | 100% |
| Seq ID NO: 64181 | 14-35 | gi|18477261 | 22-1 | 100% |
| Seq ID NO: 64181 | 14-35 | gi|37780968 | 22-1 | 100% |
| Seq ID NO: 64254 | 169-189 | gi|18083118 | 116-136 | 100% |
| Seq ID NO: 64254 | 169-189 | gi|18382418 | 749-769 | 100% |
| Seq ID NO: 64268 | 399-518 | gi|54546846 | 257-382 | 82% |
| Seq ID NO: 64305 | 240-260 | gi|24467850 | 41-21 | 100% |
| Seq ID NO: 64309 | 148-249 | gi|18088268 | 401-300 | 90% |
| Seq ID NO: 46394 | 286-347 | gi|46987704 | 361-300 | 85% |
| Seq ID NO: 64348 | 295-324 | gi|7922575 | 190-218 | 96% |
| Seq ID NO: 64377 | 645-702 | gi|54544818 | 520-577 | 91% |
| Seq ID NO: 64390 | 83-126 | gi|551594 | 1028-1070 | 93% |
| Seq ID NO: 64390 | 83-126 | gi|551595 | 267-309 | 93% |
| Seq ID NO: 64477 | 21-138 | gi|28916076 | 1-119 | 91% |
| Seq ID NO: 64477 | 14-41 | gi|159473 | 34-61 | 100% |
| Seq ID NO: 64477 | 14-41 | gi|2454547 | 227-200 | 100% |
| Seq ID NO: 64477 | 14-41 | gi|551594 | 194-221 | 100% |
| Seq ID NO: 64477 | 14-41 | gi|551595 | 669-696 | 100% |
| Seq ID NO: 64477 | 14-41 | gi|18032254 | 34-61 | 100% |
| Seq ID NO: 64477 | 18-41 | gi|18477256 | 279-256 | 100% |
| Seq ID NO: 64477 | 18-41 | gi|18477260 | 325-302 | 100% |
| Seq ID NO: 64477 | 18-41 | gi|18477262 | 634-611 | 100% |
| Seq ID NO: 64477 | 14-35 | gi|18477259 | 22-1 | 100% |
| Seq ID NO: 64477 | 14-35 | gi|18477261 | 22-1 | 100% |
| Seq ID NO: 64477 | 14-35 | gi|37780968 | 22-1 | 100% |
| Seq ID NO: 64508 | 27-157 | gi|32324692 | 9-139 | 97% |
| Seq ID NO: 64514 | 52-204 | gi|32324211 | 369-521 | 85% |
| Seq ID NO: 64570 | 21-138 | gi|28916076 | 1-119 | 91% |
| Seq ID NO: 64570 | 14-41 | gi|159473 | 34-61 | 100% |
| Seq ID NO: 64570 | 14-41 | gi|2454547 | 227-200 | 100% |
| Seq ID NO: 64570 | 14-41 | gi|551594 | 194-221 | 100% |
| Seq ID NO: 64570 | 14-41 | gi|551595 | 669-696 | 100% |
| Seq ID NO: 64570 | 14-41 | gi|18032254 | 34-61 | 100% |
| Seq ID NO: 64570 | 18-41 | gi|18477256 | 279-256 | 100% |
| Seq ID NO: 64570 | 18-41 | gi|18477260 | 325-302 | 100% |
| Seq ID NO: 64570 | 18-41 | gi|18477262 | 634-611 | 100% |
| Seq ID NO: 64570 | 14-35 | gi|18477259 | 22-1 | 100% |
| Seq ID NO: 64570 | 14-35 | gi|18477261 | 22-1 | 100% |
| Seq ID NO: 64570 | 14-35 | gi|37780968 | 22-1 | 100% |
| Seq ID NO: 64580 | 33-147 | gi|32325191 | 1-115 | 92% |
| Seq ID NO: 64633 | 2-114 | gi|33140530 | 1-113 | 100% |
| Seq ID NO: 64669 | 300-320 | gi|52129537 | 617-637 | 100% |
| Seq ID NO: 64692 | 1-57 | gi|30028941 | 55-111 | 98% |
| Seq ID NO: 64692 | 1-57 | gi|33140204 | 55-111 | 98% |
| Seq ID NO: 64694 | 95-147 | gi|30028941 | 402-454 | 100% |
| Seq ID NO: 64694 | 1-43 | gi|30028941 | 308-350 | 100% |
| Seq ID NO: 64694 | 95-146 | gi|30029072 | 395-446 | 100% |
| Seq ID NO: 64694 | 95-146 | gi|33140204 | 402-453 | 100% |
| Seq ID NO: 64694 | 1-43 | gi|33140204 | 308-350 | 100% |
| Seq ID NO: 64711 | 1-93 | gi|33139524 | 233-141 | 98% |

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 64760 | 19-144 | gi|54546846 | 257-383 | 84% |
| Seq ID NO: 64762 | 174-194 | gi|9829276 | 404-424 | 100% |
| Seq ID NO: 64762 | 174-194 | gi|39747004 | 520-540 | 100% |
| Seq ID NO: 64780 | 1-118 | gi|33140548 | 49-166 | 95% |
| Seq ID NO: 64780 | 151-225 | gi|33140548 | 199-273 | 100% |
| Seq ID NO: 64797 | 33-77 | gi|54549640 | 11-55 | 93% |
| Seq ID NO: 64847 | 42-190 | gi|33140348 | 108-255 | 92% |
| Seq ID NO: 64847 | 1-70 | gi|33140348 | 105-174 | 92% |
| Seq ID NO: 64847 | 1-28 | gi|32324498 | 17-44 | 96% |
| Seq ID NO: 64862 | 7-144 | gi|7144222 | 169-306 | 92% |
| Seq ID NO: 64862 | 7-144 | gi|54547280 | 139-276 | 92% |
| Seq ID NO: 64862 | 32-149 | gi|51334182 | 168-285 | 88% |
| Seq ID NO: 64862 | 27-146 | gi|21494008 | 204-323 | 86% |
| Seq ID NO: 64874 | 205-293 | gi|18082074 | 129-217 | 83% |
| Seq ID NO: 64931 | 21-41 | gi|46984838 | 273-293 | 100% |
| Seq ID NO: 64935 | 1-84 | gi|16797830 | 749-832 | 98% |
| Seq ID NO: 64935 | 1-84 | gi|16797832 | 747-830 | 98% |
| Seq ID NO: 64935 | 1-84 | gi|26000759 | 745-828 | 98% |
| Seq ID NO: 64935 | 1-84 | gi|31442320 | 746-829 | 98% |
| Seq ID NO: 64935 | 1-84 | gi|31442322 | 746-829 | 97% |
| Seq ID NO: 64935 | 1-77 | gi|16797831 | 747-823 | 98% |
| Seq ID NO: 64935 | 8-84 | gi|21885259 | 776-852 | 97% |
| Seq ID NO: 65078 | 15-54 | gi|28916076 | 1-40 | 97% |
| Seq ID NO: 65084 | 1-166 | gi|35504916 | 448-612 | 94% |
| Seq ID NO: 65084 | 1-85 | gi|35504725 | 448-533 | 94% |
| Seq ID NO: 65205 | 338-610 | gi|33140653 | 131-403 | 100% |
| Seq ID NO: 65205 | 160-291 | gi|33140653 | 1-132 | 97% |
| Seq ID NO: 65205 | 663-717 | gi|33140653 | 401-455 | 100% |
| Seq ID NO: 65205 | 725-746 | gi|33140653 | 463-484 | 100% |
| Seq ID NO: 65205 | 338-462 | gi|32325169 | 130-254 | 100% |
| Seq ID NO: 65205 | 161-291 | gi|32325169 | 1-131 | 97% |
| Seq ID NO: 65205 | 500-610 | gi|32325169 | 254-364 | 100% |
| Seq ID NO: 65205 | 162-291 | gi|33139964 | 1-130 | 98% |
| Seq ID NO: 65261 | 1-243 | gi|33140806 | 9-255 | 95% |
| Seq ID NO: 65261 | 62-234 | gi|33139704 | 24-199 | 95% |
| Seq ID NO: 46445 | 556-665 | gi|33139443 | 1-111 | 95% |
| Seq ID NO: 65328 | 1-145 | gi|18090481 | 97-241 | 85% |
| Seq ID NO: 46452 | 1-163 | gi|7143710 | 57-220 | 89% |
| Seq ID NO: 46452 | 1-171 | gi|54549870 | 42-213 | 89% |
| Seq ID NO: 46452 | 16-163 | gi|18089601 | 5-153 | 90% |
| Seq ID NO: 46452 | 29-163 | gi|54547929 | 1-136 | 90% |
| Seq ID NO: 46452 | 1-171 | gi|51237630 | 23-194 | 85% |
| Seq ID NO: 65377 | 274-524 | gi|33140174 | 121-371 | 98% |
| Seq ID NO: 65377 | 109-229 | gi|33140174 | 1-121 | 99% |
| Seq ID NO: 65377 | 578-680 | gi|33140174 | 372-474 | 100% |
| Seq ID NO: 65377 | 274-527 | gi|32324003 | 302-555 | 98% |
| Seq ID NO: 65377 | 1-229 | gi|32324003 | 74-302 | 97% |
| Seq ID NO: 65377 | 579-621 | gi|32324003 | 554-596 | 97% |
| Seq ID NO: 65377 | 42-229 | gi|32324933 | 13-200 | 97% |
| Seq ID NO: 65377 | 579-680 | gi|32324933 | 452-553 | 99% |
| Seq ID NO: 65397 | 90-152 | gi|18081066 | 414-476 | 90% |
| Seq ID NO: 65474 | 2-53 | gi|28916076 | 52-1 | 94% |
| Seq ID NO: 65474 | 33-59 | gi|159473 | 61-35 | 100% |
| Seq ID NO: 65474 | 33-59 | gi|2454547 | 200-226 | 100% |
| Seq ID NO: 65474 | 33-59 | gi|551594 | 221-195 | 100% |
| Seq ID NO: 65474 | 33-59 | gi|551595 | 696-670 | 100% |
| Seq ID NO: 65474 | 33-59 | gi|18032254 | 61-35 | 100% |
| Seq ID NO: 65474 | 33-56 | gi|18477256 | 256-279 | 100% |
| Seq ID NO: 65474 | 33-56 | gi|18477260 | 302-325 | 100% |
| Seq ID NO: 65474 | 33-56 | gi|18477262 | 611-634 | 100% |
| Seq ID NO: 65474 | 39-59 | gi|18477259 | 1-21 | 100% |
| Seq ID NO: 65474 | 39-59 | gi|18477261 | 1-21 | 100% |
| Seq ID NO: 65474 | 39-59 | gi|37780968 | 1-21 | 100% |
| Seq ID NO: 65553 | 1-63 | gi|33140188 | 109-171 | 98% |
| Seq ID NO: 65553 | 2-50 | gi|33140188 | 305-353 | 90% |
| Seq ID NO: 65558 | 14-173 | gi|18383267 | 801-960 | 86% |
| Seq ID NO: 65560 | 480-623 | gi|35504861 | 212-70 | 97% |
| Seq ID NO: 65572 | 411-582 | gi|33139585 | 153-324 | 94% |
| Seq ID NO: 65572 | 135-258 | gi|33139585 | 1-124 | 96% |
| Seq ID NO: 65591 | 217-309 | gi|32324909 | 25-117 | 93% |
| Seq ID NO: 46459 | 203-386 | gi|18081711 | 111-294 | 86% |
| Seq ID NO: 46459 | 1-35 | gi|54549088 | 64-98 | 94% |
| Seq ID NO: 46459 | 14-35 | gi|54549319 | 1-22 | 100% |
| Seq ID NO: 65643 | 1-194 | gi|33140010 | 238-431 | 96% |
| Seq ID NO: 65643 | 121-194 | gi|33139314 | 1-74 | 97% |
| Seq ID NO: 46465 | 159-238 | gi|9829340 | 394-315 | 87% |
| Seq ID NO: 65738 | 166-205 | gi|33140813 | 1-40 | 95% |
| Seq ID NO: 65755 | 83-126 | gi|551594 | 1028-1070 | 93% |
| Seq ID NO: 65755 | 83-126 | gi|551595 | 267-309 | 93% |
| Seq ID NO: 65813 | 1-121 | gi|28916076 | 122-1 | 91% |
| Seq ID NO: 65813 | 101-126 | gi|159473 | 61-36 | 100% |
| Seq ID NO: 65813 | 101-126 | gi|2454547 | 200-225 | 100% |
| Seq ID NO: 65813 | 101-126 | gi|551594 | 221-196 | 100% |
| Seq ID NO: 65813 | 101-126 | gi|551595 | 696-671 | 100% |
| Seq ID NO: 65813 | 101-126 | gi|18032254 | 61-36 | 100% |
| Seq ID NO: 65813 | 101-124 | gi|18477256 | 256-279 | 100% |
| Seq ID NO: 65813 | 101-124 | gi|18477260 | 302-325 | 100% |
| Seq ID NO: 65813 | 101-124 | gi|18477262 | 611-634 | 100% |
| Seq ID NO: 65831 | 80-203 | gi|33140348 | 128-252 | 92% |
| Seq ID NO: 65932 | 77-335 | gi|33139639 | 245-503 | 87% |
| Seq ID NO: 65932 | 70-225 | gi|33140673 | 199-44 | 88% |
| Seq ID NO: 65932 | 245-349 | gi|32324211 | 165-269 | 86% |
| Seq ID NO: 65932 | 293-327 | gi|33139131 | 293-327 | 94% |
| Seq ID NO: 65966 | 1-215 | gi|33140309 | 306-520 | 97% |
| Seq ID NO: 66029 | 1-143 | gi|16797830 | 62-204 | 98% |
| Seq ID NO: 66029 | 1-143 | gi|16797831 | 62-202 | 97% |
| Seq ID NO: 66029 | 1-143 | gi|16797832 | 63-203 | 97% |
| Seq ID NO: 66029 | 1-143 | gi|26000759 | 62-202 | 96% |
| Seq ID NO: 66029 | 1-142 | gi|26000762 | 62-201 | 95% |
| Seq ID NO: 66029 | 1-143 | gi|31442322 | 62-202 | 95% |
| Seq ID NO: 66029 | 1-143 | gi|38096133 | 62-202 | 93% |
| Seq ID NO: 46479 | 143-293 | gi|18090185 | 96-246 | 90% |
| Seq ID NO: 46479 | 412-474 | gi|18090185 | 320-382 | 92% |
| Seq ID NO: 66115 | 83-126 | gi|551594 | 1028-1070 | 93% |
| Seq ID NO: 66115 | 83-126 | gi|551595 | 267-309 | 93% |
| Seq ID NO: 66138 | 21-168 | gi|54546322 | 121-268 | 87% |
| Seq ID NO: 66223 | 311-331 | gi|32184515 | 225-245 | 100% |
| Seq ID NO: 66245 | 118-139 | gi|54544778 | 203-224 | 100% |
| Seq ID NO: 46493 | 113-266 | gi|33139869 | 326-476 | 92% |
| Seq ID NO: 46493 | 115-269 | gi|18080529 | 142-293 | 90% |
| Seq ID NO: 46493 | 113-240 | gi|32325143 | 467-591 | 91% |
| Seq ID NO: 46493 | 113-229 | gi|33139507 | 467-580 | 92% |
| Seq ID NO: 46493 | 113-236 | gi|33139658 | 467-587 | 91% |
| Seq ID NO: 46493 | 113-217 | gi|33139078 | 467-568 | 91% |
| Seq ID NO: 46493 | 171-286 | gi|7143888 | 280-392 | 89% |
| Seq ID NO: 46493 | 113-216 | gi|33140145 | 467-567 | 91% |
| Seq ID NO: 46493 | 186-269 | gi|18080754 | 174-257 | 92% |
| Seq ID NO: 46493 | 144-269 | gi|52129866 | 585-708 | 86% |
| Seq ID NO: 46493 | 192-286 | gi|18080844 | 1-95 | 89% |
| Seq ID NO: 46493 | 144-254 | gi|52129769 | 700-808 | 87% |
| Seq ID NO: 46493 | 113-190 | gi|32324728 | 467-544 | 92% |
| Seq ID NO: 46493 | 113-204 | gi|33140539 | 467-555 | 90% |
| Seq ID NO: 46493 | 118-239 | gi|19264211 | 454-572 | 82% |
| Seq ID NO: 46493 | 211-245 | gi|22140574 | 144-178 | 97% |
| Seq ID NO: 46493 | 220-254 | gi|52129262 | 3-37 | 94% |
| Seq ID NO: 46493 | 113-182 | gi|15784199 | 440-509 | 84% |
| Seq ID NO: 46493 | 113-148 | gi|15785306 | 458-492 | 91% |
| Seq ID NO: 66327 | 1-81 | gi|35504440 | 192-272 | 95% |
| Seq ID NO: 66372 | 317-509 | gi|54546686 | 284-476 | 85% |
| Seq ID NO: 66372 | 454-509 | gi|33139916 | 1-56 | 100% |
| Seq ID NO: 66454 | 23-43 | gi|21285223 | 168-148 | 100% |
| Seq ID NO: 66513 | 28-80 | gi|54545135 | 100-152 | 96% |
| Seq ID NO: 66513 | 154-198 | gi|54549414 | 410-454 | 93% |
| Seq ID NO: 66513 | 38-80 | gi|54548968 | 1-43 | 95% |
| Seq ID NO: 66611 | 1-107 | gi|33140780 | 433-539 | 98% |
| Seq ID NO: 46522 | 1-101 | gi|18382566 | 65-165 | 89% |
| Seq ID NO: 46522 | 6-101 | gi|18089815 | 1-96 | 88% |
| Seq ID NO: 46522 | 64-98 | gi|21493534 | 40-74 | 91% |
| Seq ID NO: 66645 | 80-246 | gi|32324211 | 1-167 | 86% |
| Seq ID NO: 66645 | 69-219 | gi|33140673 | 199-49 | 83% |
| Seq ID NO: 66645 | 87-219 | gi|33139639 | 256-388 | 83% |
| Seq ID NO: 66691 | 1-141 | gi|16797830 | 62-202 | 98% |
| Seq ID NO: 66691 | 1-141 | gi|16797831 | 62-200 | 97% |
| Seq ID NO: 66691 | 1-141 | gi|16797832 | 63-201 | 97% |
| Seq ID NO: 66691 | 1-141 | gi|26000759 | 62-200 | 96% |
| Seq ID NO: 66691 | 1-141 | gi|31442322 | 62-200 | 95% |
| Seq ID NO: 66691 | 1-141 | gi|38096133 | 62-200 | 93% |
| Seq ID NO: 66692 | 1-160 | gi|5107411 | 189-30 | 100% |

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 66692 | 1-160 | gi|2149587 | 189-30 | 95% |
| Seq TABLE 2-continued Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 69089 | 12-35 | gi|18477262 | 634-611 | 100% |
| Seq ID NO: 69089 | 8-29 | gi|18477259 | 22-1 | 100% |
| Seq ID NO: 69089 | 8-29 | gi|18477261 | 22-1 | 100% |
| Seq ID NO: 69089 | 8-29 | gi|37780968 | 22-1 | 100% |
| Seq ID NO: 69170 | 15-54 | gi|28916076 | 1-40 | 97% |
| Seq ID NO: 69170 | 8-35 | gi|159473 | 34-61 | 100% |
| Seq ID NO: 69170 | 8-35 | gi|2454547 | 227-200 | 100% |
| Seq ID NO: 69170 | 8-35 | gi|551594 | 194-221 | 100% |
| Seq ID NO: 69170 | 8-35 | gi|551595 | 669-696 | 100% |
| Seq ID NO: 69170 | 8-35 | gi|18032254 | 34-61 | 100% |
| Seq ID NO: 69170 | 12-35 | gi|18477256 | 279-256 | 100% |
| Seq ID NO: 69170 | 12-35 | gi|18477260 | 325-302 | 100% |
| Seq ID NO: 69170 | 12-35 | gi|18477262 | 634-611 | 100% |
| Seq ID NO: 69170 | 8-29 | gi|18477259 | 22-1 | 100% |
| Seq ID NO: 69170 | 8-29 | gi|18477261 | 22-1 | 100% |
| Seq ID NO: 69170 | 8-29 | gi|37780968 | 22-1 | 100% |
| Seq ID NO: 69314 | 36-174 | gi|28916076 | 140-1 | 92% |
| Seq ID NO: 69314 | 154-181 | gi|159473 | 61-34 | 100% |
| Seq ID NO: 69314 | 154-181 | gi|2454547 | 200-227 | 100% |
| Seq ID NO: 69314 | 154-181 | gi|551594 | 221-194 | 100% |
| Seq ID NO: 69314 | 154-181 | gi|551595 | 696-669 | 100% |
| Seq ID NO: 69314 | 154-181 | gi|18032254 | 61-34 | 100% |
| Seq ID NO: 69314 | 154-177 | gi|18477256 | 256-279 | 100% |
| Seq ID NO: 69314 | 154-177 | gi|18477260 | 302-325 | 100% |
| Seq ID NO: 69314 | 154-177 | gi|18477262 | 611-634 | 100% |
| Seq ID NO: 69314 | 160-181 | gi|18477259 | 1-22 | 100% |
| Seq ID NO: 69314 | 160-181 | gi|18477261 | 1-22 | 100% |
| Seq ID NO: 69314 | 160-181 | gi|37780968 | 1-22 | 100% |
| Seq ID NO: 69324 | 1-369 | gi|51093880 | 722-352 | 84% |
| Seq ID NO: 69324 | 1-369 | gi|51093884 | 722-352 | 83% |
| Seq ID NO: 69324 | 1-252 | gi|51093883 | 723-469 | 85% |
| Seq ID NO: 69324 | 313-369 | gi|51093883 | 407-352 | 91% |
| Seq ID NO: 69324 | 134-369 | gi|51093882 | 587-352 | 84% |
| Seq ID NO: 69324 | 134-369 | gi|54545658 | 621-387 | 83% |
| Seq ID NO: 69327 | 1-128 | gi|33139874 | 74-201 | 90% |
| Seq ID NO: 69351 | 1-124 | gi|33140792 | 30-153 | 98% |
| Seq ID NO: 69351 | 43-124 | gi|45643642 | 1-82 | 98% |
| Seq ID NO: 69351 | 58-124 | gi|45643646 | 1-67 | 92% |
| Seq ID NO: 46651 | 3-78 | gi|18081363 | 236-310 | 96% |
| Seq ID NO: 46651 | 3-76 | gi|54544882 | 242-315 | 95% |
| Seq ID NO: 69410 | 1-141 | gi|16797830 | 62-202 | 98% |
| Seq ID NO: 69410 | 1-141 | gi|16797831 | 62-200 | 97% |
| Seq ID NO: 69410 | 1-141 | gi|16797832 | 63-201 | 97% |
| Seq ID NO: 69410 | 1-141 | gi|26000759 | 62-200 | 96% |
| Seq ID NO: 69410 | 1-141 | gi|31442322 | 62-200 | 95% |
| Seq ID NO: 69410 | 1-141 | gi|38096133 | 62-200 | 93% |
| Seq ID NO: 69440 | 221-245 | gi|46987193 | 49-25 | 96% |
| Seq ID NO: 69448 | 1-53 | gi|18081057 | 88-140 | 94% |
| Seq ID NO: 69449 | 42-186 | gi|35504946 | 49-193 | 97% |
| Seq ID NO: 69463 | 1-156 | gi|54548643 | 39-188 | 87% |
| Seq ID NO: 69463 | 21-156 | gi|18089480 | 9-138 | 86% |
| Seq ID NO: 69489 | 1-118 | gi|16797830 | 147-264 | 99% |
| Seq ID NO: 69489 | 1-118 | gi|26000761 | 147-262 | 95% |
| Seq ID NO: 69489 | 1-118 | gi|16797832 | 148-263 | 94% |
| Seq ID NO: 69489 | 1-118 | gi|47118286 | 171-286 | 94% |
| Seq ID NO: 69489 | 1-118 | gi|31442322 | 147-262 | 94% |
| Seq ID NO: 69489 | 1-118 | gi|21885259 | 169-284 | 91% |
| Seq ID NO: 69494 | 323-427 | gi|33139639 | 245-349 | 90% |
| Seq ID NO: 69494 | 316-441 | gi|33140673 | 199-74 | 86% |
| Seq ID NO: 69501 | 113-190 | gi|54549674 | 422-500 | 94% |
| Seq ID NO: 69501 | 13-53 | gi|54549674 | 321-361 | 95% |
| Seq ID NO: 69570 | 16-153 | gi|7143498 | 58-196 | 85% |
| Seq ID NO: 69592 | 1-136 | gi|16797830 | 686-821 | 100% |
| Seq ID NO: 69592 | 1-136 | gi|16797832 | 684-819 | 100% |
| Seq ID NO: 69592 | 1-136 | gi|31442320 | 683-818 | 100% |
| Seq ID NO: 69592 | 1-136 | gi|26000759 | 682-817 | 99% |
| Seq ID NO: 69592 | 1-136 | gi|31442322 | 683-818 | 99% |
| Seq ID NO: 69592 | 1-136 | gi|38096133 | 685-820 | 97% |
| Seq ID NO: 69592 | 1-120 | gi|16797846 | 702-824 | 90% |
| Seq ID NO: 69592 | 1-120 | gi|16797847 | 692-814 | 90% |
| Seq ID NO: 69592 | 1-120 | gi|14600264 | 704-826 | 90% |
| Seq ID NO: 69592 | 1-80 | gi|16797841 | 691-769 | 97% |
| Seq ID NO: 69592 | 1-80 | gi|16797843 | 725-803 | 97% |
| Seq ID NO: 69592 | 1-114 | gi|16797848 | 691-807 | 90% |
| Seq ID NO: 69592 | 1-80 | gi|16797849 | 692-770 | 97% |
| Seq ID NO: 69593 | 1-68 | gi|5107411 | 156-89 | 100% |
| Seq ID NO: 69593 | 14-68 | gi|34105813 | 1719-1665 | 100% |
| Seq ID NO: 69593 | 1-51 | gi|2149587 | 156-106 | 100% |
| Seq ID NO: 69593 | 1-48 | gi|2738785 | 157-110 | 100% |
| Seq ID NO: 69593 | 1-48 | gi|2738792 | 157-110 | 100% |
| Seq ID NO: 69593 | 1-48 | gi|2738799 | 157-110 | 100% |
| Seq ID NO: 69593 | 1-48 | gi|2738800 | 157-110 | 100% |
| Seq ID NO: 69593 | 1-54 | gi|2149585 | 156-103 | 96% |
| Seq ID NO: 69593 | 1-47 | gi|31074278 | 1741-1695 | 97% |
| Seq ID NO: 69593 | 1-47 | gi|31074279 | 1741-1695 | 97% |
| Seq ID NO: 69593 | 1-47 | gi|48479719 | 158-112 | 97% |
| Seq ID NO: 69593 | 1-47 | gi|37674501 | 161-115 | 97% |
| Seq ID NO: 69593 | 1-45 | gi|30844179 | 1735-1691 | 97% |
| Seq ID NO: 69716 | 1-121 | gi|28916076 | 122-1 | 91% |
| Seq ID NO: 69716 | 101-128 | gi|159473 | 61-34 | 100% |
| Seq ID NO: 69716 | 101-128 | gi|2454547 | 200-227 | 100% |
| Seq ID NO: 69716 | 101-128 | gi|551594 | 221-194 | 100% |
| Seq ID NO: 69716 | 101-128 | gi|551595 | 696-669 | 100% |
| Seq ID NO: 69716 | 101-128 | gi|18032254 | 61-34 | 100% |
| Seq ID NO: 69716 | 101-124 | gi|18477256 | 256-279 | 100% |
| Seq ID NO: 69716 | 101-124 | gi|18477260 | 302-325 | 100% |
| Seq ID NO: 69716 | 101-124 | gi|18477262 | 611-634 | 100% |
| Seq ID NO: 69716 | 107-128 | gi|18477259 | 1-22 | 100% |
| Seq ID NO: 69716 | 107-128 | gi|18477261 | 1-22 | 100% |
| Seq ID NO: 69716 | 107-128 | gi|37780968 | 1-22 | 100% |
| Seq ID NO: 69747 | 6-258 | gi|51093884 | 252-7 | 91% |
| Seq ID NO: 69747 | 6-258 | gi|18080808 | 295-50 | 89% |
| Seq ID NO: 69747 | 207-258 | gi|18032252 | 2936-2885 | 92% |
| Seq ID NO: 69747 | 219-252 | gi|30049837 | 62-29 | 97% |
| Seq ID NO: 69747 | 219-252 | gi|20064115 | 400-367 | 94% |
| Seq ID NO: 69747 | 219-251 | gi|19267510 | 33-1 | 94% |
| Seq ID NO: 69747 | 219-241 | gi|19268366 | 27-5 | 100% |
| Seq ID NO: 69795 | 145-251 | gi|52129366 | 202-308 | 85% |
| Seq ID NO: 69795 | 50-74 | gi|52129366 | 161-185 | 100% |
| Seq ID NO: 69821 | 1-101 | gi|32324237 | 442-541 | 98% |
| Seq ID NO: 46679 | 448-820 | gi|33139644 | 1-373 | 93% |
| Seq ID NO: 46679 | 1053-1213 | gi|33139644 | 387-546 | 95% |
| Seq ID NO: 69829 | 21-138 | gi|28916076 | 1-119 | 91% |
| Seq ID NO: 69829 | 14-41 | gi|159473 | 34-61 | 100% |
| Seq ID NO: 69829 | 14-41 | gi|2454547 | 227-200 | 100% |
| Seq ID NO: 69829 | 14-41 | gi|551594 | 194-221 | 100% |
| Seq ID NO: 69829 | 14-41 | gi|551595 | 669-696 | 100% |
| Seq ID NO: 69829 | 14-41 | gi|18032254 | 34-61 | 100% |
| Seq ID NO: 69829 | 18-41 | gi|18477256 | 279-256 | 100% |
| Seq ID NO: 69829 | 18-41 | gi|18477260 | 325-302 | 100% |
| Seq ID NO: 69829 | 18-41 | gi|18477262 | 634-611 | 100% |
| Seq ID NO: 69829 | 14-35 | gi|18477259 | 22-1 | 100% |
| Seq ID NO: 69829 | 14-35 | gi|18477261 | 22-1 | 100% |
| Seq ID NO: 69829 | 14-35 | gi|37780968 | 22-1 | 100% |
| Seq ID NO: 69838 | 1-98 | gi|18382603 | 1075-978 | 89% |
| Seq ID NO: 69838 | 25-98 | gi|18382603 | 520-447 | 91% |
| Seq ID NO: 69893 | 21-138 | gi|28916076 | 1-119 | 91% |
| Seq ID NO: 69893 | 14-41 | gi|159473 | 34-61 | 100% |
| Seq ID NO: 69893 | 14-41 | gi|2454547 | 227-200 | 100% |
| Seq ID NO: 69893 | 14-41 | gi|551594 | 194-221 | 100% |
| Seq ID NO: 69893 | 14-41 | gi|551595 | 669-696 | 100% |
| Seq ID NO: 69893 | 14-41 | gi|18032254 | 34-61 | 100% |
| Seq ID NO: 69893 | 18-41 | gi|18477256 | 279-256 | 100% |
| Seq ID NO: 69893 | 18-41 | gi|18477260 | 325-302 | 100% |
| Seq ID NO: 69893 | 18-41 | gi|18477262 | 634-611 | 100% |
| Seq ID NO: 69893 | 14-35 | gi|18477259 | 22-1 | 100% |
| Seq ID NO: 69893 | 14-35 | gi|18477261 | 22-1 | 100% |
| Seq ID NO: 69893 | 14-35 | gi|37780968 | 22-1 | 100% |
| Seq ID NO: 69930 | 1-65 | gi|14280572 | 7058-7122 | 100% |
| Seq ID NO: 69972 | 1-247 | gi|47118286 | 742-988 | 97% |
| Seq ID NO: 69972 | 1-247 | gi|47118285 | 729-975 | 96% |
| Seq ID NO: 69972 | 1-230 | gi|16797830 | 720-950 | 96% |
| Seq ID NO: 69972 | 1-230 | gi|21885260 | 740-969 | 96% |
| Seq ID NO: 69972 | 1-230 | gi|31442322 | 717-946 | 96% |
| Seq ID NO: 69972 | 1-230 | gi|26000759 | 716-945 | 96% |
| Seq ID NO: 69972 | 1-230 | gi|31442320 | 717-946 | 96% |
| Seq ID NO: 69972 | 1-230 | gi|38096133 | 719-948 | 94% |
| Seq ID NO: 69972 | 1-44 | gi|16797827 | 765-807 | 95% |

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 69972 | 142-170 | gi\|16797844 | 862-890 | 96% |
| Seq ID NO: 69972 | 227-247 | gi\|48479719 | 1112-1132 | 100% |
| Seq ID NO: 69978 | 1-157 | gi\|33139812 | 208-364 | 98% |
| Seq ID NO: 69998 | 1-79 | gi\|28916077 | 109-31 | 87% |
| Seq ID NO: 70006 | 213-380 | gi\|33139204 | 1-168 | 98% |
| Seq ID NO: 70006 | 96-177 | gi\|33139204 | 462-542 | 97% |
| Seq ID NO: 70006 | 96-214 | gi\|33139268 | 461-579 | 98% |
| Seq ID NO: 70072 | 1-107 | gi\|18087923 | 4-110 | 87% |
| Seq ID NO: 70072 | 34-68 | gi\|51237696 | 40-74 | 91% |
| Seq ID NO: 70096 | 21-138 | gi\|28916076 | 1-119 | 91% |
| Seq ID NO: 70096 | 14-41 | gi\|159473 | 34-61 | 100% |
| Seq ID NO: 70096 | 14-41 | gi\|2454547 | 227-200 | 100% |
| Seq ID NO: 70096 | 14-41 | gi\|551594 | 194-221 | 100% |
| Seq ID NO: 70096 | 14-41 | gi\|551595 | 669-696 | 100% |
| Seq ID NO: 70096 | 14-41 | gi\|18032254 | 34-61 |

TABLE 2-continued

Diverse Parasitic Nematode Nucleotide Coding Sequences Matching *H. glycines* vcDNA sequences

| *H. glycines* Sequence[1] | Position[2] | GeneID[3] | Position[4] | % identity[5] |
|---|---|---|---|---|
| Seq ID NO: 71227 | 18-127 | gi|31442313 | 354-246 | 85% |
| Seq ID NO: 71249 | 1-138 | gi|33140698 | 375-512 | 97% |
| Seq ID NO: 71249 | 147-190 | gi|33140698 | 521-564 | 97% |
| Seq ID NO: 71288 | 1-134 | gi|16797830 | 935-802 | 97% |
| Seq ID NO: 71288 | 1-134 | gi|26000759 | 931-798 | 97% |
| Seq ID NO: 71288 | 1-134 | gi|31442322 | 932-799 | 97% |
| Seq ID NO: 71288 | 1-134 | gi|16797832 | 933-800 | 96% |
| Seq ID NO: 71288 | 1-134 | gi|47118286 | 957-824 | 96% |
| Seq ID NO: 71288 | 1-122 | gi|26000763 | 930-809 | 97% |
| Seq ID NO: 71288 | 1-133 | gi|16797831 | 933-801 | 95% |
| Seq ID NO: 71288 |

TABLE 2-continued

Diverse Parasitic Nematode Nucleotide Coding Sequences Matching *H. glycines* vcDNA sequences

| H. glycines Sequence[1] |

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 77038 | 17-123 | gi|30844179 | 1550-1444 | 95% |
| Seq ID NO: 77038 | 17-123 | gi|34105807 | 1434-1328 | 95% |
| Seq ID NO: 77038 | 17-123 | gi|34105808 | 1545-1439 | 95% |
| Seq ID NO: 77038 | 17-123 | gi|34105810 | 1561-1455 | 95% |
| Seq ID NO: 77038 | 17-123 | gi|31376322 | 1492-1386 | 94% |
| Seq ID NO: 77038 | 17-123 | gi|31376323 | 1488-1382 | 94% |
| Seq ID NO: 77038 | 17-123 | gi|34105806 | 1558-1452 | 93% |
| Seq ID NO: 77038 | 17-123 | gi|51093982 | 386-280 | 93% |
| Seq ID NO: 77038 | 17-123 | gi|6983959 | 1511-1405 | 92% |
| Seq ID NO: 77038 | 17-123 | gi|22544385 | 274-168 | 92% |
| Seq ID NO: 77038 | 17-123 | gi|30169951 | 41-147 | 92% |
| Seq ID NO: 77038 | 17-123 | gi|31376325 | 1503-1397 | 92% |
| Seq ID NO: 77198 | 308-501 | gi|33140188 | 263-70 | 96% |
| Seq ID NO: 77198 | 302-469 | gi|33140188 | 464-297 | 87% |
| Seq ID NO: 77198 | 4-91 | gi|33140188 | 353-266 | 97% |
| Seq ID NO: 77198 | 1-88 | gi|33140188 | 551-464 | 90% |
| Seq ID NO: 77198 | 389-469 | gi|33140188 | 572-492 | 91% |
|

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 81813 | 664-822 | gi|32323963 | 132-290 | 98% |
| Seq ID NO: 81813 | 877-972 | gi|32323963 | 290-385 | 98% |
| Seq ID NO: 81813 | 877-971 | gi|32325615 | 290-384 | 98% |
| Seq ID NO: 81813 | 427-539 | gi|33139274 | 1-113 | 97% |
| Seq ID NO: 81813 | 429-606 | gi|33140556 | 1-181 | 92% |
| Seq ID NO: 81813 | 666-822 | gi|32324994 | 135-291 | 98% |
| Seq ID NO: 81813 | 428-539 | gi|32324994 | 1-112 | 99% |
| Seq ID NO: 81813 | 877-947 | gi|33139381 | 232-302 | 98% |
| Seq ID NO: 81813 | 487-539 | gi|33139381 | 1-53 | 100% |
| Seq ID NO: 81813 | 427-523 | gi|33140583 | 1-97 | 96% |
| Seq ID NO: 81817 | 452-473 | gi|33952321 | 139-160 | 100% |
| Seq ID NO: 81839 | 16-77 | gi|7143651 | 36-97 | 90% |
| Seq ID NO: 81895 | 515-875 | gi|32325036 | 211-571 | 95% |
| Seq ID NO: 81895 | 472-827 | gi|32325036 | 216-571 | 94% |
| Seq ID NO: 81895 | 563-897 | gi|32325036 | 211-545 | 94% |
| Seq ID NO: 81895 | 514-693 | gi|32325036 | 18-197 | 93% |
| Seq ID NO: 81895 | 482-645 | gi|32325036 | 34-197 | 94% |
| Seq ID NO: 81895 | 610-789 | gi|32325036 | 18-197 | 92% |
| Seq ID NO: 81895 | 562-741 | gi|32325036 | 18-197 | 92% |
| Seq ID NO: 81895 | 658-837 | gi|32325036 | 18-197 | 92% |
| Seq ID NO: 81895 | 706-885 | gi|32325036 | 18-197 | 92% |
| Seq ID NO: 81895 | 754-897 | gi|32325036 | 18-161 | 93% |
| Seq ID NO: 81895 | 472-597 | gi|32325036 | 72-197 | 93% |
| Seq ID NO: 81895 | 48-246 | gi|32325036 | 231-428 | 86% |
| Seq ID NO: 81895 | 1-246 | gi|32325036 | 232-476 | 83% |
| Seq ID NO: 81895 | 137-270 | gi|32325036 | 224-356 | 87% |
| Seq ID NO: 81895 | 48-207 | gi|32325036 | 39-197 | 83% |
| Seq ID NO: 81895 | 138-253 | gi|32325036 | 33-147 | 86% |
| Seq ID NO: 81895 | 1-157 | gi|32325036 | 40-196 | 80% |
| Seq ID NO: 81895 | 470-716 | gi|33140561 | 167-413 | 96% |
| Seq ID NO: 81895 | 520-764 | gi|33140561 | 169-413 | 95% |
| Seq ID NO: 81895 | 568-812 | gi|33140561 | 169-413 | 95% |
| Seq ID NO: 81895 | 616-860 | gi|33140561 | 169-413 | 95% |
| Seq ID NO: 81895 | 664-897 | gi|33140561 | 169-402 | 95% |
| Seq ID NO: 81895 | 457-668 | gi|33140561 | 202-413 | 95% |
| Seq ID NO: 81895 | 1-230 | gi|33140561 | 185-413 | 83% |
| Seq ID NO: 81895 | 691-712 | gi|33140561 | 412-433 | 100% |
| Seq ID NO: 81895 | 835-856 | gi|33140561 | 412-433 | 100% |
| Seq ID NO: 81895 | 547-568 | gi|33140561 | 412-433 | 100% |
| Seq ID NO: 81895 | 787-808 | gi|33140561 | 412-433 | 100% |
| Seq ID NO: 81895 | 643-664 | gi|33140561 | 412-433 | 100% |
| Seq ID NO: 81895 | 739-760 | gi|33140561 | 412-433 | 100% |
| Seq ID NO: 81895 | 595-616 | gi|33140561 | 412-433 | 100% |
| Seq ID NO: 81895 | 499-520 | gi|33140561 | 412-433 | 100% |
| Seq ID NO: 81895 | 534-896 | gi|7143587 | 175-537 | 83% |
| Seq ID NO: 81895 | 486-848 | gi|7143587 | 175-537 | 83% |
| Seq ID NO: 81895 | 484-752 | gi|7143944 | 428-699 | 82% |
| Seq ID NO: 81895 | 724-896 | gi|7143944 | 332-504 | 84% |
| Seq ID NO: 81895 | 630-728 | gi|7143944 | 133-231 | 88% |
| Seq ID NO: 81895 | 582-671 | gi|7143944 | 133-222 | 89% |
| Seq ID NO: 81895 | 534-623 | gi|7143944 | 133-222 | 89% |
| Seq ID NO: 81895 | 774-863 | gi|7143944 | 133-222 | 89% |
| Seq ID NO: 81895 | 486-575 | gi|7143944 | 133-222 | 89% |
| Seq ID NO: 81895 | 822-896 | gi|7143944 | 133-207 | 90% |
| Seq ID NO: 81895 | 678-767 | gi|7143944 | 133-222 | 86% |
| Seq ID NO: 81895 | 470-569 | gi|33139222 | 297-396 | 97% |
| Seq ID NO: 81895 | 520-617 | gi|33139222 | 299-396 | 95% |
| Seq ID NO: 81895 | 760-857 | gi|33139222 | 299-396 | 95% |
| Seq ID NO: 81895 | 616-713 | gi|33139222 | 299-396 | 95% |
| Seq ID NO: 81895 | 568-665 | gi|33139222 | 299-396 | 95% |
| Seq ID NO: 81895 | 712-809 | gi|33139222 | 299-396 | 93% |
| Seq ID NO: 81895 | 664-761 | gi|33139222 | 299-396 | 93% |
| Seq ID NO: 81895 | 808-897 | gi|33139222 | 299-388 | 95% |
| Seq ID NO: 81895 | 457-521 | gi|33139222 | 332-396 | 92% |
| Seq ID NO: 82088 | 73-93 | gi|33140421 | 13-33 | 100% |
| Seq ID NO: 82094 | 18-129 | gi|33139131 | 139-250 | 90% |
| Seq ID NO: 82094 | 31-123 | gi|32324211 | 48-140 | 90% |
| Seq ID NO: 82094 | 1-152 | gi|33139639 | 266-417 | 80% |
| Seq ID NO: 82109 | 19-196 | gi|18087933 | 464-287 | 90% |
| Seq ID NO: 82109 | 19-184 | gi|54547517 | 403-568 | 88% |
| Seq ID NO: 82109 | 19-166 | gi|18081843 | 491-638 | 89% |
| Seq ID NO: 82109 | 19-139 | gi|18083082 | 505-625 | 90% |
| Seq ID NO: 82109 | 66-191 | gi|51334233 | 404-529 | 81% |
| Seq ID NO: 82142 | 1-79 | gi|33140136 | 402-480 | 93% |
| Seq ID NO: 82163 | 122-267 | gi|33139131 | 99-244 | 87% |
| Seq ID NO: 82163 | 128-267 | gi|32324211 | 1-140 | 87% |
| Seq ID NO: 82166 | 2-106 | gi|33139639 | 245-349 | 90% |
| Seq ID NO: 82166 | 1-120 | gi|33140673 | 193-74 | 84% |
| Seq ID NO: 82199 | 66-470 | gi|33140136 | 92-496 | 89% |
| Seq ID NO: 82221 | 1-87 | gi|18090662 | 244-330 | 88% |
| Seq ID NO: 82256 | 59-122 | gi|14280572 | 6490-6553 | 92% |
| Seq ID NO: 82260 | 698-718 | gi|37972243 | 197-217 | 100% |
| Seq ID NO: 82260 | 698-718 | gi|45566049 | 213-233 | 100% |
| Seq ID NO: 47476 | 3-211 | gi|18089811 | 280-488 | 87% |
| Seq ID NO: 47476 | 3-167 | gi|18080518 | 317-481 | 88% |
| Seq ID NO: 82506 | 1-174 | gi|33140348 | 248-75 | 89% |
| Seq ID NO: 82506 | 117-155 | gi|32324498 | 44-5 | 92% |
| Seq ID NO: 82529 | 1-86 | gi|32324692 | 54-139 | 97% |
| Seq ID NO: 82529 | 7-86 | gi|18082298 | 52-131 | 90% |
| Seq ID NO: 82799 | 1-40 | gi|33140348 | 254-215 | 100% |
| Seq ID NO: 82799 | 78-135 | gi|33140348 | 181-123 | 90% |
| Seq ID NO: 82849 | 599-663 | gi|18080145 | 213-277 | 87% |
| Seq ID NO: 82849 | 358-380 | gi|40670113 | 439-417 | 100% |
| Seq ID NO: 82865 | 1-127 | gi|33140348 | 255-128 | 93% |
| Seq ID NO: 82865 | 185-227 | gi|33140348 | 70-27 | 97% |
| Seq ID NO: 82929 | 772-793 | gi|8930759 | 49-28 | 100% |
| Seq ID NO: 82929 | 772-793 | gi|34026216 | 41-20 | 100% |
| Seq ID NO: 82965 | 302-322 | gi|46984484 | 89-109 | 100% |
| Seq ID NO: 83225 | 316-338 | gi|27540675 | 36-58 | 100% |
| Seq ID NO: 83226 | 299-358 | gi|32325383 | 584-525 | 98% |
| Seq ID NO: 83249 | 3-237 | gi|33139581 | 1-235 | 99% |
| Seq ID NO: 83274 | 1-55 | gi|21393574 | 296-350 | 89% |
| Seq ID NO: 83339 | 1-268 | gi|51093880 | 722-452 | 86% |
| Seq ID NO: 83339 | 1-252 | gi|51093883 | 723-469 | 85% |
| Seq ID NO: 83339 | 134-268 | gi|51093882 | 587-452 | 87% |
| Seq ID NO: 83339 | 134-252 | gi|54545658 | 621-503 | 87% |
| Seq ID NO: 83379 | 40-139 | gi|18081804 | 201-300 | 89% |
| Seq ID NO: 83379 | 40-130 | gi|18088266 | 516-606 | 90% |
| Seq ID NO: 83382 | 42-429 | gi|32325123 | 663-276 | 87% |
| Seq ID NO: 83382 | 132-519 | gi|32325123 | 663-276 | 87% |
| Seq ID NO: 83382 | 1-384 | gi|32325123 | 659-276 | 87% |
| Seq ID NO: 83382 | 90-474 | gi|32325123 | 660-276 | 86% |
| Seq ID NO: 83382 | 3-294 | gi|32325123 | 567-276 | 89% |
| Seq ID NO: 83382 | 177-526 | gi|32325123 | 663-314 | 86% |
| Seq ID NO: 83382 | 1-204 | gi|32325123 | 479-276 | 90% |
| Seq ID NO: 83382 | 312-530 | gi|32325123 | 663-445 | 84% |
| Seq ID NO: 83382 | 1-87 | gi|32325123 | 344-258 | 94% |
| Seq ID NO: 83382 | 17-165 | gi|32325123 | 236-84 | 83% |
| Seq ID NO: 83382 | 308-435 | gi|32325123 | 214-84 | 83% |
| Seq ID NO: 83382 | 332-384 | gi|32325123 | 236-183 | 90% |
| Seq ID NO: 83382 | 377-429 | gi|32325123 | 236-183 | 90% |
| Seq ID NO: 83382 | 219-345 | gi|32325123 | 213-84 | 81% |
| Seq ID NO: 83382 | 489-519 | gi|32325123 | 213-183 | 100% |
| Seq ID NO: 83382 | 129-159 | gi|32325123 | 213-183 | 100% |
| Seq ID NO: 83382 | 17-75 | gi|32325123 | 143-84 | 88% |
| Seq ID NO: 83382 | 242-294 | gi|32325123 | 236-183 | 88% |
| Seq ID NO: 83382 | 197-255 | gi|32325123 | 143-84 | 87% |
| Seq ID NO: 83382 | 467-525 | gi|32325123 | 143-84 | 87% |
| Seq ID NO: 83382 | 1-24 | gi|32325123 | 206-183 | 100% |
| Seq ID NO: 83382 | 9-30 | gi|32325123 | 105-84 | 100% |
| Seq ID NO: 83382 | 129-519 | gi|33139983 | 660-271 | 87% |
| Seq ID NO: 83382 | 38-519 | gi|33139983 | 661-178 | 84% |
| Seq ID NO: 83382 | 78-474 | gi|33139983 | 666-271 | 86% |
| Seq ID NO: 83382 | 173-526 | gi|33139983 | 661-309 | 87% |
| Seq ID NO: 83382 | 308-530 | gi|33139983 | 661-440 | 87% |
| Seq ID NO: 83382 | 351-519 | gi|33139983 | 663-495 | 88% |
| Seq ID NO: 83382 | 1-337 | gi|33139983 | 429-87 | 82% |
| Seq ID NO: 83382 | 129-513 | gi|33139225 | 635-252 | 87% |
| Seq ID NO: 83382 | 1-378 | gi|33139225 | 628-252 | 87% |
| Seq ID NO: 83382 | 38-423 | gi|33139225 | 636-252 | 86% |
| Seq ID NO: 83382 | 82-464 | gi|33139225 | 637-256 | 86% |
| Seq ID NO: 83382 | 352-519 | gi|33139225 | 637-470 | 88% |
| Seq ID NO: 83382 | 3-159 | gi|33139225 | 312-153 | 82% |
| Seq ID NO: 83382 | 28-384 | gi|32324170 | 684-328 | 87% |
| Seq ID NO: 83382 | 129-474 | gi|32324170 | 673-328 | 87% |
| Seq ID NO: 83382 | 163-519 | gi|32324170 | 684-328 | 87% |
| Seq ID NO: 83382 | 81-519 | gi|32324170 | 676-235 | 84% |
| Seq ID NO: 83382 | 219-528 | gi|32324170 | 673

TABLE 2-continued

Diverse Parasitic Nematode Nucleotide Coding Sequences Matching *H. glycines* vcDNA sequences

| H. glycines Sequence[1] | Position[2] | GeneID[3] | Position[4] | % identity[5] |
|---|---|---|---|---|
| Seq ID NO: 83382 | 3-439 | gi\|32324170 | 574-132 | 83% |
| Seq ID NO: 83382 | 253-526 | gi\|32324170 | 684-411 | 87% |
| Seq ID NO: 83382 | 1-357 | gi\|32324170 | 486-124 | 82% |
| Seq ID NO: 83382 | 350-530 | gi\|32324170 | 677-497 | 87% |
| Seq ID NO: 83382 | 1-78 | gi\|32324170 | 666-589 | 96% |
| Seq ID NO: 83382 | 433-528 | gi\|32324170 | 684-589 | 90% |
| Seq ID NO: 83382 | 222-519 | gi\|33140346 | 602-302 | 86% |
| Seq ID NO: 83382 | 132-429 | gi\|33140346 | 602-302 | 86% |
| Seq ID NO: 83382 | 42-428 | gi\|33140346 | 602-210 | 83% |
| Seq ID NO: 83382 | 1-338 | gi\|33140346 | 553-210 | 83% |
| Seq ID NO: 83382 | 357-526 | gi\|33140346 | 602-433 | 90% |
| Seq ID NO: 83382 | 17-87 | gi\|33140346 | 168-97 | 91% |
| Seq ID NO: 83382 | 377-439 | gi\|33140346 | 168-105 | 90% |
| Seq ID NO: 83382 | 492-528 | gi\|33140346 | 602-566 | 100% |
| Seq ID NO: 83382 | 467-529 | gi\|33140346 | 168-105 | 89% |
| Seq ID NO: 83382 | 332-394 | gi\|33140346 | 168-105 | 89% |
| Seq ID NO: 83382 | 107-169 | gi\|33140346 | 168-105 | 89% |
| Seq ID NO: 83382 | 197-259 | gi\|33140346 | 168-105 | 89% |
| Seq ID NO: 83382 | 377-434 | gi\|33140346 | 75-17 | 90% |
| Seq ID NO: 83382 | 17-74 | gi\|33140346 | 75-17 | 90% |
| Seq ID NO: 83382 | 1-114 | gi\|33140346 | 418-302 | 82% |
| Seq ID NO: 83382 | 1-34 | gi\|33140346 | 138-105 | 97% |
| Seq ID NO: 83382 | 332-389 | gi\|33140346 | 75-17 | 88% |
| Seq ID NO: 83382 | 107-164 | gi\|33140346 | 75-17 | 88% |
| Seq ID NO: 83382 | 467-524 | gi\|33140346 | 75-17 | 88% |
| Seq ID NO: 83382 | 197-254 | gi\|33140346 | 75-17 | 88% |
| Seq ID NO: 83382 | 1-29 | gi\|33140346 | 45-17 | 96% |
| Seq ID NO: 83382 | 197-384 | gi\|33140426 | 442-254 | 88% |
| Seq ID NO: 83382 | 332-519 | gi\|33140426 | 442-254 | 88% |
| Seq ID NO: 83382 | 287-474 | gi\|33140426 | 442-254 | 87% |
| Seq ID NO: 83382 | 242-429 | gi\|33140426 | 442-254 | 88% |
| Seq ID NO: 83382 | 107-294 | gi\|33140426 | 442-254 | 87% |
| Seq ID NO: 83382 | 1-159 | gi\|33140426 | 412-254 | 89% |
| Seq ID NO: 83382 | 17-204 | gi\|33140426 | 442-254 | 86% |
| Seq ID NO: 83382 | 377-528 | gi\|33140426 | 442-290 | 88% |
| Seq ID NO: 83382 | 62-249 | gi\|33140426 | 442-254 | 86% |
| Seq ID NO: 83382 | 3-87 | gi\|33140426 | 320-236 | 91% |
| Seq ID NO: 83382 | 28-169 | gi\|32325556 | 222-78 | 83% |
| Seq ID NO: 83382 | 298-439 | gi\|32325556 | 222-78 | 82% |
| Seq ID NO: 83382 | 208-357 | gi\|32325556 | 222-70 | 80% |
| Seq ID NO: 83382 | 478-519 | gi\|32325556 | 222-181 | 92% |
| Seq ID NO: 83382 | 17-153 | gi\|32324836 | 149-10 | 83% |
| Seq ID NO: 83382 | 377-513 | gi\|32324836 | 149-10 | 82% |
| Seq ID NO: 83382 | 197-329 | gi\|32324836 | 149-14 | 81% |
| Seq ID NO: 83382 | 107-243 | gi\|32324836 | 149-10 | 81% |
| Seq ID NO: 83382 | 467-519 | gi\|32324836 | 149-97 | 90% |
| Seq ID NO: 83382 | 1-104 | gi\|32324836 | 120-14 | 81% |
| Seq ID NO: 83382 | 38-161 | gi\|33139487 | 219-93 | 83% |
| Seq ID NO: 83382 | 350-384 | gi\|33139487 | 222-188 | 97% |
| Seq ID NO: 83382 | 219-339 | gi\|33139487 | 218-95 | 81% |
| Seq ID NO: 83382 | 398-429 | gi\|33139487 | 219-188 | 96% |
| Seq ID NO: 83382 | 43-153 | gi\|33139115 | 124-11 | 83% |
| Seq ID NO: 83382 | 133-243 | gi\|33139115 | 124-11 | 82% |
| Seq ID NO: 83382 | 403-513 | gi\|33139115 | 124-11 | 82% |
| Seq ID NO: 83382 | 223-329 | gi\|33139115 | 124-15 | 82% |
| Seq ID NO: 83382 | 493-519 | gi\|33139115 | 124-98 | 100% |
| Seq ID NO: 83382 | 358-384 | gi\|33139115 | 124-98 | 100% |
| Seq ID NO: 83407 | 61-104 | gi\|54546446 | 55-98 | 90% |
| Seq ID NO: 83502 | 3-97 | gi\|18090256 | 296-390 | 90% |
| Seq ID NO: 83531 | 1-55 | gi\|33140348 | 201-255 | 98% |
| Seq ID NO: 83556 | 31-110 | gi\|54547037 | 1-80 | 86% |
| Seq ID NO: 83556 | 32-110 | gi\|54547033 | 1-79 | 86% |
| Seq ID NO: 83658 | 281-303 | gi\|33138709 | 165-143 | 100% |
| Seq ID NO: 83658 | 337-357 | gi\|28916076 | 280-260 | 100% |
| Seq ID NO: 83678 | 289-309 | gi\|37853736 | 373-393 | 100% |
| Seq ID NO: 83731 | 1-134 | gi\|32324631 | 49-182 | 94% |
| Seq ID NO: 83731 | 1-107 | gi\|33139363 | 49-152 | 92% |
| Seq ID NO: 83737 | 18-39 | gi\|31326189 | 232-211 | 100% |
| Seq ID NO: 83765 | 226-357 | gi\|7144169 | 364-495 | 87% |
| Seq ID NO: 83765 | 274-335 | gi\|18081294 | 455-516 | 91% |
| Seq ID NO: 83765 | 274-358 | gi\|18089822 | 443-527 | 91% |
| Seq ID NO: 83781 | 408-429 | gi\|17971089 | 242-221 | 100% |
| Seq ID NO: 83828 | 539-605 | gi\|33139668 | 557-491 | 92% |
| Seq ID NO: 83828 | 386-419 | gi\|33139668 | 530-497 | 94% |
| Seq ID NO: 83828 | 347-368 | gi\|33139668 | 530-509 | 100% |
| Seq ID NO: 83828 | 35-56 | gi\|33139668 | 530-509 | 100% |
| Seq ID NO: 83828 | 230-251 | gi\|33139668 | 530-509 | 100% |
| Seq ID NO: 83828 | 566-605 | gi\|33139848 | 530-491 | 97% |
| Seq ID NO: 83855 | 27-51 | gi\|33140021 | 1-25 | 100% |
| Seq ID NO: 47578 | 1-101 | gi\|18382566 | 65-165 | 88% |
| Seq ID NO: 47578 | 7-101 | gi\|18089815 | 2-96 | 88% |
| Seq ID NO: 47578 | 64-98 | gi\|21493534 | 40-74 | 91% |
| Seq ID NO: 84076 | 75-164 | gi\|18081616 | 391-302 | 87% |
| Seq ID NO: 84205 | 295-402 | gi\|18079959 | 358-465 | 82% |
| Seq ID NO: 84241 | 159-179 | gi\|52127565 | 269-249 | 100% |
| Seq ID NO: 84390 | 75-97 | gi\|34028088 | 28-50 | 100% |
| Seq ID NO: 84419 | 109-281 | gi\|33139639 | 255-428 | 88% |
| Seq ID NO: 84419 | 96-242 | gi\|33140673 | 195-49 | 89% |
| Seq ID NO: 84522 | 1-73 | gi\|33140257 | 196-268 | 98% |
| Seq ID NO: 84522 | 44-73 | gi\|32324393 | 1-30 | 100% |
| Seq ID NO: 84576 | 73-112 | gi\|21393592 | 395-434 | 90% |
| Seq ID NO: 84645 | 275-323 | gi\|7143520 | 433-385 | 91% |
| Seq ID NO: 84648 | 6-28 | gi\|35504845 | 119-97 | 100% |
| Seq ID NO: 84664 | 125-168 | gi\|33139131 | 293-336 | 93% |
| Seq ID NO: 84696 | 527-650 | gi\|35504896 | 483-606 | 96% |
| Seq ID NO: 84696 | 1-127 | gi\|35504896 | 213-339 | 96% |
| Seq ID NO: 84696 | 189-267 | gi\|35504896 | 337-415 | 97% |
| Seq ID NO: 84696 | 473-526 | gi\|35504896 | 413-466 | 98% |
| Seq ID NO: 84696 | 40-98 | gi\|7143674 | 296-354 | 93% |
| Seq ID NO: 84696 | 42-98 | gi\|7144456 | 296-352 | 92% |
| Seq ID NO: 84696 | 40-92 | gi\|18382222 | 454-506 | 94% |
| Seq ID NO: 84696 | 40-89 | gi\|18090122 | 491-540 | 94% |
| Seq ID NO: 84696 | 55-92 | gi\|18381283 | 389-426 | 94% |
| Seq ID NO: 84779 | 145-167 | gi\|46985397 | 123-101 | 100% |
| Seq ID NO: 84814 | 20-58 | gi\|28916076 | 1-41 | 92% |
| Seq ID NO: 47631 | 473-497 | gi\|54549558 | 143-167 | 100% |
| Seq ID NO: 84950 | 15-54 | gi\|28916076 | 1-40 | 97% |
| Seq ID NO: 84950 | 8-35 | gi\|159473 | 34-61 | 100% |
| Seq ID NO: 84950 | 8-35 | gi\|2454547 | 227-200 | 100% |
| Seq ID NO: 84950 | 8-35 | gi\|551594 | 194-221 | 100% |
| Seq ID NO: 84950 | 8-35 | gi\|551595 | 669-696 | 100% |
| Seq ID NO: 84950 | 8-35 | gi\|18032254 | 34-61 | 100% |
| Seq ID NO: 84950 | 12-35 | gi\|18477256 | 279-256 | 100% |
| Seq ID NO: 84950 | 12-35 | gi\|18477260 | 325-302 | 100% |
| Seq ID NO: 84950 | 12-35 | gi\|18477262 | 634-611 | 100% |
| Seq ID NO: 84950 | 8-29 | gi\|18477259 | 22-1 | 100% |
| Seq ID NO: 84950 | 8-29 | gi\|18477261 | 22-1 | 100% |
| Seq ID NO: 84950 | 8-29 | gi\|37780968 | 22-1 | 100% |
| Seq ID NO: 84996 | 246-365 | gi\|32324211 | 375-494 | 84% |

Table 2 Legend:
[1]*H. glycines* Clone ID No as set forth in Sequence Listing feature fields; searching the *H. glycines* sequence identifier in column 1 identifies the corresponding SEQ ID NO for that sequence
[2]nucleotide position in SEQ ID NO corresponding to Clone ID No in column 1 that matches with position of sequence of GeneID in adjacent cell on same row of table 2
[3]GeneID number of corresponding matching sequence hit from public database that matches with position of Clone ID No from column 1; derivative organism information is associated with the GeneID No.
[4]nucleotide position in GeneID that matches with nucleotides specified on same row corresponding to sequence of Clone ID SEQ ID NO
[5]percent identity between the two sequences in Clone ID and GeneID Surprisingly the inventors have also discovered that some polynucleotides of the present invention exhibit homology with various insect pests of plants and animals, as illustrated in Table 3. This provides an opportunity to express in plant cells polynucleotides exemplified in Table 3 as double stranded RNA sequences, providing control of many of these insect pests of plants and animals. Mosquitoes, for example, are well known as vectors for spreading malaria, yellow fever, encephalitis, filarial parasites and other serious diseases. Male mosquitoes feed exclusively on plant nectar and on plant cell exudates, and female mosquitoes feed on plants when a blood meal is not available. The present invention therefore provides a means for applying the exemplary sequences as dsRNA molecules expressed in plant cells as a means for controlling nematode and insect pests by expression of sequences identified as representative of common sequences between the two species.

TABLE 3

SCN vcDNA Sequences and Insect Nucleotide Sequence Homologous

| SEQ ID NO[1] | Position[2] | Gene ID[3] | Position[4] | % identity[5] | Genus species[6] |
|---|---|---|---|---|---|
| Seq ID NO: 68821 | 138-159 | CRA\|agCT42044 | 945-966 | 100% | *Anopheles gambiae* |
| Seq ID NO: 79019 | 537-557 | CRA\|agCT43147 | 1437-1457 | 100% | *Anopheles gambiae* |
| Seq ID NO: 47443 | 622-642 | CRA\|agCT43876 | 833-853 | 100% | *Anopheles gambiae* |
| Seq ID NO: 73243 | 46-69 | CRA\|agCT44110 | 215-238 | 100% | *Anopheles gambiae* |
| Seq ID NO: 54820 | 116-136 | CRA\|agCT44330 | 197-177 | 100% | *Anopheles gambiae* |
| Seq ID NO: 65924 | 13-33 | CRA\|agCT44378 | 3440-3460 | 100% | *Anopheles gambiae* |
| Seq ID NO: 53889 | 589-609 | CRA\|agCT44871 | 13437-13457 | 100% | *Anopheles gambiae* |
| Seq ID NO: 66729 | 38-59 | CRA\|agCT45079 | 733-754 | 100% | *Anopheles gambiae* |
| Seq ID NO: 60455 | 259-279 | CRA\|agCT45391 | 1624-1644 | 100% | *Anopheles gambiae* |
| Seq ID NO: 69523 | 121-145 | CRA\|agCT45432 | 192-216 | 96% | *Anopheles gambiae* |
| Seq ID NO: 80670 | 47-67 | CRA\|agCT46846 | 1180-1160 | 100% | *Anopheles gambiae* |
| Seq ID NO: 81791 | 47-69 | CRA\|agCT46968 | 1752-1730 | 100% | *Anopheles gambiae* |
| Seq ID NO: 67053 | 313-339 | CRA\|agCT47874 | 1073-1098 | 96% | *Anopheles gambiae* |
| Seq ID NO: 59568 | 697-718 | CRA\|agCT48203 | 192-171 | 100% | *Anopheles gambiae* |
| Seq ID NO: 72334 | 238-258 | CRA\|agCT49436 | 729-749 | 100% | *Anopheles gambiae* |
| Seq ID NO: 63951 | 103-123 | CRA\|agCT49483 | 652-672 | 100% | *Anopheles gambiae* |
| Seq ID NO: 62555 | 130-150 | CRA\|agCT51096 | 2549-2569 | 100% | *Anopheles gambiae* |
| Seq ID NO: 46459 | 342-364 | CRA\|agCT51427 | 215-237 | 100% | *Anopheles gambiae* |
| Seq ID NO: 66786 | 307-327 | CRA\|agCT52597 | 1900-1920 | 100% | *Anopheles gambiae* |
| Seq ID NO: 68784 | 4-24 | CRA\|agCT55082 | 20600-20620 | 100% | *Anopheles gambiae* |
| Seq ID NO: 53634 | 761-804 | CRA\|agCT55207 | 620-577 | 89% | *Anopheles gambiae* |
| Seq ID NO: 53634 | 754-774 | CRA\|agCT55207 | 597-577 | 100% | *Anopheles gambiae* |
| Seq ID NO: 53635 | 58-101 | CRA\|agCT55207 | 577-620 | 89% | *Anopheles gambiae* |
| Seq ID NO: 53635 | 88-108 | CRA\|agCT55207 | 577-597 | 100% | *Anopheles gambiae* |
| Seq ID NO: 73360 | 270-291 | CRA\|agCT55621 | 744-723 | 100% | *Anopheles gambiae* |
| Seq ID NO: 82401 | 107-127 | CRA\|agCT55677 | 848-868 | 100% | *Anopheles gambiae* |
| Seq ID NO: 55012 | 650-670 | EBI\|221 | 281-261 | 100% | *Anopheles gambiae* |
| Seq ID NO: 78551 | 90-110 | EBI\|2300 | 624-644 | 100% | *Anopheles gambiae* |
| Seq ID NO: 68299 | 84-105 | EBI\|2307 | 2080-2101 | 100% | *Anopheles gambiae* |
| Seq ID NO: 47206 | 84-105 | EBI\|2307 | 2080-2101 | 100% | *Anopheles gambiae* |
| Seq ID NO: 68556 | 241-262 | EBI\|4053 | 3009-3030 | 100% | *Anopheles gambiae* |
| Seq ID NO: 70190 | 174-194 | EBI\|4283 | 5460-5440 | 100% | *Anopheles gambiae* |
| Seq ID NO: 53886 | 405-425 | EBI\|5326 | 2105-2085 | 100% | *Anopheles gambiae* |
| Seq ID NO: 70190 | 243-266 | EBI\|8982 | 1366-1389 | 100% | *Anopheles gambiae* |
| Seq ID NO: 51267 | 164-184 | EBI\|9090 | 121-141 | 100% | *Anopheles gambiae* |
| Seq ID NO: 55175 | 12-41 | gi\|11119314 | 36-7 | 100% | *Andrya cuniculi* |
| Seq ID NO: 66692 | 12-41 | gi\|11119314 | 36-7 | 100% | *Andrya cuniculi* |
| Seq ID NO: 55175 | 12-41 | gi\|11119315 | 36-7 | 100% | *Paranoplocephala* sp. |
| Seq ID NO: 66692 | 12-41 | gi\|11119315 | 36-7 | 100% | *Paranoplocephala* sp. |
| Seq ID NO: 55175 | 12-41 | gi\|11119317 | 36-7 | 100% | *Paranoplocephala arctica* |
| Seq ID NO: 66692 | 12-41 | gi\|11119317 | 36-7 | 100% | *Paranoplocephala arctica* |
| Seq ID NO: 55175 | 12-41 | gi\|11119319 | 36-7 | 100% | *Paranoplocephala serrata* |
| Seq ID NO: 66692 | 12-41 | gi\|11119319 | 36-7 | 100% | *Paranoplocephala serrata* |
| Seq ID NO: 47304 | 674-696 | gi\|23186984 | 477-499 | 100% | *Echinococcus granulosus* |
| Seq ID NO: 77038 | 16-43 | gi\|2463301 | 112-85 | 96% | *Neogryporhynchus cheilancristrotus* |
| Seq ID NO: 59901 | 75-96 | gi\|31365321 | 176-155 | 100% | *Toxoptera citricida* |
| Seq ID NO: 51042 | 482-505 | gi\|31365444 | 320-297 | 100% | *Toxoptera citricida* |
| Seq ID NO: 77354 | 97-117 | gi\|31365580 | 644-664 | 100% | *Toxoptera citricida* |
| Seq ID NO: 82622 | 494-514 | gi\|37804570 | 57-77 | 100% | *Rhopalosiphum padi* |
| Seq ID NO: 66861 | 73-95 | gi\|46996593 | 400-378 | 100% | *Acyrthosiphon pisum* |
| Seq ID NO: 64007 | 76-96 | gi\|46996721 | 468-448 | 100% | *Acyrthosiphon pisum* |
| Seq ID NO: 60081 | 70-96 | gi\|46998065 | 535-562 | 96% | *Acyrthosiphon pisum* |
| Seq ID NO: 54610 | 316-337 | gi\|46998427 | 300-279 | 100% | *Acyrthosiphon pisum* |
| Seq ID NO: 47304 | 674-695 | gi\|47163116 | 387-408 | 100% | *Echinococcus granulosus* |
| Seq ID NO: 62977 | 216-237 | gi\|47514887 | 260-281 | 100% | *Acyrthosiphon pisum* |
| Seq ID NO: 58768 | 293-314 | gi\|47517134 | 76-55 | 100% | *Acyrthosiphon pisum* |
| Seq ID NO: 63826 | 72-92 | gi\|47522032 | 581-561 | 100% | *Acyrthosiphon pisum* |
| Seq ID NO: 82094 | 183-203 | gi\|47533062 | 209-189 | 100% | *Acyrthosiphon pisum* |
| Seq ID NO: 72433 | 558-578 | gi\|47536611 | 364-384 | 100% | *Acyrthosiphon pisum* |
| Seq ID NO: 57774 | 203-223 | gi\|47536768 | 381-401 | 100% | *Acyrthosi TABLE 3-continued SCN vcDNA Sequences and Insect Nucleotide Sequence Homologous

| SEQ ID NO[1] | Position[2] | Gene ID[3] | Position[4] | % identity[5] | Genus species[6] |
|---|---|---|---|---|---|
| Seq ID NO: 66692 | 12-41 | gi\|54306320 | 36-7 | 100% | Moniezia sp. |
| Seq ID NO: 55175 | 12-41 | gi\|54306321 | 36-7 | 100% | Monoecocestus americanus |
| Seq ID NO: 66692 | 12-41 | gi\|54306321 | 36-7 | 100% | Monoecocestus americanus |
| Seq ID NO: 55175 | 12-41 | gi\|54306322 | 36-7 | 100% | Paranoplocephala blanchardi |
| Seq ID NO: 66692 | 12-41 | gi\|54306322 | 36-7 | 100% | Paranoplocephala blanchardi |
| Seq ID NO: 55175 | 12-41 | gi\|54306323 | 36-7 | 100% | Paranoplocephala etholeni |
| Seq ID NO: 66692 | 12-41 | gi\|54306323 | 36-7 | 100% | Paranoplocephala etholeni |
| Seq ID NO: 55175 | 12-41 | gi\|54306324 | 36-7 | 100% | Paranoplocephala fellmani |
| Seq ID NO: 66692 | 12-41 | gi\|54306324 | 36-7 | 100% | Paranoplocephala fellmani |
| Seq ID NO: 55175 | 12-41 | gi\|54306325 | 36-7 | 100% | Paranoplocephala gracilis |
| Seq ID NO: 66692 | 12-41 | gi\|54306325 | 36-7 | 100% | Paranoplocephala gracilis |
| Seq ID NO: 55175 | 12-41 | gi\|54306326 | 36-7 | 100% | Paranoplocephala longivaginata |
| Seq ID NO: 66692 | 12-41 | gi\|54306326 | 36-7 | 100% | Paranoplocephala longivaginata |
| Seq ID NO: 55175 | 12-41 | gi\|54306327 | 36-7 | 100% | Paranoplocephala macrocephala |
| Seq ID NO: 66692 | 12-41 | gi\|54306327 | 36-7 | 100% | Paranoplocephala macrocephala |
| Seq ID NO: 55175 | 12-41 | gi\|54306328 | 36-7 | 100% | Paranoplocephala cf. |
| Seq ID NO: 66692 | 12-41 | gi\|54306328 | 36-7 | 100% | Paranoplocephala cf. |
| Seq ID NO: 55175 | 12-41 | gi\|54306329 | 36-7 | 100% | Paranoplocephala kalelai |
| Seq ID NO: 66692 | 12-41 | gi\|54306329 | 36-7 | 100% | Paranoplocephala kalelai |
| Seq ID NO: 55175 | 12-41 | gi\|54306331 | 36-7 | 100% | Paranoplocephala primordialis |
| Seq ID NO: 66692 | 12-41 | gi\|54306331 | 36-7 | 100% | Paranoplocephala primordialis |
| Seq ID NO: 55175 | 12-41 | gi\|54306332 | 36-7 | 100% | Schizorchis sp. |
| Seq ID NO: 66692 | 12-41 | gi\|54306332 | 36-7 | 100% | Schizorchis sp. |
| Seq ID NO: 60083 | 406-426 | gi\|55794409 | 449-429 | 100% | Acyrthosiphon pisum |
| Seq ID NO: 62688 | 3-23 | gi\|55802365 | 769-789 | 100% | Acyrthosiphon pisum |
| Seq ID NO: 82614 | 269-290 | gi\|55803329 | 472-493 | 100% | Acyrthosiphon pisum |
| Seq ID NO: 54865 | 19-41 | gi\|55806106 | 709-731 | 100% | Acyrthosiphon pisum |
| Seq ID NO: 65500 | 126-146 | gi\|55810448 | 308-328 | 100% | Acyrthosiphon pisum |
| Seq ID NO: 80198 | 225-245 | gi\|55810583 | 245-265 | 100% | Acyrthosiphon pisum |
| Seq ID NO: 51184 | 74-94 | gi\|55814836 | 337-317 | 100% | Acyrthosiphon pisum |
| Seq ID NO: 52762 | 1-36 | gi\|6467344 | 700-665 | 91% | Duplicibothrium paulum |

Table 3 Legend:
[1]H. glycines Clone ID No as set forth in Sequence Listing feature fields; searching the H. glycines sequence identifier in column 1 identifies the corresponding SEQ ID NO for that sequence
[2]nucleotide position in SEQ ID NO corresponding to Clone ID No in column 1 that matches with position of sequence of Gene ID in column 3 on same row
[3]Gene ID number of corresponding matching sequence hit from public database that matches with position of Clone ID No from column 1; information in table is sorted by column 3
[4]Gene ID nucleotide position in column 3 that matches with nucleotides specified on same row corresponding to sequence of SCN Clone ID
[5]percent identity between the two sequences in Clone ID and Gene ID (comparison of identity between column 2 and column 4 sequences)
[6]Genus and species of organism corresponding to gene sequence set forth in Column 3

Example 6

This example illustrates the suppression of one or more genes in a soybean cyst nematode by providing in the diet of the nematode a double stranded RNA consisting of a nucleotide sequence that is complementary to the messenger RNA sequence expressed from the one or more soybean cyst nematode genes.

Soybean cyst nematode J2 larvae are treated with a double stranded RNA derived from a nucleotide sequence selected from the group consisting of SEQ ID NO:1-SEQ ID NO:97729 in a soaking assay as described in WO 03052110. Briefly, freshly hatched nematode larvae are treated in a soaking buffer (10 mM octopamine in M9 salts, 1 mg/ml FITC in DMF) with or without 2 microgram/microliter of dsRNA for four hours at room temperature. Larvae ingesting the solution are fluorescent. The fluorescent larvae are separated from non-fluorescent larvae, then inoculated into soil containing a germinated soybean seedling. The number of cysts on each plant are counted about 35 days after inoculation. The tested dsRNA molecules that demonstrate significant reduction in the number of cysts counted are then made into plant expression cassettes contained in DNA constructs designed for plant cell transformation. DNA constructs generally comprise constitutive promoters that cause transcription of a linked DNA that transcribes a dsRNA. Promoters that may exhibit enhanced expression in root tissue may be particularly useful for expressing dsRNA effective against soybean cyst nematodes.

These DNA constructs are transformed into soybean plant cells and the cells regenerated into plants. The plants are tested either as Ro plants for nematode resistance or seed is collected and the R1 seed is germinated and the R1 plant roots tested for nematode resistance. Resistance is demonstrated if the transgenic plants have a significant reduction in cyst number or cyst development.

Example 7

This example describes DNA constructs and the expression of a chimeric RNA molecule of the present invention in a transgenic soybean plant cell. The DNA constructs described herein comprise a promoter that causes transcription of an operably linked DNA into an RNA in a soybean cell, the DNA and the transcribed RNA of one or more segments exhibiting homology or complementarity to a soybean cyst nematode contiguous at least about 21-mer nucleotide sequence (DNA or RNA). Exemplary soybean cyst nematode DNA segments were previously described in Table 1 and are further identified in the Sequence Listing as SEQ ID NO:1-SEQ ID NO:45568. When expressed in a plant cell, the DNA construct provides an RNA transcript molecule comprising a self-complimentary segment, a portion of which folds into a double stranded RNA (dsRNA). Detection of the RNA transcript expressed in a cell or tissue of a transgenic plant is diagnostic for the DNA construct(s) that comprises a region of a soybean cyst nematode DNA molecule, and demonstrates that the DNA segment from which the dsRNA molecule is derived is transcribed/expressed in the transgenic soybean cells. Therefore, the transcribed RNA becomes available in the diet of the nematode as it feeds on a plant root cell. The RNA comprises a region that is double stranded and is complementary to a naturally occurring polynucleic acid molecule contained in a soybean cyst nematode cell, and when ingested by the nematode results in suppression of the normal level of the naturally occurring molecule.

Exemplary DNA constructs of the present invention have various regulatory elements that provide transcription or enhance expression or stability of an RNA molecule transcribed from a transgene in a plant cell. For example, a promoter element of a DNA construct of the present invention provides expression of an RNA transcript in a plant cell. Promoters, which can cause the transcription of a linked heterologous DNA are generally known in the art, for example, DNA plant virus promoters (P-CaMV35S, U.S. Pat. Nos. 5,352,605 and 5,196,525, comprising a duplicated enhancer region herein referred to as P-e35S; P-FMV35S, U.S. Pat. Nos. 5,378,619 and 5,018,100, herein incorporated by reference in their entirety), and various plant derived promoters, for example, plant actin promoters (P-Os.Act, U.S. Pat. Nos. 5,641,876 and 6,429,357, herein incorporated by reference in their entirety), and chimeric promoters, for example, P-FMV-Elf1α (U.S. Pat. No. 6,660,911 and other chimeric promoters disclosed therein, herein incorporated by reference in their entirety). Additionally, promoters that provide enhanced expression in root cells relative to other plant cells, may be tested and selected to express the RNA molecules of the present invention. The DNA constructs described in this example utilize the P-e35S and P-FMV promoters to drive the transcription of a DNA and expression of a dsRNA that exhibits homology to a portion of a soybean cyst nematode nucleotide sequence. For example, a nucleotide sequence was assembled consisting of two segments, the forward and reverse nucleotide sequence of SEQ ID NO:22219 from nucleotide position 552-699, linked by an amorphous 20-200 nucleotide segment that did not exhibit any known complementarity to the SCN genome sequences. Bioinformatics analysis indicates that the nucleotide sequence of SEQ ID NO:22219 corresponds to an open reading frame encoding an SCN specific proteasome A-type subunit peptide referred to herein as Pas-4. This chimeric sequence was incorporated into plant expression vectors for use in testing dsRNA mediated suppression of the pas-4 target gene. The DNA constructs 5749 (P-FMV/Pas-4-dsRNA/E6 3' UTR) was thus assembled and comprises the necessary transfer molecules and regulatory molecules to provide integration into the genome of plant cells and expression of the dsRNA molecule therein.

The DNA constructs comprise a T-DNA region that is transferred into the genome of a plant cell by an *Agrobacterium*- or *Rhizobium*-mediated plant cell transformation method, and additional regulatory elements, for example, a 3' untranslated region (3' UTR) of the SIE6-3B gene from *Gossypium barbadense*, herein referred to as E6 3' UTR (John Plant Mol Biol 30:297-306, 1996, NCBI accession U30508, nucleotide position from about 992-1304). The DNA construct 5749 (P-FMV/Pas-4-dsRNA/E6 3' UTR) was transferred into *Agrobacterium rhizogenes* strain.

A transgenic root culture of soybean has been shown to support soybean cyst nematode infection and is useful for the expression of transgenes (Narayanan, et al., Crop Sci. 39:1680-1686, 1999 and Cho et al., Planta (2000) 210:195-204). *Agrobacterium rhizogenes* transformed to contain the described DNA construct 5749 was used to transformed soybean cells and create independent transgenic root cultures, referred to herein as events 5749-1, etc. Tissues from the transgenic root cultures were assayed for expression of the chimeric SCN gene suppression RNA molecule. Transgenic root tissues were selected using appropriate selection pressures. Transgenic root tissues from each event were screened for the presence of the fluorescence marker expression that was integrated into and adjacent to the dsRNA expression construct. The transgenic root tissues were also screened for the presence of siRNA segments produced from exposure to the root tissue cells' endogenous DICER molecules. siRNA segments were screened for identity to segments of the corresponding dsRNA coding sequences expressed from the plasmid construct expression cassettes. Methods for detecting the presence of an expressed RNA in a cell are known in the art. For example, in this example, the presence of the 3' UTR was detected using primers that functioned to amplify the UTR sequence from the expressed RNA sequence. A TAQMAN method was then used along with a 3' UTR specific fluorescence probe to detect the UTR as well as provide information on the relative level of expression from the construct. The data is shown in Table 4.

TABLE 4

Levels of Pas-4-dsRNA in Transgenic Soybean Root Cells.

| Event | Ave fluorescense | St Dev | siRNA Northern |
|---|---|---|---|
| Vector control | 0.00 | 0.00 | ND |
| 5749-1 | 2.30 | 1.05 | + |
| 5749-3 | 3.83 | 1.39 | + |
| 5749-4 | 5.47 | 2.44 | + |
| 5749-5 | 3.73 | 0.64 | + |
| 5749-8 | 0.45 | 0.14 | ND |
| 5749-10 | 0.16 | 0.02 | ND |
| 5749-11 | 0.24 | 0.04 | + |
| 5749-12 | 0.33 | 0.17 | ND |
| 5749-A | 3.14 | 0.70 | + |
| 5749-B | 2.91 | 0.27 | + |

ND — not detected

The data in Table 4 indicates that ten events comprising the Pas-4-dsRNA contained detectable levels of the RNA molecule. Northern blot analysis of these events showed detectable levels of siRNA that specifically hybridizes to DNA probes made from a homologous fragment of the Pas-4 coding region. These results demonstrate that soybean cells can be transformed with DNA constructs for expression of dsRNA molecules specific for gene suppression of SCN target genes, and that the transformed plant cells recognize the RNA molecules and dice them into detectable siRNA molecules that may be useful for specific gene suppression of the target gene(s) when provided in the diet of soybean cyst nematodes.

All patent publications cited in this specification are incorporated herein by reference to the same extent as if each individual publication or patent application was specifically and individually indicated to be incorporated by reference.

The Sequence Listing is submitted along with this specification on two compact discs. One disc is labeled 'Sequence Listing' according to 37 CFR §1.52(e)(4), and the other disc is labeled 'CRF' (computer readable form) according to 37 CFR §1.821(e). Each disc contains a single 271,645 kilo-byte text file labeled 'SCN_seqListing.txt', created on Feb. 22, 2005, in IBM-PC format and is compatible with IBM-PC, MS-Windows, Macintosh, and UNIX operating systems. The sequence listing information recorded in computer readable form is identical to the written compact disc sequence listing. The Sequence Listing text file is incorporated herein by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08067671B2). An electronic copy of the "Sequence Listing" will also be available from the USPTO upon request and payment of the fee set forth in 37 CFR 1.19(b)(3).

What is claimed is:

1. A method for suppressing a peptide coding sequence in a *Heterodera glycines* pest, comprising selecting a target polynucleotide sequence of a *Heterodera glycines* pest genome comprising at least from about 24 contiguous nucleotides, expressing the target polynucleotide sequence as an RNA sequence that forms a double stranded RNA structure in a plant cell, and providing said plant cell in the diet of said *Heterodera glycines* pest, wherein uptake of the contents of said cell by said pest results in the morbidity and/or mortality of said pest, and wherein said target polynucleotide sequence is SEQ ID NO:22219.

2. The method of claim 1, wherein said RNA sequence comprises contiguous nucleotides from at least two or more target polynucleotide sequences from two or more different coding sequences of a *Heterodera glycines* pest.

3. The method of claim 2, wherein each of said two or more different coding sequences are isolated from different *Heterodera glycines* cDNA sequences.

4. A method for controlling *Heterodera glycines* infection in a soybean plant comprising:

a) transforming a soybean plant cell with a DNA construct that expresses a dsRNA molecule in said soybean cell; and b) regenerating said transformed soybean plant cell into a fertile transgenic soybean plant that exhibits resistance to infection by *Heterodera glycines*;

wherein said DNA construct comprises a polynucleotide sequence comprising at least about 24 contiguous nucleotides of SEQ ID NO:22219, or the complement thereof.

5. The method of claim 4, wherein said DNA construct comprises at least one selectable marker providing herbicide tolerance to the transgenic soybean plant.

6. The method of claim 5, wherein said transgenic soybean plant exhibits tolerance to the herbicide glyphosate.

7. A transgenic soybean plant comprising the double stranded structure of claim 1.

8. A seed produced from the plant of claim 7, wherein said seed comprises said structure.

9. A plant grown from the seed of claim 8.

* * * * *